United States Patent
Baylin et al.

(10) Patent No.: US 10,966,998 B2
(45) Date of Patent: Apr. 6, 2021

(54) CANCER THERAPY VIA A COMBINATION OF EPIGENETIC MODULATION AND IMMUNE MODULATION

(71) Applicant: The Johns Hopkins University, Baltimore, MD (US)

(72) Inventors: Stephen B. Baylin, Baltimore, MD (US); Drew M. Pardoll, Brookeville, MD (US); Suzanne L. Topalian, Brookeville, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/916,235

(22) PCT Filed: Sep. 5, 2014

(86) PCT No.: PCT/US2014/054201
§ 371 (c)(1),
(2) Date: Mar. 3, 2016

(87) PCT Pub. No.: WO2015/035112
PCT Pub. Date: Mar. 12, 2015

(65) Prior Publication Data
US 2016/0193239 A1 Jul. 7, 2016

Related U.S. Application Data

(60) Provisional application No. 61/874,185, filed on Sep. 5, 2013.

(51) Int. Cl.
| | |
|---|---|
| A61K 39/00 | (2006.01) |
| A61K 31/706 | (2006.01) |
| A61K 38/15 | (2006.01) |
| A61K 39/395 | (2006.01) |
| A61K 31/167 | (2006.01) |
| C07K 16/28 | (2006.01) |
| A61K 45/06 | (2006.01) |
| C12Q 1/6886 | (2018.01) |

(52) U.S. Cl.
CPC .......... *A61K 31/706* (2013.01); *A61K 31/167* (2013.01); *A61K 38/15* (2013.01); *A61K 39/395* (2013.01); *A61K 39/3955* (2013.01); *A61K 45/06* (2013.01); *C07K 16/2818* (2013.01); *C07K 16/2827* (2013.01); *C12Q 1/6886* (2013.01); *A61K 2039/505* (2013.01); *C12Q 2600/106* (2013.01); *C12Q 2600/154* (2013.01)

(58) Field of Classification Search
CPC .. A61K 31/706; A61K 39/3955; A61K 45/06; A61K 2039/505; C12Q 1/6886
See application file for complete search history.

(56) References Cited

U.S. PATENT DOCUMENTS

2015/0374731 A1  12/2015  Maio et al.

FOREIGN PATENT DOCUMENTS

| WO | WO-2010054126 A2 | 5/2010 |
| WO | WO-2012153187 A2 | 11/2012 |

OTHER PUBLICATIONS

Brahmer et al (Cancer Immuno Res 1:85-91, online pub Jul. 22, 2013 (Year: 2013).*
Wrangle et al (AACR meeting , abstract 4619, Apr. 2013 (Year: 2013).*
Liu et al (Frontiers in oncology, 3:May 1-8, 2013 (Year: 2013).*
Payne et al (Clin and Dev Immu, vol. 2012: Sep. 1-8, 2012 (Year: 2012).*
Konishi et al (Clin Can Res 10:5094-5100, 2004) (Year: 2004).*
Kamphorst et al (Current Opin in Immuno, 25:381-389, 2013) (Year: 2013).*
Jarvis et al (Int J Cancer 71:1049-1055, 1997). (Year: 1997).*
Peixoto et al (Biochem J. 423:381-7, 2009) (Year: 2009).*
Brahmer. Immune checkpoint inhibitors: making immunotherapy a reality for the treatment of lunch cancer. Cancer Immunology Research. Jul. 22, 2013. vol. 1, No. 2, pp. 85-91.
Zheng et al. 5-Aza-2-deoxycytidine reactivates gene expression via degradation of pRb pocket proteins. The FASEB Journal. 2012. vol. 26, pp. 449-459.
Pardoll. The blockade of immune checkpoints in cancer immunotherapy. Nature Reviews Cancer. 2012, vol. 12, pp. 252-264.

* cited by examiner

*Primary Examiner* — Lei Yao
(74) *Attorney, Agent, or Firm* — Mintz Levin Cohn Ferris Glovsky and Popeo, P.C.; Peter F. Corless

(57) ABSTRACT

Cancer therapies that combine epigenetic modulating agent(s) with immune modulating agent(s), which were remarkably identified to provide an improved treatment regimen over single agent therapy, are disclosed. In particular embodiments, the invention provides for improved treatment of NSCLC in patients via administration of exemplary immune modulating agents anti-PD-1 antibody or anti-PD-L1 antibody, which were observed to show enhanced activity in combination with the exemplary epigenetic modulating agent 5-deoxyazacytidine. Further, expression markers of responsive neoplastic cells are also disclosed.

8 Claims, 40 Drawing Sheets

Figure 2

Pro-Inflammatory Changes Gene Expression Revealed to Increase with AZA Treatment

EPITHELIAL

CSAR: 549, 103, 104
GMCSF: 358, HCC827
MHC's: MCF7
TNF-alpha: MCF7
IL1 alpha/beta: HCC827, 549, MCF7
IL6: 358, HCC827
IL8:
IL-15:
IL-15R: 358
IL15RA: 358
MMP's - TIMP1: 358, 838, 1299, HCC827, 103, 104
COX2: 358
OncostatinM: 838, 549, 103
ICAM1, VCAM1: 1299
TGF-beta's and R's: 358, 1299, 2170, 549, 103, 104

AML

INFR-gamma: 1107; KG1a
TNF-alpha: 1107, Kasumi, KG1a
MHC's: 1107, Kasumi, KG1a
HLA B,C,G: Kasumi, KG1a
TLR4: Kasumi
DAP12: Kasumi; KG1a
CD13-macrophage maturation: Kasumi
IL-1RI: 1107, KG1a
IL1 alpha/beta: Kasumi; KG1a
MMP's - TIMP1: KG1a
OncostatinM: 1107
TGF-beta's and R's: Kasumi; KG1a Therapeutic Implications For PD-1 Pathway Blockade of Adaptive Resistance Model Response of a "non-immunogenic" tumor to anti-PD-1: Stage 4 NSCLC with prior epigenetic therapy Epigenetic Therapy Followed by Anti-PD-1:
A Potentially Synergistic Combination for Stage IV NSCLC

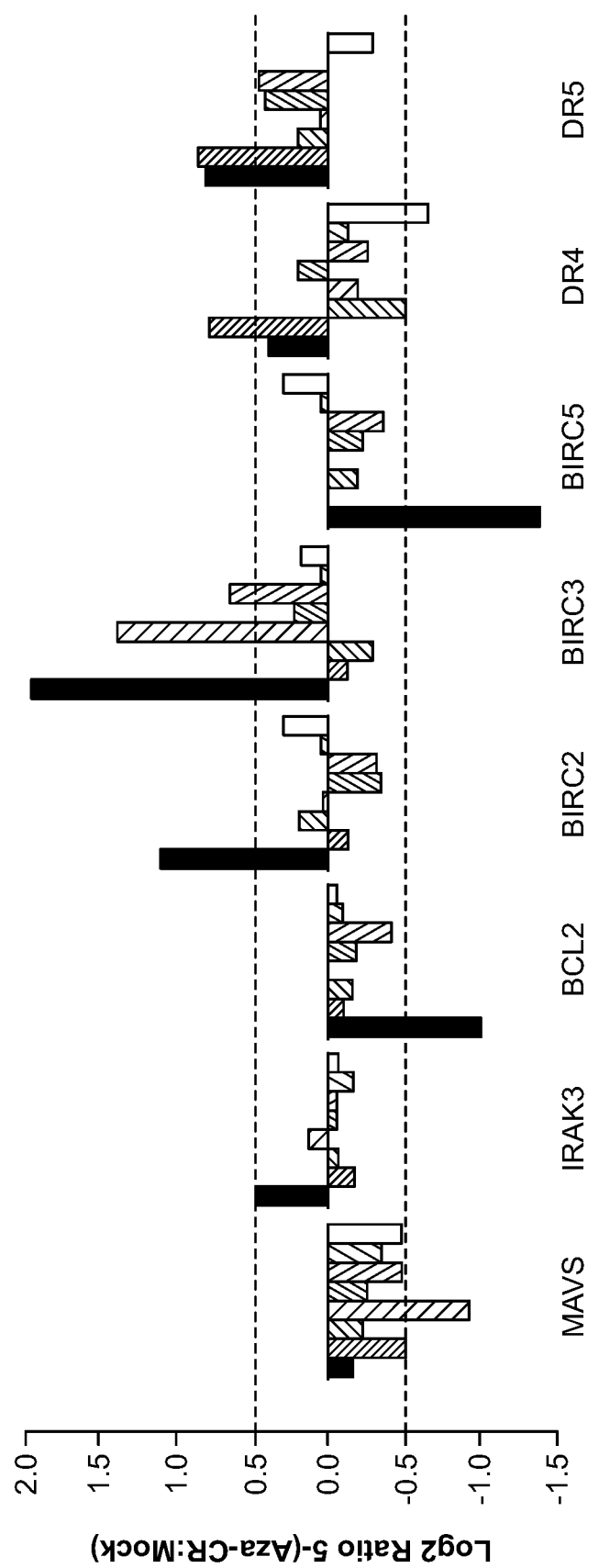

FIG. 23A
Pt. 1
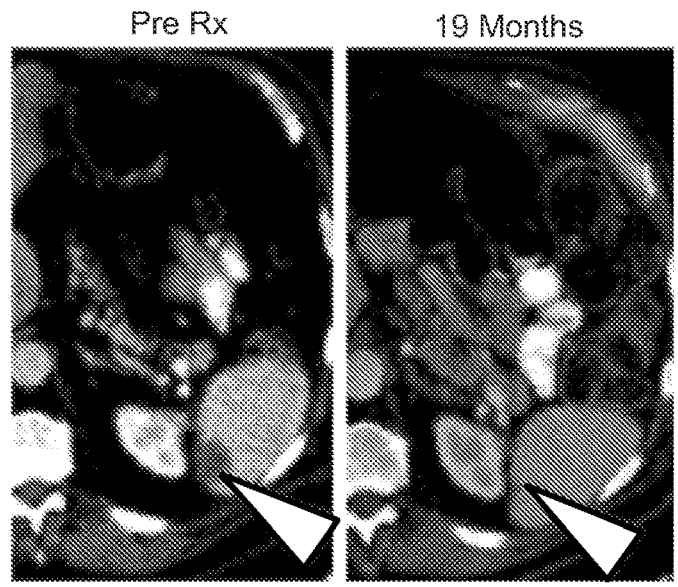
Pt. 2
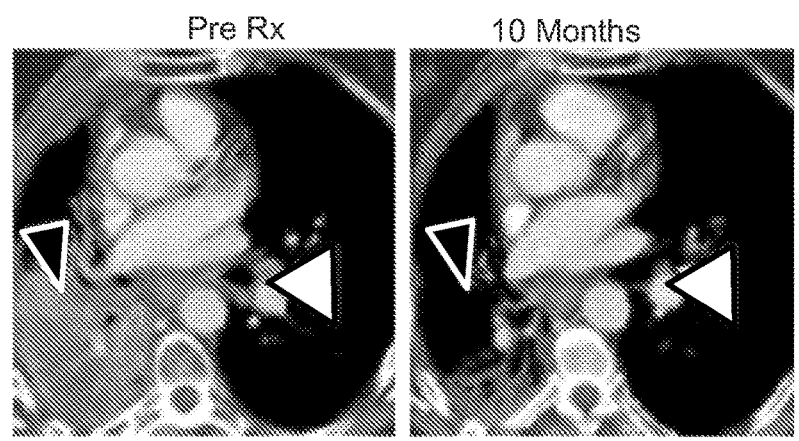
Pt. 3
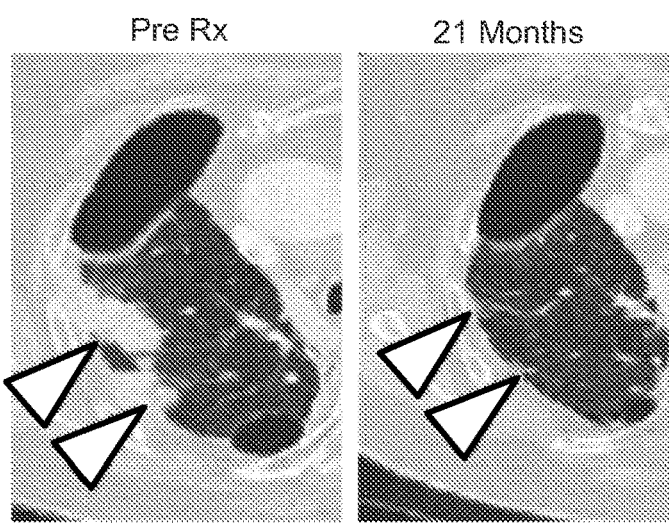

FIG. 23C

| Patient | 1 | 2 | 3 | 4 | 5 |
|---|---|---|---|---|---|
| Age | 62 | 62 | 64 | 68 | 62 |
| Histology | Adeno | Squamous | Adeno | Squamous | Squamous |
| Number of treatments before epigenetic therapy | 3 | 1 | 1 | 1 | 1 |
| Best response to any prior therapy | SD | PR | SD | PD | PR |
| Duration of treatment with azacitidine & entinostat prior to immune check-point blockade (months) | 2 | 2 | 6 | 2 | 8 |
| Best response to epigenetic therapy | PD | PD | MR | PD | PR |
| Type of immune check-point blockade | Anti-PD1 | Anti-PD1 | Anti-PD-L1 | Anti-PD1 | Anti-PD-L1 |
| Duration of immune check-point blockade | 23+ months (ongoing) | 26+ months (ongoing) | 14+ months (ongoing) | 8.25 months | 8.5 months |
| Response to immune check-point blockade | PR (-57%) | PR (-73%) | PR (-64%) | SD (+11%) | SD (+18%) |

SD = Stable Disease
PR = Partial Response
PD = Progressive Disease
MR = Mixed Response (some lesions responding, some progressing)
Adeno – Non-small cell lung adenocarcinoma
Squamous – None-small cell lung squamous cell carcinoma

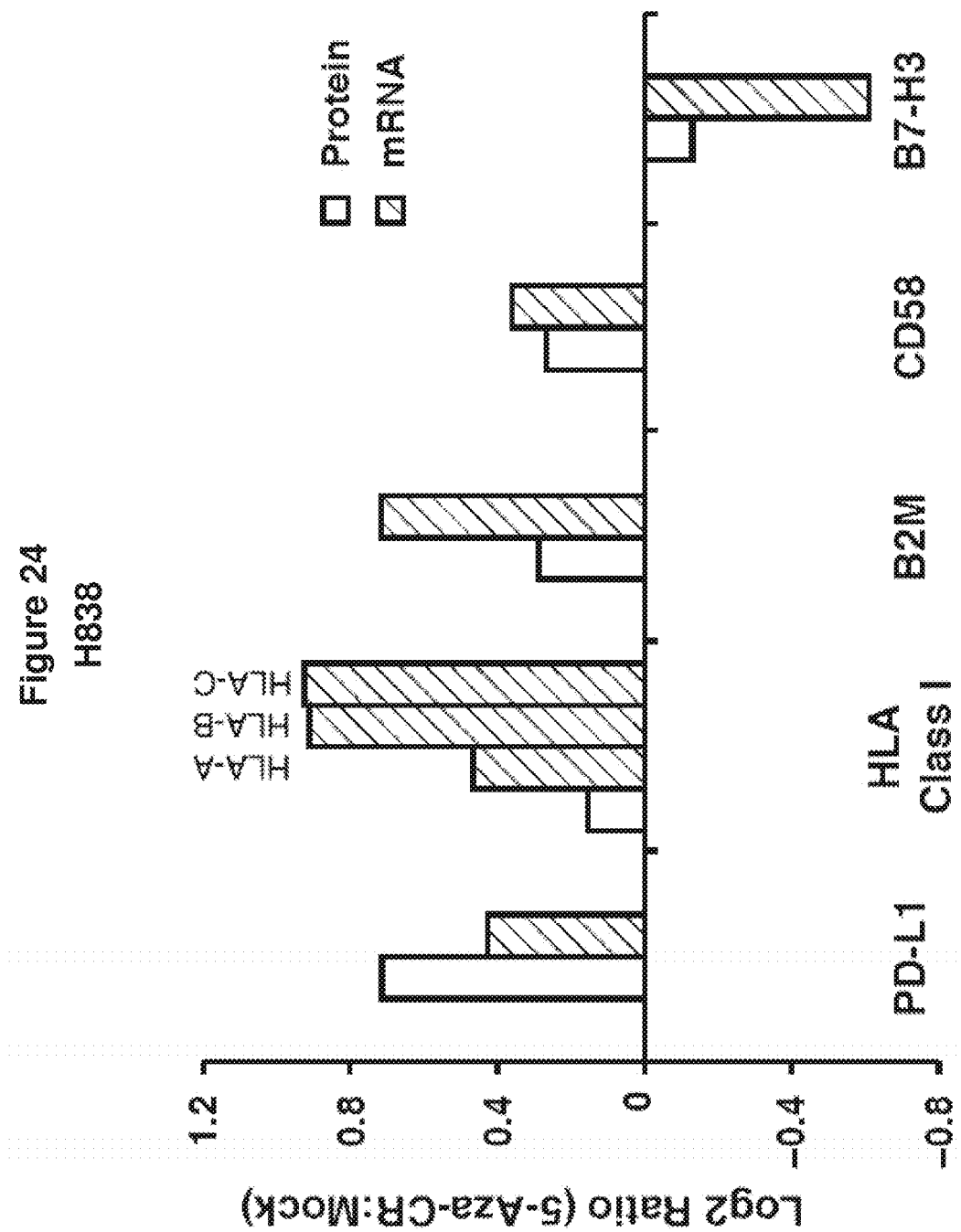

Figure 25

| Gene Symbol | Expression Fold Change (Aza/Mock) | Genes with Available RNA-seq Data from TCGA | Chr | Gene Symbol | Expression Fold Change (Aza/Mock) | Genes with Available RNA-seq Data from TCGA | Chr | Gene Symbol | Expression Fold Change (Aza/Mock) | Genes with Available RNA-seq Data from TCGA | Chr |
|---|---|---|---|---|---|---|---|---|---|---|---|
| AQAM8 | 13.1 | Yes | 10 | HLA-F | 4.1 | Yes | 6 | PARP12 | 5.5 | Yes | 7 |
| ANKRD1 | 8.1 | Yes | 10 | IFFO1 | 4.0 | Yes | 12 | PARP14 | 4.2 | Yes | 3 |
| ANXA8L2 | 6.0 | Yes | 10 | IFI6 | 7.8 | Yes | 1 | PARP9 | 7.3 | Yes | 3 |
| APEG3 | 4.1 | Yes | 4 | IFI27 | 22.2 | Yes | 14 | PLAT | 4.3 | Yes | 8 |
| APH1CD58 | 5.8 | Yes | 12 | IFI44 | 25.0 | Yes | 1 | PLK2 | 4.2 | Yes | 5 |
| B2M * | 3.9 | | 15 | IFI44L | 23.3 | Yes | 1 | PLSCR1 | 8.2 | Yes | 3 |
| BATF2 | 4.4 | Yes | 11 | IFI6 | 5.2 | Yes | 1 | PRSS23 | 4.7 | Yes | 11 |
| BST2 | 7.9 | Yes | 19 | IFIH1 | 6.8 | Yes | 2 | PSME9 | 4.0 | Yes | 14 |
| CA8P8 | 10.8 | Yes | 1 | IFIT1 | 28.7 | Yes | 10 | REC8 | 4.8 | Yes | 14 |
| CCL5 | 5.0 | Yes | 17 | IFIT2 | 8.4 | Yes | 10 | RP3A | 4.5 | Yes | 3 |
| CLDN1 | 4.1 | Yes | 3 | IFIT3 | 22.2 | Yes | 10 | RTP4 | 8.0 | Yes | 3 |
| CLDN8 | 4.4 | Yes | 18 | IFIT5 | 8.1 | Yes | 10 | S100A16 | 4.1 | Yes | 1 |
| CMPK2 | 4.7 | Yes | 2 | IFITM1 | 8.8 | Yes | 11 | SAMD9L | 8.7 | Yes | 7 |
| COX7B2 | 9.7 | Yes | 4 | IFITM2 | 9.3 | Yes | 11 | SP110 | 8.1 | Yes | 2 |
| CST9 | 11.7 | Yes | 11 | IFIT43 | 13.4 | Yes | 11 | SPAXKA1 | 28.8 | | X |
| CT45A1 | 3.8 | Yes | 3 | IFIT44P | 12.7 | | 3 | SPAXKB2 | 36.8 | Yes | X |
| CT45A3 | 16.9 | Yes | X | IGFBP3 | 8.8 | Yes | 8 | SPAXKD | 25.3 | | X |
| CXCL11 | 20.7 | Yes | 4 | IRF7 | 7.9 | Yes | 13 | SPINK1 | 5.3 | Yes | 5 |
| DDX58 | 5.3 | Yes | 9 | IRF9 | 10.7 | Yes | 14 | SRGN | 4.7 | Yes | 10 |
| DDX60 | 13.2 | Yes | 4 | ISG15 | 10.2 | Yes | 1 | STAT1 | 8.1 | Yes | 2 |
| DDX60L | 24.8 | Yes | 4 | KRT17 | 8.9 | Yes | 17 | TAP1 | 5.6 | Yes | 6 |
| DEFB1 | 4.5 | Yes | 8 | KYNU | 4.3 | Yes | 2 | TDRD12 | 12.3 | Yes | 19 |
| DHRS2 | 5.1 | Yes | 14 | LAMP3 | 7.1 | Yes | 3 | TFPI2 | 4.5 | Yes | 7 |
| DHX58 | 8.8 | Yes | 17 | LEPREL1 | 4.5 | Yes | 3 | TGFB1 | 4.0 | Yes | 19 |
| EPSTI1 | 7.1 | Yes | 13 | MMP13 | 6.2 | Yes | 11 | TNTL1 | 6.8 | Yes | 11 |
| F3 | 6.3 | Yes | 1 | MT1B | 7.1 | Yes | 16 | TNFAIP2 | 8.5 | Yes | 14 |
| FMLZ | 4.3 | Yes | 2 | MT1G | 5.8 | Yes | 16 | TRIM22 | 4.8 | Yes | 11 |
| FLJ13744 | 5.4 | | 8 | MT1H | 9.7 | Yes | 16 | UBD | 10.2 | Yes | 6 |
| FNR1KB | 6.8 | Yes | X | MT1X | 11.7 | Yes | 16 | UCA1 | 9.0 | Yes | 19 |
| PM1 | 9.7 | Yes | 2 | MT2A | 25.7 | Yes | 16 | USP18 | 20.5 | Yes | 22 |
| PSTL1 | 4.8 | Yes | 3 | MX1 | 8.2 | Yes | 21 | VCX | 12.2 | Yes | X |
| Q352 | 8.2 | Yes | 1 | MX2 | 9.4 | Yes | 21 | VCX2 | 19.7 | Yes | X |
| GTSF1 | 6.4 | Yes | 12 | NFE4 | 4.5 | Yes | | VCX3A | 8.5 | Yes | X |
| HGLS1 | 11.2 | Yes | 3 | NLRP2 | 7.5 | Yes | 19 | VCY | 6.3 | Yes | Y |
| HERC5 | 6.7 | Yes | 4 | OAS1 | 8.4 | Yes | 12 | XAF1 | 5.0 | Yes | 17 |
| HERC6 | 6.5 | Yes | 4 | OAS2 | 12.0 | Yes | 12 | XK | | Yes | X |
| HLA-C | 4.5 | Yes | 6 | OAS3 | 9.1 | Yes | 12 | ZBED2 | 4.8 | Yes | 3 |
| | | | | OASL | | | | | | | |

* 3.9 fold upregulated in H2170

Figure 26

| | Stress Response | Death Genes | KEGG Antigen Processing and Presentation | Immune Tolerance Regulation | Inflammasome | IRF7 Targets in H2170 | KEGG NFKB Pathway | KEGG Toll Like Receptor Signaling Pathway | KEGG RIG I Like Receptor Signaling Pathway |
|---|---|---|---|---|---|---|---|---|---|
| Stress Response | 23 | | | | | | | | |
| Death Genes | 1 | 50 | | | | | | | |
| KEGG Antigen Processing and Presentation | 0 | 1 | 48 | | | | | | |
| Immune Tolerance Regulation | 1 | 2 | 13 | 44 | | | | | |
| Inflammasome | 0 | 14 | 0 | 2 | 30 | | | | |
| IRF7 Targets in H2170 | 0 | 4 | 1 | 1 | 0 | 28 | | | |
| KEGG NFKB Pathway | 0 | 9 | 0 | 2 | 6 | 0 | 82 | | |
| KEGG Toll Like Receptor Signaling Pathway | 2 | 3 | 0 | 3 | 5 | 1 | 9 | 30 | |
| KEGG RIG I Like Receptor Signaling Pathway | 0 | 6 | 1 | 0 | 1 | 3 | 6 | 6 | 22 |

Figure 27A

| A549 | H1299 | H2170 | H358 | H460 | H838 | HCC4006 | HCC827 |
|---|---|---|---|---|---|---|---|
| AJAP1 | AKAP12 | AKAP12 | ADAM23 | ACTN2 | ALDH1A3 | | UBE2DNL |
| AKAP12 | ANKK1 | BIK | CACHD1 | AJAP1 | C1orf130 | | |
| ALDH1A3 | ANPEP | BNIP3 | CCK | AKAP12 | C2orf84 | | |
| AMPD3 | APH1B | CD38 | COL7A1 | AKR1E2 | CD248 | | |
| ANKK1 | BIK | CLDN23 | CRHR1 | ALDH1A3 | CDK5R1 | | |
| ANKRD53 | C20orf46 | COCH | CYB5R2 | ALPL | CPT1C | | |
| ANPEP | CLIC3 | DDX43 | DSE | APH1B | CYP11A1 | | |
| BIK | COL9A3 | EIF5A2 | ENG | AQP5 | DNALI1 | | |
| C5orf58 | DNALI1 | ELF4 | FBXO2 | ASPRV1 | EFHD1 | | |
| C9orf140 | FAM132A | FBXO2 | FZD7 | BMC1 | ELMO3 | | |
| C9orf4 | FERMT3 | FERMT3 | HLCJ | C20orf46 | ESRP2 | | |
| CCDC144NL | FMR1NB | FLNC | HIST1H2AD | C8orf84 | FAM50B | | |
| CCK | FZD7 | FMR1NB | HIST1H2AE | CAND2 | FES | | |
| CES1 | GDF15 | FSTL1 | HR | CAPS | GDF15 | | |
| CHTF18 | GPRC5B | FTHL17 | LIMS2 | CCDC144NL | HES5 | | |
| CLDN4 | HK1 | GATA3 | MES2 | CCND2 | HIST1H2BJ | | |
| CLIC3 | HK1 | HERC5 | MFI2 | CD248 | HSD17B8 | | |
| CLIC6 | HOXD13 | HLA-F | MS1 | CD38 | ICAM4 | | |
| COL9A3 | ICAM1 | HOXC9 | PCDHGA7 | COL9A3 | IFFO1 | | |
| CREB3L1 | ICAM4 | HSPA2 | PDLIM4 | COX7A1 | INA | | |
| CTCFL | ID4 | IFFO1 | PITX2 | CPT1C | IRF7 | | |
| CYB5R2 | IRF4 | IGF2BP1 | PLEK2 | CTCFL | IRX5 | | |
| DDX43 | LOC151534 | IRF7 | PTHLH | D4S234E | ISG15 | | |
| DNALI1 | LPIN3 | IRS1 | PTPRS | DBNDD2 | KLHDC7B | | |
| DPEP3 | LRFN4 | KLF14 | RGMA | DDX43 | LOC654433 | | |
| DUSP2 | LY6K | KLHDC7B | SDHAP3 | DKK3 | MAGE1 | | |
| ELL3 | MEST | LOC654433 | SGK1 | DNAJA4 | MEI1 | | |
| FAM20A | MFI2 | MARVELD1 | SLC16A1 | DNALI1 | MSTIR | | |
| FAM83H | PLD6 | MFI2 | TCF15 | DPEP3 | NEFH | | |
| FBLN2 | PLLP | MT1L | TNFRSF25 | DZIP1 | NES | | |
| FBXO2 | PP14571 | NES | TTTY14 | EHD3 | NTF3 | | |
| FERMT3 | S1PR4 | NKAPL | UCHL1 | ELF4 | POMC | | |
| FES | SLC4A11 | PCDHGA3 | | ELOVL2 | PRDX2 | | |
| FMR1NB | SPHMT2 | PLBD1 | | F2RL1 | PSMB8 | | |
| FRZB | TMEM204 | PLEK2 | | FABP5 | REC8 | | |
| FSTL1 | TRIM74 | PNLDC1 | | FAM118A | ROBO3 | | |
| FZD10 | TRPG | PPP1R14A | | FAM150B | S1PR4 | | |
| GATA3 | TYRO3 | REC8 | | FAM20A | SLC15A3 | | |
| GJB2 | VWCE | SCIN | | FAM3B | SOX15 | | |
| GPRASP1 | ZNF239 | SLC15A3 | | FAM50B | STAG3 | | |
| GSTM2 | | SLC16A5 | | FBLN2 | TDRD12 | | |
| H19 | | SDHLM2 | | FBXO2 | TMEM88 | | |
| HIST1H18 | | STOM | | FKBP16 | TNFRSF25 | | |
| HIST1H2AD | | TDRD12 | | FMR1NB | VAMP5 | | |
| HIST1H2AE | | TDRD9 | | FOXE1 | VWCE | | |
| HIST1H2BG | | TSPYL6 | | FRZB | WDR69 | | |
| HIST1H3D | | VWCE | | FZD10 | ZNF300 | | |
| HLA-F | | ZNF502 | | GALNT3 | | | |
| HOXA5 | | ZNF573 | | GCC1 | | | |

Figure 27B

| | A549 | H1299 | H2170 | H358 | H460 | H838 | HCC4006 | HCC827 |
|---|---|---|---|---|---|---|---|---|
| | HPD1 | | | | GDF15 | | | |
| | HRASLSS | | | | GFRA1 | | | |
| | HSPA2 | | | | GPC2 | | | |
| | ICAM1 | | | | GPX7 | | | |
| | IFFO1 | | | | H19 | | | |
| | INPPSD | | | | H19Q | | | |
| | IRF6 | | | | HS6ST1 | | | |
| | ISG15 | | | | HSPA2 | | | |
| | ISYNA1 | | | | ID4 | | | |
| | JAM3 | | | | IFFO1 | | | |
| | KANK4 | | | | INPPSD | | | |
| | LOC654433 | | | | IRF6 | | | |
| | LRFN4 | | | | IRF2 | | | |
| | LY6K | | | | IRX5 | | | |
| | MAGEB1 | | | | ISG15 | | | |
| | MEG3 | | | | ISYNA1 | | | |
| | MEIS2 | | | | KIAA1614 | | | |
| | MFI2 | | | | KLHDC7B | | | |
| | MST1P | | | | KRTZ | | | |
| | MX1 | | | | LITD1 | | | |
| | MYL9 | | | | LAYN | | | |
| | NAV1 | | | | LRRK1 | | | |
| | NEFH | | | | MAGEB1 | | | |
| | NEFM | | | | MEG3 | | | |
| | NINL | | | | MEST | | | |
| | NUDT11 | | | | MEX3A | | | |
| | PTX2 | | | | MFI2 | | | |
| | PLBD1 | | | | MT1M | | | |
| | PLEK2 | | | | MX1 | | | |
| | PLLP | | | | MYO5C | | | |
| | POU4F1 | | | | NAPRT1 | | | |
| | PRSS21 | | | | NEFH | | | |
| | RAB31 | | | | NINL | | | |
| | RBM46 | | | | NKAPL | | | |
| | REC8 | | | | PCDHGA2 | | | |
| | SEMA6C | | | | PCDHGA3 | | | |
| | SIPA1L3 | | | | PCSK9 | | | |
| | SLC12A8 | | | | PDIA2 | | | |
| | SLC4A11 | | | | PER3 | | | |
| | SPOCK2 | | | | PLAGL1 | | | |
| | ST3GAL2 | | | | PLBD1 | | | |
| | STAG3 | | | | PLEK2 | | | |
| | TCF15 | | | | PNLDC1 | | | |
| | TCF21 | | | | PNPLA3 | | | |
| | TDRD12 | | | | POMC | | | |
| | TDRD9 | | | | PTGER4 | | | |
| | TLX2 | | | | PTHLH | | | |
| | TMEM204 | | | | RASL11B | | | |
| | TMEM220 | | | | RFTN1 | | | |

Figure 27C

| A549 | H1299 | H2170 | H358 | H460 | H838 | HCC4006 | HCC827 |
|---|---|---|---|---|---|---|---|
| TNFRSF10C | | | | RGAG4 | | | |
| TNFRSF25 | | | | RGMA | | | |
| TNPO2 | | | | RIBC2 | | | |
| TRIM29 | | | | RIPK4 | | | |
| TRIM45 | | | | RPRM | | | |
| TRIM74 | | | | RUNX3 | | | |
| UBE2DNL | | | | SCRN1 | | | |
| VAMP5 | | | | SERP2 | | | |
| VWCE | | | | SFRP1 | | | |
| WDR69 | | | | SLC4A4 | | | |
| ZIK1 | | | | SLIT2 | | | |
| ZNF578 | | | | SOHLH2 | | | |
| ZNF75A | | | | SOX11 | | | |
| | | | | SPESP1 | | | |
| | | | | SPINT2 | | | |
| | | | | SPOCK2 | | | |
| | | | | SST | | | |
| | | | | STAG3 | | | |
| | | | | STK32B | | | |
| | | | | STOM | | | |
| | | | | TAC1 | | | |
| | | | | TCF15 | | | |
| | | | | TDRD12 | | | |
| | | | | TDRD9 | | | |
| | | | | TMEM171 | | | |
| | | | | TMEM88 | | | |
| | | | | TNFRSF10C | | | |
| | | | | TNFRSF25 | | | |
| | | | | TRIM45 | | | |
| | | | | TRIM74 | | | |
| | | | | TSPYL5 | | | |
| | | | | TSPYL6 | | | |
| | | | | VWCE | | | |
| | | | | ZNF167 | | | |
| | | | | ZNF300 | | | |
| | | | | ZNF331 | | | |
| | | | | ZNF502 | | | |
| | | | | ZSCAN18 | | | |

CANCER THERAPY VIA A COMBINATION OF EPIGENETIC MODULATION AND IMMUNE MODULATION

CROSS-REFERENCE TO RELATED APPLICATION

This application is a national stage application, filed under 35 U.S.C. § 371, of International Application No. PCT/US2014/054201, filed on Sep. 5, 2014, and claims priority to U.S. Provisional Patent Application Ser. No. 61/874,185, filed Sep. 5, 2013. The entire contents of, each of which are incorporated herein by reference in their entirety.

STATEMENT OF RIGHTS TO INVENTIONS MADE UNDER FEDERALLY SPONSORED RESEARCH

This invention was made with government support under grant CA058184 awarded by the National Institutes of Health. The government has certain rights in the invention.

FIELD OF THE INVENTION

The present invention relates to compounds, compositions, and methods for the study, diagnosis, and treatment of cancer and/or other proliferative diseases, disorders, or conditions. In certain embodiments, the invention specifically relates to combinations of therapies, including combination of epigenetic modulatory treatments with immunomodulatory therapies.

BACKGROUND OF THE INVENTION

Innovative strategies are needed to treat the world's most common cause of cancer death, non-small cell lung cancer (NSCLC).(1, 2) Less than a quarter of lung adenocarcinomas (LUAD) harbor genetic abnormalities for which targeted therapies have been derived. Early responses are often robust for these but are generally followed by acquired resistance.(3, 4) Lung squamous cell carcinoma (LUSC) has no approved targeted therapies and few effective chemotherapeutic options beyond the first line of therapy. Effective therapies for treatment of this highly lethal disease, as well as other forms of cancer and/or other proliferative diseases, disorders, or conditions, are urgently needed. In addition to the conventional forms of cancer therapy (chemotherapy, surgery, radiation), newer forms of therapy, including epigenetic modulation with DNA demethylating agents and HDAC inhibitors and therapies targeted at the immune system, are actively being investigated.

SUMMARY OF THE INVENTION

The present invention relates, at least in part, to the discovery that epigenetic modulation was observed to alter tumor gene expression so as to induce an immune signature. This discovery and the ability of demethylating agents to induce de novo expression of tumor-specific antigens, as well as a discovery that tumors induce immune checkpoint ligands to protect themselves from anti-tumor immune responses, led to the instant identification that a combination of epigenetic modulation and blockade of immune checkpoint pathways, such as the PD-1 pathway, could provide a synergistic anti-tumor response. Indeed, such identification was validated through observation of the clinical outcomes of advanced, chemotherapy refractory lung cancer patients treated with antibodies that block the PD-1 checkpoint pathway after the tumors of these subjects had progressed during epigenetic modulation. Three of five patients treated sequentially with epigenetic modulation followed by PD-1 pathway blockade developed objective clinical responses with dramatic tumor shrinkage. The other two patients developed stable disease lasting >6 months. These findings demonstrated an unexpected anti-neoplasia synergistic activity between epigenetic modulation and immune modulation.

In one aspect, the invention provides a method of treating or preventing a neoplastic condition in a subject in need thereof that involves administering (i) an epigenetic modulating agent combined with (ii) an immune modulating agent, such that the neoplastic condition in the subject is treated or prevented.

In one embodiment, the epigenetic modulating agent is administered before the immune modulating agent. Alternatively, the epigenetic modulating agent and the immune modulating agent are administered concurrently.

In one embodiment, the epigenetic modulating agent is a demethylating agent. In a related embodiment, the epigenetic modulating agent is a DNA methyl transferase (DNMT) inhibitor or a histone deacetylase (HDAC) inhibitor or a combination of DNMT inhibitor and an HDAC inhibitor. In certain embodiments, the epigenetic modulating agent is 5-azacytidine, 5-aza-2'-deoxycytidine (optionally, for subcutaneous administration), a dinucleotide containing 5-aza-CdR, Vorinostat, Romidepsin, Panobinostat or HDAC inhibitor CI-994. Optionally, the epigenetic modulating agent is 5-azadeoxycytidine.

In certain embodiments, the method further involves administering a MAC inhibitor.

In one embodiment, the immune modulating agent is an antibody (or fragment thereof), a compound, a recombinant molecule or an aptamer. In a related embodiment, the immune modulating agent is an anti-PD-1 antibody or an anti-PD-L1 antibody.

In certain embodiments, the immune modulating agent inhibits an immune checkpoint pathway. Optionally, the immune checkpoint pathway is a CTLA-4, LAG-3, B7-H3, B7-H4, Tim3, BTLA, KIR, A2aR, CD200 or PD-1 pathway.

In one embodiment, the immune modulating agent is a cancer vaccine. In certain related embodiments, the method further involves administering an agent that inhibits an immune checkpoint pathway.

In some embodiments, the immune modulating agent is an agonist for a co-stimulatory immune receptor. Optionally, the agonist is an antibody (or fragment thereof), a compound, a recombinant molecule or an aptamer. In certain related embodiments, the immune receptor is CD137, GITR, CD40, OX-40 or CD27.

In one embodiment, the neoplastic condition is lung cancer (optionally, NSCLC), colon cancer or ovarian cancer.

In certain embodiments, the neoplastic condition in the subject is stabilized. In related embodiments, the stabilization is for a duration of one month or more, two months or more, three months or more, four months or more, six months or more or eight months or more.

In another aspect, the invention provides a method for selectively inhibiting the growth of a cell that involves contacting a cell with an amount of (i) an epigenetic modulating agent and (ii) an immune modulating agent sufficient to inhibit the growth of the cell.

In one embodiment, the cell is a cancer cell of a subject.

In certain embodiments, the cancer cell is a lung cancer cell, an ovarian cancer cell or a colon cancer cell. Optionally, the lung cancer cell is a non-small cell lung cancer cell.

In some embodiments, the cell is a tumor cell of a subject. Optionally, the cell is a tumor cell in vitro. In certain embodiments, the cell is a human cell.

Another aspect of the invention provides a method for improving the anti-neoplastic effect of an immune modulating agent in a subject that involves administering an epigenetic modulating agent and the immune modulating agent to a subject, where the anti-neoplastic effect of the immune modulating agent in the subject is enhanced as compared to an appropriate control subject.

A further aspect of the invention provides a method of assessing the potential or realized anti-neoplastic effect of an epigenetic modulating agent and an immune modulating agent in a subject that involves measuring the expression of one or more genes of IRF7 and FIG. 25 as a biomarker for the potential or realized anti-neoplastic effect of the epigenetic modulating agent and the immune modulating agent in the subject.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "proliferative disease" or "cancer" as used herein is meant, a disease, condition, trait, genotype or phenotype characterized by unregulated cell growth or replication as is known in the art; including leukemias, for example, acute myelogenous leukemia (AML), chronic myelogenous leukemia (CML), acute lymphocytic leukemia (ALL), and chronic lymphocytic leukemia, AIDS related cancers such as Kaposi's sarcoma; breast cancers; bone cancers such as Osteosarcoma, Chondrosarcomas, Ewing's sarcoma, Fibrosarcomas, Giant cell tumors, Adamantinomas, and Chordomas; Brain cancers such as Meningiomas, Glioblastomas, Lower-Grade Astrocytomas, Oligodendrocytomas, Pituitary Tumors, Schwannomas, and Metastatic brain cancers; cancers of the head and neck including various lymphomas such as mantle cell lymphoma, non-Hodgkins lymphoma, adenoma, squamous cell carcinoma, laryngeal carcinoma, gallbladder and bile duct cancers, cancers of the retina such as retinoblastoma, cancers of the esophagus, gastric cancers, multiple myeloma, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, parotid adenocarcinoma, endometrial sarcoma, multidrug resistant cancers; and proliferative diseases and conditions, such as neovascularization associated with tumor angiogenesis, macular degeneration (e.g., wet/dry AMD), corneal neovascularization, diabetic retinopathy, neovascular glaucoma, myopic degeneration and other proliferative diseases and conditions such as restenosis and polycystic kidney disease, and other cancer or proliferative disease, condition, trait, genotype or phenotype that can respond to the modulation of disease related gene expression in a cell or tissue, alone or in combination with other therapies.

By "subject" is meant an organism, which is a donor or recipient of explanted cells or the cells themselves. "Subject" also refers to an organism to which the agents of the invention can be administered. A subject can be a mammal or mammalian cells, including a human or human cells.

As used herein, "neoplasia" means a disease state of a human or an animal in which there are cells and/or tissues which proliferate abnormally. Neoplastic conditions include, but are not limited to, cancers, sarcomas, tumors, leukemias, lymphomas, and the like. A neoplastic condition refers to the disease state associated with the neoplasia. Lung cancer, colon cancer and ovarian cancer are examples (non-limiting) of a neoplastic condition.

A "cancer" in a subject refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within a subject, or may be a non-tumorigenic cancer cell, such as a leukemia cell. Examples of cancer include but are not limited to breast cancer, a melanoma, adrenal gland cancer, biliary tract cancer, bladder cancer, brain or central nervous system cancer, bronchus cancer, blastoma, carcinoma, a chondrosarcoma, cancer of the oral cavity or pharynx, cervical cancer, colon cancer, colorectal cancer, esophageal cancer, gastrointestinal cancer, glioblastoma, hepatic carcinoma, hepatoma, kidney cancer, leukemia, liver cancer, lung cancer, lymphoma, non-small cell lung cancer, osteosarcoma, ovarian cancer, pancreas cancer, peripheral nervous system cancer, prostate cancer, sarcoma, salivary gland cancer, small bowel or appendix cancer, small-cell lung cancer, squamous cell cancer, stomach cancer, testis cancer, thyroid cancer, urinary bladder cancer, uterine or endometrial cancer, and vulval cancer.

As used herein, the term "tumor" means a mass of transformed cells that are characterized by neoplastic uncontrolled cell multiplication and at least in part, by containing angiogenic vasculature. The abnormal neoplastic cell growth is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, the term "epigenetic modulating agent" or "epigenetic drug" refers to an agent that alters the epigenetic state (e.g., methylation state) of the DNA of a cell upon or after contact with or administration of such agent. Examples of "epigenetic modulating agents" include DNA methyl transferase (DNMT) and histone deacetylase (HDAC)

inhibitors. In specific embodiments, an "epigenetic modulating agent" includes any or any combination of the following agents that have either been approved or are seeking approval from the US Food and Drug Administration (FDA). 5-azacytidine (5-aza-CR; manufactured by Celgene as Vidaza) was approved in 2004 specifically to inhibit DNA methylation, and two years later its variant 5-aza-2'-deoxycytidine (optionally, subcutaneous 5-azadeoxycytidine) was approved (5-aza-CdR; manufactured by Eisai as Dacogen). Both were approved for the treatment of higher-risk myelodysplastic syndrome. In addition, S110 (Ref. 110), which is a dinucleotide containing 5-aza-CdR and is suggested to have enhanced stability and efficiency, complements the list of DNMT inhibitors that are currently in use or that are being tested in clinical trials. Vorinostat (Merck)—an FDA-approved HDAC inhibitor for the treatment of cutaneous T cell lymphoma (CTCL)—was also confirmed to induce complete response or haematological improvement in AML patients. Besides Vorinostat, Romidepsin (Celgene), another HDAC inhibitor, revealed remarkable efficacies in the treatment of cutaneous T cell lymphoma (CTCL) patients. Two additional HDAC inhibitors—Panobinostat (Novartis) and CI-994 (Pfizer)—are being tested in clinical phase III trials for the treatment of lymphomas and non-small-cell lung cancer (NSCLC), respectively.

As used herein, the term "cancer therapy" refers to a therapy useful in treating cancer. Examples of anti-cancer therapeutic agents include, but are not limited to, e.g., surgery, chemotherapeutic agents, immunotherapy, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., HERCEPTIN®), anti-CD20 antibodies, an epidermal growth factor receptor (EGFR) antagonist (e.g., a tyrosine kinase inhibitor), HER1/EGFR inhibitor (e.g., erlotinib (TARCEVA®)), platelet derived growth factor inhibitors (e.g., GLEEVEC™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also contemplated for use with the methods described herein.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, Astrazeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, GlaxoSmithKline), Lonafarnib (SCH 66336), Sorafenib (BAY43-9006, Bayer Labs.), and Gefitinib (IRESSA®, Astrazeneca), AG1478, AG1571 (SU 5271; Sugen), alkylating agents such as Thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analogue topotecan); bryostatin; callystatin; CC-1065 (including its adozicsin, carzicsin and bizicsin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaI1 and calicheamicin omegaI1 (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacytidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; CPT-11; topoisomerase inhibitor RFS 2000; difluoromethylornithine (DMFO); retinoids such as retinoic acid; capecitabine; and pharmaceutically acceptable salts, acids or derivatives of any of the above.

Also included in this definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON-.toremifene; (ii) aromatase inhibitors that inhibit the enzyme aromatase, which regulates estrogen production in the adrenal glands, such as, for example, 4 (5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those which inhibit expression of genes in signaling pathways implicated in aberant cell proliferation, such as, for example, PKC-alpha, Ralf and H-Ras; (viii) ribozymes such as a VEGF expression inhibitor (e.g., ANGIOZYME® ribozyme) and a HER2 expression inhibitor; (ix) vaccines such as gene therapy vaccines, for example, ALLOVECTIN° vaccine, LEUVECTIN® vaccine, and VAXID® vaccine; PROLEUKIN® rIL-2; LURTOTECAN® topoisomerase 1 inhibitor; ABARELIX® rmRH; (x) anti-angiogenic agents such as bevacizumab (AVASTIN®, Genentech); and (xi) pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (e.g., vincristine and vinblastine), taxanes, and topoisomerase II inhibitors such as doxorubicin, epirubicin, daunorubicin, etoposide, and bleomycin. The agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

In one embodiment, as used herein, the term "treat' or treatment" refers to reducing or alleviating at least one adverse clinical symptom associated with cancer, e.g., pain, swelling, low blood count etc. In another embodiment, the term "treat' or treatment" refers to slowing or reversing the progression neoplastic uncontrolled cell multiplication, i.e. shrinking existing tumors and/or halting tumor growth. In another embodiment, the term "treat' or treatment" refers to inducing apoptosis in cancer or tumor cells in the subject.

As used herein, the term "a therapeutically effective amount" refers to an amount sufficient to achieve the intended purpose of treating cancer. In one embodiment, a therapeutically effective amount of an epigenetic modulatory agent and/or an immunomodulatory agent described herein for a method of treating cancer is an amount of sufficient to induce apoptosis of cancer cells of the subject as compared to in the absence of one or both such agents. In other embodiments, the amount(s) that is safe and sufficient to treat, delay the development of a tumor, and/or delay further growth of the tumor. In some embodiments, the amount can thus cure or result in amelioration of the symptoms of cancer and tumor growth, slow the course of cancer progression, slow or inhibit a symptom of cancer, slow or inhibit the establishment of secondary symptoms of cancer or inhibit the development of a secondary symptom of the cancer. For example, an effective amount of an epigenetic modulatory agent and/or an immunomodulatory agent described herein can inhibit further tumor growth, cause a reduction in size or even completely halt tumor growth, shrink the sizes of tumor, even complete regression of tumor, and reduce clinical symptoms associated with tumor. In certain embodiments, an effective amount for treating cancer is an amount of an epigenetic modulatory agent and/or an immunomodulatory agent described herein sufficient to result in a reduction or complete removal of the symptoms of the disorder, disease, or medical condition. In some embodiments, an effective amount for treating or ameliorating a disorder, disease, or medical condition is an amount sufficient to result in a reduction or complete removal of the symptoms of the disorder, disease, or medical condition. In certain embodiments, a "therapeutically effective amount of an antibody" refers to an amount of an antibody, antibody fragment, or derivative, e.g., multispecific antibody or antibody analog, to treat a disease or disorder in a subject. In the case of tumor (e.g., a cancerous tumor), the therapeutically effective amount of the antibody or antibody fragment (e.g., a multispecific antibody or antibody analog) may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment (e.g., multispecific antibody or antibody analog) may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life. The effective amount of a given therapeutic agent will vary with factors such as the nature of the agent, the route of administration, the size and species of the animal to receive the therapeutic agent, and the purpose of the administration. Thus, it is not possible or prudent to specify an exact "therapeutically effective amount". However, for any given case, an appropriate "effective amount" can be determined by a skilled artisan according to established methods in the art using only routine experimentation.

By "reduce or inhibit" is meant the ability to cause an overall decrease of 20% or greater, or 50% or greater, or 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The phrase "pharmaceutically acceptable carrier" refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Various methodologies of the instant invention include a step that involves comparing a value, level, feature, characteristic, property, etc. to a "suitable control", referred to interchangeably herein as an "appropriate control". A "suitable control" or "appropriate control" is a control or standard familiar to one of ordinary skill in the art useful for comparison purposes. In one embodiment, a "suitable control" or "appropriate control" is a value, level, feature, characteristic, property, etc. determined prior to performing a treatment and/or agent administration methodology, as described herein. For example, a transcription rate, mRNA level, translation rate, protein level, biological activity, cellular characteristic or property, genotype, phenotype, etc. can be determined prior to introducing a treatment and/or agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

The term "in vitro" has its art recognized meaning, e.g., involving purified reagents or extracts, e.g., cell extracts. The term "in vivo" also has its art recognized meaning, e.g., involving living cells, e.g., immortalized cells, primary cells, cell lines, and/or cells in an organism.

"Treatment", or "treating" as used herein, is defined as the application or administration of a therapeutic agent or combination of therapeutic agents (e.g., an epigenetic therapy agent and/or an immunomodulatory therapy agent) to a patient, or application or administration of a therapeutic agent to an isolated tissue or cell line from a patient, who has a disorder with the purpose to cure, heal, alleviate, relieve, alter, remedy, ameliorate, improve or affect the disease or disorder, or symptoms of the disease or disorder. The term "treatment" or "treating" is also used herein in the context of administering agents prophylactically. The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. The term "patient" includes human and other mammalian subjects that receive either prophylactic or therapeutic treatment.

As used herein, a "tissue sample" refers to a portion, piece, part, segment, or fraction of a tissue which is obtained or removed from an intact tissue of a subject, preferably a human subject. In one embodiment, the tissue sample is a lung sample. In another embodiment, the tissue sample is a blood sample. In one embodiment, the tissue sample is a breast or colon sample.

As used herein, a "tumor sample" refers to a portion, piece, part, segment, or fraction of a tumor, for example, a tumor which is obtained or removed from a subject (e.g., removed or extracted from a tissue of a subject), preferably a human subject.

In one embodiment, the tissue sample is obtained from a biopsy procedure in the subject. In another embodiment, the tissue sample is obtained from a surgical procedure to remove a tumor mass from the subject.

A "vaccine" is to be understood as meaning a composition for generating immunity for the prophylaxis and/or treatment of diseases (e.g., neoplasia/tumor). Accordingly, vaccines are medicaments which comprise antigens and are intended to be used in humans or animals for generating specific defense and protective substance by vaccination.

A "MAC inhibitor" is an inhibitor of the formation and/or activity of complement membrane attack complex (MAC). In certain embodiments, a "MAC inhibitor" is anti-CD59 antibody, which acts by binding to the C8 and/or C9 complements of the assembling MAC, thereby preventing incorporation of the multiple copies of C9 required for complete formation of the osmolytic pore.

A "cancer vaccine," as used herein is a composition that stimulates an immune response in a subject against a cancer. Cancer vaccines typically consist of a source of cancer-associated material or cells (antigen) that may be autologous (from self) or allogenic (from others) to the subject, along with other components (e.g., adjuvants) to further stimulate and boost the immune response against the antigen. Cancer vaccines can result in stimulating the immune system of the subject to produce antibodies to one or several specific antigens, and/or to produce killer T cells to attack cancer cells that have those antigens.

As used herein, an "immune modulating agent" is an agent capable of altering the immune response of a subject. In certain embodiments, "immune modulating agents" include adjuvants (substances that enhance the body's immune response to an antigen), vaccines (e.g., cancer vaccines), and those agents capable of altering the function of immune checkpoints, including the CTLA-4, LAG-3, B7-H3, B7-H4, Tim3, BTLA, KIR, A2aR, CD200 and/or PD-1 pathways. Exemplary immune checkpoint modulating agents include anti-CTLA-4 antibody (e.g., ipilimumab), anti-LAG-3 antibody, anti-B7-H3 antibody, anti-B7-H4 antibody, anti-Tim3 antibody, anti-BTLA antibody, anti-KIR antibody, anti-A2aR antibody, anti CD200 antibody, anti-PD-1 antibody, anti-PD-L1 antibody, anti-CD28 antibody, anti-CD80 or -CD86 antibody, anti-B7RP1 antibody, anti-B7-H3 antibody, anti-HVEM antibody, anti-CD137 or -CD137L antibody, anti-OX40 or -OX40L antibody, anti-CD40 or -CD40L antibody, anti-GAL9 antibody, anti-IL-10 antibody and A2aR drug. For certain such immune pathway gene products, the use of either antagonists or agonists of such gene products is contemplated, as are small molecule modulators of such gene products. In certain embodiments, the "immune modulatory agent" is an anti-PD-1 or anti-PD-L1 antibody.

As used herein, a "recombinant molecule" refers to an expression vector harboring a DNA insert. In certain embodiments, the "recombinant molecule" is designed to express an immune modulating agent.

As used herein, the term "administer continuously," in the context of administration of a therapy to a subject, refers to the administration of a therapy to a subject at a frequency that is expected to maintain a specific plasma concentration of the therapy. For instance, in some embodiments of the therapies that are administered continuously, the administration to the subject is at a frequency that is expected to maintain less than a 50% change in the plasma concentration of the therapy, e.g., a 20-50% change, a 10-30% change, a 5-25% change, or a 1-20% change in plasma concentration of the therapy.

As used herein, the term "agent" refers to any molecule, compound, nucleic acid, nucleic acid based moiety, antibody, antibody-based molecule, protein, protein-based molecule and/or substance for use in the prevention, treatment, management and/or diagnosis of cancer.

As used herein, the term "cancer cells" refer to cells that acquire a characteristic set of functional capabilities during their development, including the ability to evade apoptosis, self-sufficiency in growth signals, insensitivity to anti-growth signals, tissue invasion/metastasis, significant growth potential, and/or sustained angiogenesis. The term "cancer cell" is meant to encompass both pre-malignant and malignant cancer cells.

As used herein, the term "compound" refers to small molecules. Examples of such small molecules would include low molecular weight molecules. Other examples of compounds include molecules that are generated by organic synthesis, and low molecular weight molecules that are metabolites or anti-metabolites. In one embodiment, compounds can be administered directly to patients, or can be conjugated to antibodies or protein-based agents. In another embodiment, compounds can be administered in combination with other agents. In a specific embodiment, the agent administered in combination with a compound is an antibody or antibody-based therapeutic.

As used herein, the term "effective amount" refers to the amount of a therapy that is sufficient to result in therapeutic benefit to a patient with cancer, In one embodiment, the cancer patient has been diagnosed with NSCLC. In one embodiment, the effective amount is administered to a patient that has been diagnosed with cancer. The effective amount can result in the prevention of the development, recurrence, or onset of cancer and one or more symptoms thereof, to enhance or improve the efficacy of another therapy, reduce the severity, the duration of cancer, ameliorate one or more symptoms of cancer, prevent the advancement of cancer, cause regression of cancer, and/or enhance or improve the therapeutic effect(s) of another therapy. "Effective amount" also refers to the amount of a therapy that is sufficient to result in the prevention of the development, recurrence, or onset of cancer and one or more symptoms thereof, to enhance or improve the prophylactic effect(s) of another therapy, reduce the severity, the duration of cancer, ameliorate one or more symptoms of cancer, prevent the advancement of cancer, cause regression of cancer, and/or enhance or improve the therapeutic effect(s) of another therapy. In an embodiment of the invention, the amount of a therapy is effective to achieve one, two, three, or more results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate, (10) a decrease in hospitalization lengths, (11) the size of the tumor is maintained and does not increase or increases by less than 10%, preferably less than 5%, preferably less than 4%, preferably less than 2%, (12) an increase in the number of patients in remission, (13) an increase in the length or duration of remission, (14) a decrease in the recurrence rate of cancer, (15) an increase in the time to recurrence of cancer, and (16) an amelioration of cancer-related symptoms and/or quality of life.

As used herein, the term "in combination" in the context of the administration of a therapy to a subject refers to the use of more than one therapy for therapeutic benefit. The term "in combination" in the context of the administration can also refer to the prophylactic use of a therapy to a subject when used with at least one additional therapy. The use of the term "in combination" does not restrict the order in which the therapies (e.g., a first and second therapy) are administered to a subject. A therapy can be administered prior to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 1 minute, 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject which had, has, or is susceptible to cancer. The therapies are administered to a subject in a sequence and within a time interval such that the therapies can act together. In a particular embodiment, the therapies are administered to a subject in a sequence and within a time interval such that they provide an increased benefit than if they were administered otherwise. Any additional therapy can be administered in any order with the other additional therapy.

As used herein, the term "antibody" refers to a protein that includes at least one immunoglobulin variable region, e.g., an amino acid sequence that provides an immunoglobulin variable domain or an immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab fragments, F(ab')2 fragments, Fd fragments, Fv fragments, and dAb fragments) as well as complete antibodies, e.g., intact and/or full length immunoglobulins of types IgA, IgG (e.g., IgG1, IgG2, IgG3, IgG4), IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity, or may be non-functional for one or both of these activities.

The VH and VL regions can be further subdivided into regions of hypervariability, termed "complementarity determining regions" ("CDR"), interspersed with regions that are more conserved, termed "framework regions" (FR). The extent of the FR's and CDR's has been precisely defined (see, Kabat, E. A. et al. (1991) Sequences of Proteins of Immunological Interest, Fifth Edition, U.S. Department of Health and Human Services, NIH Publication No. 91-3242; and Chothia. C. et al (1987) J. Mol. Biol. 196:901-917). Kabat definitions are used herein. Each VH and VL is typically composed of three CDR's and four FR's, arranged from amino-terminus to carboxyl-terminus in the following order: FR1, CDR1, FR2, CDR2, FR3, CDR3, FR4.

An "immunoglobulin domain" refers to a domain from the variable or constant domain of immunoglobulin molecules Immunoglobulin domains typically contain two β-sheets formed of about seven β-strands, and a conserved disulphide bond (see, e.g., A. F. Williams and A. N. Barclay (1988) Ann Rev. Immunol. 6:381-405). An "immunoglobulin variable domain sequence" refers to an amino acid sequence that can form a structure sufficient to position CDR sequences in a conformation suitable for antigen binding. For example, the sequence may include all or part of the amino acid sequence of a naturally-occurring variable domain. For example, the sequence may omit one, two, or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with TWEAK or a TWEAK receptor.

The VH or VL chain of the antibody can further include all or part of a heavy or light chain constant region, to thereby form a heavy immunoglobulin chain (HC) or light immunoglobulin chain (LC), respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2, and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

One or more regions of an antibody can be human, effectively human, or humanized. For example, one or more of the variable regions can be human or effectively human. For example, one or more of the CDRs, e.g., HC CDR1, EC CDR2, HC CDR3, LC CDR1, LC CDR2, and LC CDR3, can be human. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins, or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical, or completely identical, to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. Nos. 6,407,213 and 5,693,762. In some cases, humanized immunoglobulins can include a non-human amino acid at one or more framework amino acid positions.

The terms "synergy," "synergistic," or "synergistic effect" as used herein describe an effect which has a magnitude that is greater than additive. In some embodiments of the present invention, the use of both an epigenetic modulating agent and an immune modulating agent in concert provides synergistic therapeutic effect on a neoplastic condition in a subject and/or on the growth of a cell. For example, if use of an epigenetic modulating agent produced a 10% reduction in neoplastic growth and use of an immune modulating agent alone produced a 20% reduction in neoplastic growth, then the additive effect for reducing neoplastic growth would be 30% reduction. Hence, by comparison, a synergistic effect when using both the epigenetic modulating agent and the immune modulating agent in concert would be reduction in neoplastic growth to any extent greater than 30% reduction.

As used herein, the term "marker" in the context of a cell or tissue (e.g. a normal or cancer cell or tumor) means any antigen, molecule or other chemical or biological entity that is specifically found in or on a tissue that it is desired to identified or identified in or on a particular tissue affected by a disease or disorder. In specific embodiments, the marker is a cell surface antigen that is differentially or preferentially expressed by specific cell types. For example, a leukemia cancer stem cell differentially expresses CD123 relative to a normal hematopoietic stem cell.

As used herein, the terms "prevent," "preventing" and "prevention" in the context of the administration of a therapy to a subject refer to the prevention or inhibition of the recurrence, onset, and/or development of a cancer or a symptom thereof in a subject resulting from the administration of a therapy (e.g., a prophylactic agent), or a combination of therapies (e.g., a combination of prophylactic agents). In some embodiments, such terms refer to one, two, three, or more results following the administration of one or more therapies: (1) a stabilization, reduction or elimination in the cancer cell population, (2) an increase in response rate, (3) an increase in the length or duration of remission, (4) a decrease in the recurrence rate of cancer, (5) an increase in the time to recurrence of cancer, (6) an increase in the disease-free, relapse-free, progression-free, and/or overall survival of the patient, and (7) an amelioration of cancer-related symptoms and/or quality of life. In specific embodiments, such terms refer to a stabilization, reduction or elimination of the cancer stem cell population.

As used herein, the term "therapeutically effective regimen" refers to a regimen for dosing, timing, frequency, and duration of the administration of one or more therapies for the treatment and/or management of cancer or a symptom thereof. In a specific embodiment, the regimen achieves one, two, three, or more of the following results: (1) a stabilization, reduction or elimination in the cancer cell population; (2) a stabilization or reduction in the growth of a tumor or neoplasm; (3) an impairment in the formation of a tumor; (4) eradication, removal, or control of primary, regional and/or metastatic cancer; (5) a reduction in mortality; (6) an increase in disease-free, relapse-free, progression-free, and/or overall survival, duration, or rate; (7) an increase in the response rate, the durability of response, or number of patients who respond or are in remission; (8) a decrease in hospitalization rate, (9) a decrease in hospitalization lengths, (10) the size of the tumor is maintained and does not increase or increases by less than 10%, preferably less than 5%, preferably less than 4%, preferably less than 2%, and (11) a increase in the number of patients in remission. Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. Concentrations, amounts, cell counts, percentages and other numerical values may be presented herein in a range format. It is to be understood that such range format is used merely for convenience and brevity and should be interpreted flexibly to include not only the numerical values explicitly recited as the limits of the range but also to include all the individual numerical values or sub-ranges encompassed within that range as if each numerical value and sub-range is explicitly recited.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

BRIEF DESCRIPTION OF THE DRAWINGS

FIG. 2 lists genes for which azacytidine (AZA) treatment was observed to provoke pro-inflammatory changes in gene expression, within cell lines as indicated.

FIGS. 16A-J shows a heat map and histograms showing that azacytidine alters gene expression in NSCLC cell lines for multiple immune related pathways. FIG. 16A top panel depicts Gene Set Enrichment Analysis (GSEA) for pathways up-regulated by azacytidine. Normalized enrichment scores were plotted as a heat map. Meanwhile, FIG. 16A bottom panel depicts a boxplot showing degrees of demethylation in each cell line, as measured by the difference in beta values between the AZA and mock-treated cells immediately after drug withdrawal and 7 days later. FIG. 16B shows a FACS analysis that demonstrated increased level of cell surface PD-L1 after AZA treatment by day 10 in NSCLC lines H838 and H1299. FIGS. 16C to 16J show AZA-mediated expression changes, at day 10, in key genes from pathways outlined in FIG. 16A. Y axis=Ratio of expression values (Log 2) of AZA-treated vs. mock-treated cells; X-axis=the individual genes.

FIG. 18 shows, in the left panel, the identification of genes in Non-Small Cell Lung Cancer cell lines with low basal expression and high basal promoter region DNA methylation which are demethylated and reexpressed with AZA treatment. The red box encompasses genes meeting these criteria which are described specifically herein. Among these, IRF7, a key immune-related transcription factor, was up-regulated in multiple cell lines. The histogram of FIG. 18 demonstrates that pathways up-regulated in NSCLC cell lines in response to AZA were enriched for IRF7 targets as determined by PScan analysis (-log 10 of pvalues) and gene set enrichment analysis. FIG. 19 shows a heat map of RNA-Seq expression levels in primary lung cancers from TCGA database for genes 4-fold or more induced by AZA in the LUSC cell line H2170, the cell line with the greatest degree of IRF7 up-regulation. Top bar: red indicates LUAD and orange indicates LUSC samples. Genes used in the heat map are listed in FIG. 25. FIG. 20 depicts bar panels that show expression of PD-L1 and IRF7 in five quantile intervals (red for lower and green for higher expression). The heat map immediately below the IRF7 expression bar shows corresponding Infinium platform DNA methylation levels (Z-scores, red for more and green for less methylated) across the promoter region. Positions relative to the transcription start site are shown at right. CpG-island probes are labeled in green. Sample order in bar plots and methylation heat map was maintained from the main heat map.

FIGS. 23A-B depict outcomes for five patients treated with immune checkpoint immunotherapy after epigenetic therapy. FIG. 23A shows scans for 3 patients (Pt.) with RECIST criteria responses to either PD-1 or PD-L1 therapy. All scan interpretations were performed by a single radiologist and lesions shown to measure tumor shrinkage between pre- and during immunotherapy at specified times are shown by red arrows (metastasis in the spleen—Pt. 1; lung tumor lesions—Pt. 2; lymph node in right central chest with metastases—Pt. 2. Green arrow denotes large area of the right lung collapsed behind airway obstruction by tumor and resolving by the 10 month period after immunotherapy. FIG. 23B shows plots of sequential scan measurements (Y-axis) of lesions shown in panel (A) by weeks (X-axis) with a decrease of 30% qualifying as RECIST criteria response (green circles). Blue crosses indicate tumor increase of >20% qualifying as disease progression. The 24 weeks point denoted by the dashed vertical line represents a time point, in the national trials, by which 80% of the NSCLC patients who received the immunotherapy without prior epigenetic therapy had manifested progressive disease. Patient data for 5 patients treated with combination epigenetic therapy consisting of AZA and Entinostat prior to single agent anti-PD-1 or anti-PD-L1 directed immune-checkpoint blockade is also shown.

FIG. 24 shows a comparison of Agilent expression array data to flow cytometry for select cell surface proteins in human NSCLC cell line H838. Clear bars represent the log 2 ratio of mean fluorescence intensity of AZA over mock treated cells. Hashed bars represent the M-values of expression array (log 2[AZA:Mock]). For HLA Class I, the antibody used in flow cytometry did not discriminate subtypes of class I molecules. Individual class I molecule subtype transcript data are available from the Agilent array platform and are presented.

FIG. 25 shows genes that were identified as 4-fold or more up-regulated in H2170 at day 10 (7 days post AZA withdrawal). Gene symbols are indicated in the first column of each panel, the fold changes of the gene expression levels by AZA at day 10 in H2170 are in the second column, availability of RNA-Seq expression data is indicated in column 3, and the chromosomes on which the genes reside are indicated in column 4. Only genes that reside on autosomes and have available TCGA RNA-Seq data were used to plot FIG. 19.

FIG. 26 shows the overlaps of genes from each pathway represented in the heat maps. That the observed clustering pattern is not due to chance or batch effect was demonstrated via parallel assessment of random sets of 25 genes, shown in the bottom two panels of FIG. 22.

FIGS. 27A-C show a complete list of genes that were re-expressed for 0.5-fold or more (log 2 scale), promoter region CpG island hypermethylated in mock treated cell, and demethylated for greater than 25% by AZA in the eight NSCLC lines—identified transcription factors are labeled in red, while genes identified by the interferome database are underlined.

DETAILED DESCRIPTION OF THE INVENTION

The present invention relates, at least in part, to the unexpected observation that epigenetic modulatory therapy could greatly improve the responsiveness of a neoplastic subject to administration of an immune modulatory therapy. In support of this discovery, specific therapies were demonstrated to exert such an effect on NSCLC in patients, including combinations of the epigenetic modulating agent 5-deoxyazacytidine with either of the immune modulating agents anti-PD-1 antibody or anti-PD-L1 antibody. In addition, the expression levels of IRF7 and a related group of target genes initially assembled through expression profiling, were discovered to be predictive of the responsiveness of a neoplastic cell to combination therapies involving administration of both an epigenetic modulating agent and an immune modulating agent.

Innovative therapies are for advanced, Non-Small Cell Lung Cancer (NSCLC). A genomics based, hypothesis driving approach was undertaken to query the surprising potential that epigenetic therapy may sensitize to immune checkpoint therapy targeting PDL1/PD-1 interaction for this disease.

A small group of patients with advanced NSCLC treated with experimental epigenetic therapy were treated in a separate, subsequent clinical trial with immune checkpoint therapy, designed to break intra-tumoral immune resistance and were observed to have a high rate of clinical benefit. Additional studies described herein have derived a genomics based, hypothesis driving, gene signature for response of NSCLC cells to a key constituent of the epigenetic therapy, which maps as an immune evasion signature in primary NSCLC. These results allowed for better understanding of epigenetic therapy as a priming strategy for immune checkpoint therapy in patients with NSCLC and also provided a biomarker strategy that is being tested in an initiated trial.

Figure 23B:
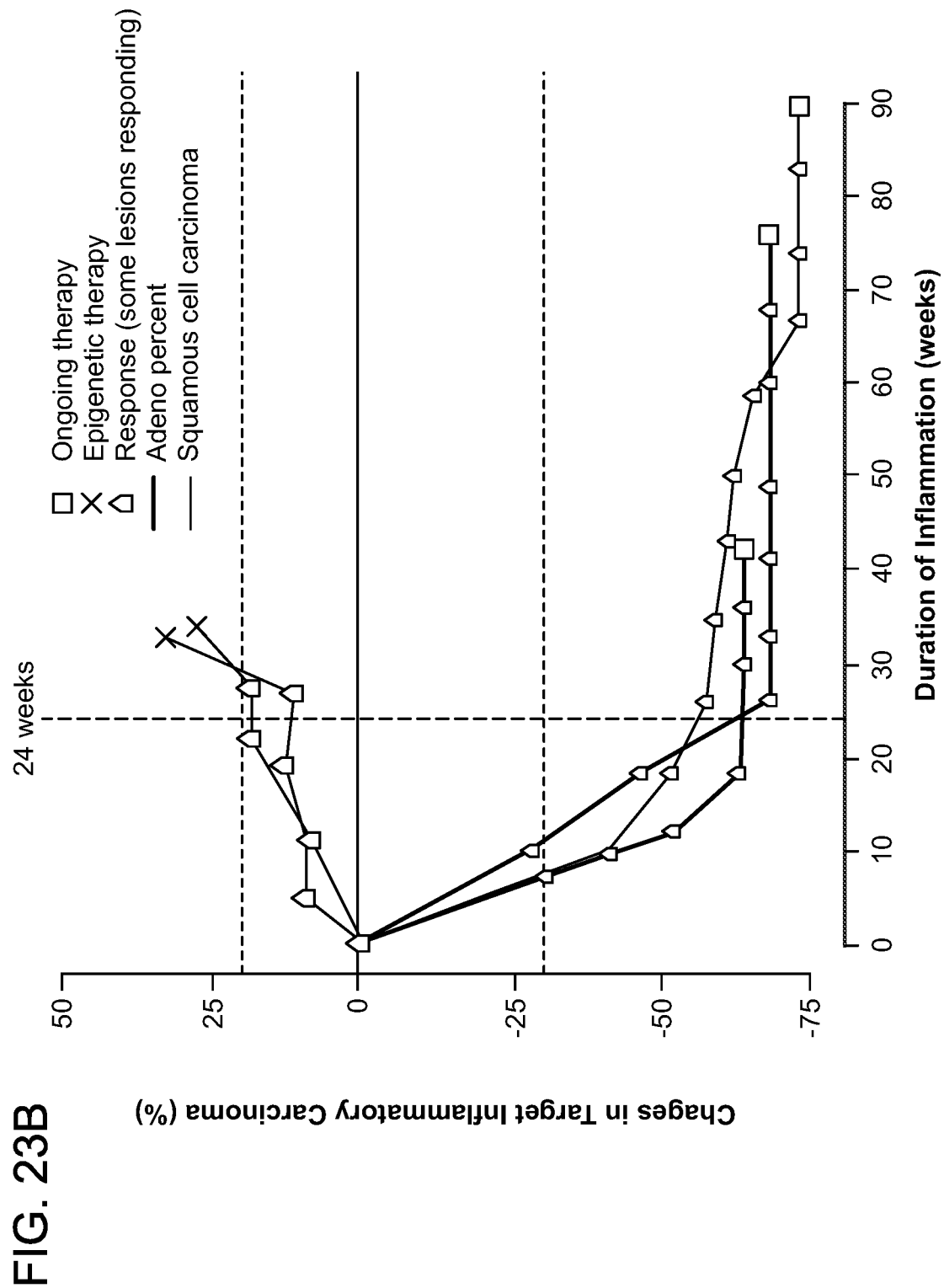

In studies described herein, a genomically based hypothesis-driving analysis has been employed to suggest a rationale for a novel combinatorial therapeutic approach to efficacious treatments for advanced NSCLC. The backdrop for these studies derives from initial clinical trials, in a Stand up to Cancer Project (SU2C, in which patients with advanced, heavily pre-treated NSCLC received a form of "epigenetic therapy" that combined low doses of the DNA hypomethylating agent azacytidine (AZA-Vidaza) and the HDAC inhibitor entinostat.(5) Only two of the now 65 patients treated to date have had RECIST criteria responses to this therapy alone, but such responses were very robust and durable.(5) A group of patients followed for 8 to 26 months responded to multiple different therapeutic regimens given subsequently, suggesting a "priming effect" of epigenetic therapy. Twenty-five percent of these patients with both LUAD and LUSC experienced RECIST criteria responses to their subsequent regimens. (FIG. 23) These subsequent therapies included not only standard chemotherapies but also immunotherapy targeting the PD-1 immune-checkpoint which when given alone had yielded responses in 16 to 17% of patients with advanced NSCLC. (6-8) While the number of patients who received epigenetic therapy followed by immune checkpoint blockade was small, a clinical trial to evaluate potential sensitization to PD-1 immune checkpoint blockade with epigenetic therapy in patients with NSCLC has now begun.

One of the key therapy agents being employed in the trial is azacytidine (AZA-Vidaza from Celgene). This nucleotide analog is a DNA demethylating agent which blocks the activity of all three biologically active DNA methyltransferases (DNMT's) and also triggers degradation of these proteins in the nucleus.(9, 10) With respect to sensitization potential of this drug for immune responses, such targeting of DNMT's has been observed to induce increased expression of promoter, DNA hypermethylated cancer testes antigens and also has been reported to up-regulate other individual facets of the tumor immune stimulating profile, including major histocompatibility antigens, and transcription factors IRF7 and IRF5.(11-16) In this regard, it was previously reported that elements of such immune pathway activation were produced by low doses of DNA demethylating agents in a genomics based, pre-clinical approach.(49) These studies demonstrated how low doses of AZA, which avoid early, cytotoxic and off-target effects, can provide a memory for a "reprogramming"-like effect on hematopoietic and selected examples of solid tumor cells.(17) It was thought that these effects might underlie the fact that significantly lowering doses of DNMT inhibitors in the clinic could account for the markedly decreased toxicity, and significant clinical efficacy, which has led to FDA approval of AZA for myelodysplasia (MDS).(18)

Initially, the pre-clinical approach was focused upon low dose AZA and its effect on NSCLC. By first deriving genomic signatures of gene expression responses and DNA methylation for treated NSCLC lines, a complex, multi-faceted up-regulation, involving hundreds of genes, of the immune profile was observed in most cell lines, which includes the target of immune checkpoint therapy, the tumor ligand, PD-L1. Moreover, using this extensive genomic signature, hundreds of primary NSCLC samples in the Cancer Genome Atlas project (TCGA) have been queried for how basal expression of these immune genes and related DNA methylation events group lung cancers. A stark clustering of subsets of primary LUAD and LUSC allowed for definition of an "immune evasion" signature which relates highly to events for low interferon pathway signaling and includes low levels of PD-L1.(19-21) Low expression of these genes closely matched those up-regulated by AZA treatment of the NSCLC cell lines. It is believed that these are the cancers which would benefit from AZA priming together with immune checkpoint therapy and that this work outlines a signature that can identify predictive biomarkers from biopsies forthcoming in the current trial.

In the present work, an in vitro model was used to derive a pre-clinical understanding of the immunomodulatory effects of clinically relevant doses of azacytidine in NSCLC that may underpin its potential to "prime" for subsequent response to PD-1 pathway blockade. An AZA induced expression signature of immune genes and pathways in NSCLC known to play a role in the down-regulation of immune surveillance of cancer was identified. However, concomitant with induction of the immune genes comprising both innate and adaptive immunity was the upregulation of a primary immune inhibitory ligand, PD-L1. These data therefore suggested a mechanism by which epigenetic therapy could improve the outcome of treatment of patients with NSCLC with PD-1/PD-L1 immune checkpoint blockade. By matching these basal gene expression and DNA methylation patterns, including that of a core interferon pathway transcription factor, IRF7 in the TCGA project, an in vitro AZA-induced gene signature was extrapolated to hundreds of primary NSCLC cancers. These results suggested that a major effect of AZA treatment is the alteration of tumor immune inducing pathways, that could lead to susceptibility of tumor cells themselves to immune attack by T cells. In particular, because the inhibitory ligand PD-L1 was up-regulated by AZA in tested cell lines, and subsets of primary tumors were observed to have concordant low-expression of AZA induced immune genes and PD-L1, the combination of epigenetic therapy and PD-1 pathway was newly identified as a proposed means of producing a synergistic antitumor response.

These findings provide a basis for biomarker approaches that are being tested in a new trial for patients with advanced LUAD and LUSC, aimed at validating the promise for sensitization by epigenetic therapy to immune checkpoint therapy. If robust patient efficacy continues to be seen, these data may also prove key to determining which individuals are likely to benefit from the epigenetic therapy approaches currently being tested in clinical trials by evaluating gene panels for expression and DNA methylation in pre- and post-drug administration biopsies.

Aberrant DNA methylation and histone deacetylation represent two of the critical mechanisms of tumor-specific gene silencing. Both of these critical mechanisms of epigenetic silencing can be reversed, using DNA methyltransferase inhibitors (such as azacytidine) and histone deacetylase inhibitors (such as entinostat). The biology and therapeutic implications of epigenetic gene silencing in cancer have been examined, with such efforts including demonstration of synergistic re-expression of silenced tumor suppressor genes when epigenetic gene silencing classes of drugs have been used (Juergens et al. *Cancer Discovery* 2011: 598-607; Cameron et al. *Nat Genet* 1999, 21: 103-7).

Beyond cell-autonomous effects, a combination of published and unpublished data has offered three non-mutually exclusive mechanisms by which epigenetic modulation of tumors can enhance anti-tumor immunity. First, epigenetic modulation induces a vast array of new antigens by the tumor, that are potential targets for T cell and antibody responses. Second, re-expression is induced at silenced promoters of key cytokine genes in T cells, such as interferon-gamma and IL-2—critical effector cytokines in anti-tumor responses (Gamper et al. *J Immunol.* 2009 183(4): 2267-76). Third, our recent discoveries profiling gene expression affects of global demethylation of DNA in tumor cells demonstrated induction of a "pathogen response" pattern of gene expression, characterized in part by a type I interferon response. Examples of immunologic genes that are induced by pharmacologic demethylation of DNA by treatment of tumor cell lines in vitro include IRF7, a major driver of the interferon pathway, certain Toll-like receptors, cytoplasmic sensors of DNA such as IFI27, inflammatory cytokines and interferon induced genes such as OAS1 and HLA-A. Thus, epigenetic modulation in patients with cancer might be predicted to induce anti-tumor immune responses.

The generation of anti-tumor responses leads to immune cell infiltration into tumors, which in turn induces the expression of immune inhibitory ligands—notably PD-1 ligands—by tumor cells and other cells in the tumor microenvironment. This "adaptive immune resistance" mechanism foils the immune response from killing the tumor. However, an immune-inducing maneuver with an antibody that blocks the PD-1 inhibitory pathway would be predicted to unleash the anti-tumor immune response. Therefore, a scientific rationale underpins the combination of epigenetic modulation and checkpoint blockade proposed herein. We have recently completed a combination study of azacytidine and entinostat in patients with extensively pretreated metastatic lung cancer (Taube J et al, *Science Translational Medicine* 4(127): 127ra37). This study defined a regimen of azacytidine 40 mg/m2 days 1-6 and 8-10 and entinostat 7 mg PO on days 3 and 10 on a 28-day schedule as safe and well-tolerated. Major objective responses were observed in 2 patients. Of great interest was the finding that these responses were relatively slow to develop and were durable—two characteristics that set them apart from typical responses in lung cancer to TKIs or chemotherapy, which tend to occur quickly but are not durable. Instead, the kinetics and durability of the responses are characteristic of immune-related cancer responses.

More surprising than the responses observed to epigenetic modulation alone was that several patients treated on this protocol experienced major objective responses to subsequent line of therapy, despite being heavily pretreated. Of 28 patients who received a subsequent line of therapy with antibody blockers of the PD-1 pathway—specifically, anti-PD-1 and anti-PD-L1 (the major ligand for PD-1 in solid malignancies). Of four patients with progressive lung cancer after multiple prior therapies who were treated with azacytidine and entinostat, and who received BMS-936558 or a similarly targeted anti-PD-Li antibody as the immediate subsequent therapy, three have experienced major objective responses and the fourth had disease stabilization for >6 months after initiation of anti-PD-1. These responses have been quite impressive, and are ongoing. None of these patients were responders to epigenetic therapy, and in fact, three progressed at the very first timepoint assessed. Such major objective responses in rapidly progressing non-small cell lung cancer after multiple prior therapies are rarely observed.

These findings have established a basis for dual treatment of patients with epigenetic modulation and blockade of specific immune checkpoints such as the PD-1 pathway. These two therapies need not be given concurrently, but could also be given sequentially, beginning with epigenetic modulation and followed by checkpoint blockade. This is because epigenetic modulation induced alterations in gene expression pattern continue after cessation of treatment of tumor cells (Tsai et al. *Cancer Cell* 2012, 21: 430-446).

Antibodies and Cell Lines

Peptide antigens suitable for producing antibodies of the invention may be designed, constructed and employed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology*, 201: 264-283 (1991); Merrifield, *J. Am. Chem. Soc.* 85: 21-49 (1962)).

Monoclonal antibodies of the invention may be produced in a hybridoma cell line according to the well-known technique of Kohler and Milstein. See *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (1989). Monoclonal antibodies so produced are highly specific, and improve the selectivity and specificity of diagnostic assay methods provided by the invention. For example, a solution containing the appropriate antigen may be injected into a mouse or other species and, after a sufficient time (in keeping with conventional techniques), the animal is sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063, C. Knight, Issued Oct. 7, 1997. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are preferred for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.,* 82: 8653 (1985); Spira et al., *J. Immunol. Methods,* 74: 307 (1984)).

Included in the scope of the invention are equivalent non-antibody molecules, such as protein binding domains or nucleic acid aptamers, which bind, in a phospho-specific manner, to essentially the same phosphorylatable epitope to which the phospho-specific antibodies of the invention bind. See, e.g., Neuberger et al., *Nature* 312: 604 (1984). Such equivalent non-antibody reagents may be suitably employed in the methods of the invention further described below.

Antibodies provided by the invention may be any type of immunoglobulins, including IgG, IgM, IgA, IgD, and IgE, including $F_{ab}$ or antigen-recognition fragments thereof. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to the methods disclosed in U.S. Pat. No. 4,474,893 (Reading) or U.S. Pat. No. 4,816,567 (Cabilly et al.) The antibodies may also be chemically constructed by specific antibodies made according to the method disclosed in U.S. Pat. No. 4,676,980 (Segel et al.)

The invention also provides immortalized cell lines that produce an antibody of the invention. For example, hybridoma clones, constructed as described above, that produce monoclonal antibodies to the carcinoma-related signaling protein phosphorylation sties disclosed herein are also provided. Similarly, the invention includes recombinant cells producing an antibody of the invention, which cells may be constructed by well known techniques; for example the antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Antibodies may be further characterized via immunohistochemical (IHC) staining using normal and diseased tissues to examine carcinoma-related phosphorylation and activation status in diseased tissue. IHC may be carried out according to well-known techniques. See, e.g., ANTIBODIES: A LABORATORY MANUAL, Chapter 10, Harlow & Lane Eds., Cold Spring Harbor Laboratory (1988). Briefly, paraffin-embedded tissue (e.g. tumor tissue) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating slide in primary antibody and secondary antibody; and finally detecting using ABC avidin/biotin method according to manufacturer's instructions.

Antibodies may be further characterized by flow cytometry carried out according to standard methods. See Chow et al., *Cytometry (Communications in Clinical Cytometry)* 46: 72-78 (2001). Briefly and by way of example, the following protocol for cytometric analysis may be employed: samples may be centrifuged on Ficoll gradients to remove erythrocytes, and cells may then be fixed with 2% paraformaldehyde for 10 minutes at 37° C. followed by permeabilization in 90% methanol for 30 minutes on ice. Cells may then be stained with a primary antibody, washed and labeled with a fluorescent-labeled secondary antibody. Additional fluorochrome-conjugated marker antibodies (e.g. CD45, CD34) may also be added at this time to aid in the subsequent identification of specific hematopoietic cell types. The cells would then be analyzed on a flow cytometer (e.g. a Beckman Coulter FC500) according to the specific protocols of the instrument used.

Antibodies of the invention may also be advantageously conjugated to fluorescent dyes (e.g. Alexa488, PE) for use in multi-parametric analyses along with other signal transduction (phospho-CrkL, phospho-Erk 1/2) and/or cell marker (CD34) antibodies.

Cell Culture and Mouse Models

The epigenetic modulating agents and immune modulating agents of the invention can be tested for anti-neoplasia activity in cell culture, using the exemplary methods described herein, or via other art-recognized method for performing such assessment. Such cell culture models, as well as, e.g., mouse models can be used in evaluating the efficacy of the epigenetic modulating agents and immune modulating agents of the invention to modulate target gene expression, tumor/cancer formation, growth, spread, development of other neoplasia-associated phenotypes, diseases or disorders, etc. These models and others can similarly be used to evaluate the safety/toxicity and efficacy of the epigenetic modulating agents and immune modulating agents of the invention in a pre-clinical setting.

Specific examples of cell culture systems useful for evaluation of the epigenetic modulating agents and immune modulating agents of the invention include lung cancer cell lines H838, H1299, H358, H1270, A549, H460, HCC4006, and HCC827, as well as, e.g., HT1080, HCT116, SW480, SW620, Hep3B, M14, JR8, PLF2, LLC1, LNCaP, PC3, SUM159, MDAMB-231, 22Rv1, 518A2, MHCC97, HepG2, SNU398, HuH7, NCI-H196, NCI-H1975, HT29, MKN-45, MDA-MB-231, NCI-H441, Panc-1, MiaPaCa2, BxPC3, DU-145, M2182, VCaP, OvCar-3, MCF-7, U937, K562, HeLa, T98G, or SHP-77, in addition to wild-type mice, and orthotopic or subcutaneous HT1080, HCT116, SW480, SW620, Hep3B, M14, JR8, PLF2, LLC1, LNCaP, PC3, SUM159, MDAMB-231, 22Rv1, 518A2, MHCC97, A549, H1299, HepG2, SNU398, HuH7, NCI-H196, NCI-H1975, HT29, MKN-45, MDA-MB-231, NCI-H441, Panc-1, MiaPaCa2, BxPC3, DU-145, M2182, VCaP, OvCar-3, MCF-7, U937, K562, HeLa, T98G, SHP-77, H838, H358, H1270, H460, HCC4006 or HCC827 tumor model mice. In an exemplary in vivo experiment, dsRNAs of the invention are tail vein injected into such mouse models at doses ranging from 1 to 10 mg/kg or, alternatively, repeated doses are administered at single-dose IC50 levels, and organs (e.g., prostate, liver, kidney, lung, pancreas, colon, skin, spleen, bone marrow, lymph nodes, mammary fat pad, etc.) are harvested 24 hours, (or, optionally, 2 days, 3 days, 4 days, 5 days, 6 days 7 days, two weeks, three weeks, etc.) after administration of the final dose. Such organs are then evaluated for mouse and/or human target gene expression levels and/or neoplasia status/progression, depending upon the model used. Duration of action can also be examined at, e.g., 1, 4, 7, 14, 21 or more days after final epigenetic modulating agent and/or immune modulating agent administration.

Pharmaceutical Compositions

In certain embodiments, the present invention provides for a pharmaceutical composition comprising the epigenetic modulating agent(s) and/or immune modulating agent(s) of the present invention. The epigenetic modulating agent(s) and/or immune modulating agent(s) can be suitably formulated and introduced into a subject or the environment of the cell by any means recognized for such delivery.

Such compositions typically include the agent and a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in a selected solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For a compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of an epigenetic modulating agent and/or an immune modulating agent (i.e., an effective dosage) depends on the epigenetic modulating agent and/or an immune modulating agent selected. For instance, single dose amounts of an epigenetic modulating agent and/or an immune modulating agent in the range of approximately 1 pg to 1000 mg may be administered; in some embodiments, 10, 30, 100, or 1000 pg, or 10, 30, 100, or 1000 ng, or 10, 30, 100, or 1000 µg, or 10, 30, 100, or 1000 mg may be administered. In some embodiments, 1-5 g of the compositions can be administered. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of an epigenetic modulating agent and/or an immune modulating agent (including, e.g., a protein, polypeptide, or antibody) can include a single treatment or, preferably, can include a series of treatments.

Nucleic acids encoding for certain modulating agents of the invention can be inserted into expression constructs, e.g., viral vectors, retroviral vectors, expression cassettes, or plasmid viral vectors, e.g., using methods known in the art, including but not limited to those described in Xia et al., (2002). Expression constructs can be delivered to a subject by, for example, inhalation, orally, intravenous injection, local administration (see U.S. Pat. No. 5,328,470) or by stereotactic injection (see e.g., Chen et al. (1994), Proc. Natl. Acad. Sci. USA, 91, 3054-3057). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the gene delivery system.

It can be appreciated that the method of introducing epigenetic modulating agent(s) and/or immune modulating agent(s)s into the environment of a cell will depend on the type of cell and the make up of its environment.

Suitable amounts of epigenetic modulating agent(s) and/or immune modulating agent(s) must be introduced and these amounts can be empirically determined using standard methods. Exemplary effective concentrations of individual epigenetic modulating agent(s) and/or immune modulating agent(s) species in the environment of a cell can be 500 millimolar or less, 50 millimolar or less, 10 millimolar or less, 1 millimolar or less, 500 nanomolar or less, 50 nanomolar or less, 10 nanomolar or less, or even compositions in which concentrations of 1 nanomolar or less can be used.

The pharmaceutical compositions can be included in a kit, container, pack, or dispenser together with instructions for administration.

Cancer Therapies

Currently available therapies and their dosages, routes of administration and recommended usage are known in the art and have been described in such literature as the Physician's Desk Reference (60th ed., 2006). Routes of administration include parenterally, intravenously, subcutaneously, intracranially, intrahepatically, intranodally, intraureterally, subureterally, subcutaneously, and intraperitoneally.

Dosage

Dosage of one or more agents of the invention (e.g., epigenetic modulating agents and/or immune modulating agents) can be determined by one of skill in the art and can also be adjusted by the individual physician in the event of any complication. Typically, the dosage ranges from 0.001 mg/kg body weight to 5 g kg body weight. In some embodiments, the dosage range is from 0.001 mg/kg body weight to 1 g kg body weight, from 0.001 mg kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 g/kg body weight to 30 g/kg body weight.

Alternatively, the dose range will be titrated to maintain serum levels between 5 g/mL and 30 g/mL.

As an example, in initial clinical trials, a regimen of azacytidine 40 mg/m2 days 1-6 and 8-10 and entinostat 7 mg PO on days 3 and 10 on a 28-day schedule was determined to be both safe and well-tolerated, while also demonstrating effect in certain patients.

Administration of the doses recited above can be repeated for a limited period of time. In some embodiments, the doses are given once a day, or multiple times a day, for example but not limited to three times a day. In one embodiment, the doses recited above are administered daily for several weeks or months. The duration of treatment depends upon the subject's clinical progress and responsiveness to therapy, e.g., shrinkage of tumor sizes. Continuous, relatively low maintenance doses are contemplated after an initial higher therapeutic dose. As exemplary, an inhibitor of PD1 and/or PD-L1, or AZA and a pharmaceutically acceptable carrier can be formulated for direct application by injection into the tumor in the subject.

Efficacy testing can be performed during the course of treatment using the methods described herein, e.g., ultrasound, MRI and CT to monitor the shrinkage in size of the tumors in the treated subject. A decrease in size of the tumors during and after treatment indicates that the treatment is effective in reducing tumor size. Measurements of the degree of severity of a number of symptoms associated with cancerous tumors are also noted prior to the start of a treatment and then at later specific time period after the start of the treatment. A skilled physician will be able to ascertain the tumor sizes and related symptoms by known methods in the art and those described herein.

Combination Therapies

In a specific embodiment, cycling therapy involves the administration of a first cancer therapeutic for a period of time, followed by the administration of a second cancer therapeutic for a period of time, optionally, followed by the administration of a third cancer therapeutic for a period of time and so forth, and repeating this sequential administration, i.e., the cycle in order to reduce the development of resistance to one of the cancer therapeutics, to avoid or reduce the side effects of one of the cancer therapeutics, and/or to improve the efficacy of the cancer therapeutics.

When two therapeutically effective regimens are administered to a subject concurrently, the term "concurrently" is not limited to the administration of the cancer therapeutics at exactly the same time, but rather, it is meant that they are administered to a subject in a sequence and within a time interval such that they can act together (e.g., synergistically to provide an increased benefit than if they were administered otherwise). When two prophylactically effective regimens are administered to a subject concurrently, the term "concurrently" is not limited to the administration of the cancer therapeutics at exactly the same time, but rather, it is meant that they are administered to a subject in a sequence and within a time interval such that they can act together (e.g., synergistically to provide an increased benefit than if they were administered otherwise). For example, the cancer therapeutics may be administered at the same time or sequentially in any order at different points in time; however, if not administered at the same time, they should be administered sufficiently close in time so as to provide the desired therapeutic effect, preferably in a synergistic fashion. The combination cancer therapeutics can be administered separately, in any appropriate form and by any suitable route. When the components of the combination cancer therapeutics are not administered in the same pharmaceutical composition, it is understood that they can be administered in any order to a subject in need thereof. For example, a first therapeutically effective regimen can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second cancer therapeutic, to a subject in need thereof. In another embodiment, a first prophylactically effective regimen can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second cancer therapeutic, to a subject in need thereof. In various embodiments, the cancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the cancer therapeutics are administered within the same office visit. In another embodiment, the combination cancer therapeutics are administered at 1 minute to 24 hours apart.

In a specific embodiment, the combination therapies have the same mechanism of action. In another specific embodiment, the combination therapies each have a different mechanism of action.

Methods of Treatment

The present invention provides for both prophylactic and therapeutic methods of treating a subject at risk of (or susceptible to) a neoplastic disease or disorder.

"Treatment", or "treating" as used herein, is defined as the application or administration of a therapeutic agent (e.g., an epigenetic agent and/or an immunomodulatory agent) to a patient, or application or administration of a therapeutic agent to an isolated tissue or cell line from a patient, who has the disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

In one aspect, the invention provides a method for preventing in a subject, a disease or disorder as described above, by administering to the subject a therapeutic agent (e.g., an epigenetic agent and/or an immunomodulatory agent). Subjects at risk for the disease can be identified by, for example, one or a combination of diagnostic or prognostic assays as described herein. Administration of a prophylactic agent can occur prior to the detection of, e.g., cancer in a subject, or the manifestation of symptoms characteristic of the disease or disorder, such that the disease or disorder is prevented or, alternatively, delayed in its progression.

Another aspect of the invention pertains to methods of treating subjects therapeutically, i.e., altering the onset of symptoms of the disease or disorder. These methods can be performed in vitro (e.g., by culturing the cell with the agent(s)) or, alternatively, in vivo (e.g., by administering the agent(s) to a subject).

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment according to that individual's drug response genotype, expression profile, biomarkers, etc. Pharmacogenomics allows a clinician or physician to target prophylactic or therapeutic treatments to patients who will most benefit from the treatment and to avoid treatment of patients who will experience toxic drug-related side effects.

Therapeutic agents can be tested in a selected animal model. For example, an epigenetic agent or immunomodulatory agent as described herein can be used in an animal model to determine the efficacy, toxicity, or side effects of treatment with said agent. Alternatively, an agent (e.g., a therapeutic agent) can be used in an animal model to determine the mechanism of action of such an agent.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, Molecular Cloning (Cold Spring Harbor Laboratory Press, Cold Spring Harbor, N.Y.); Sambrook et al., 1989, Molecular Cloning, 2nd Ed. (Cold Spring Harbor Laboratory Press, Cold Spring Harbor, N.Y.); Sambrook and Russell, 2001, Molecular Cloning, 3rd Ed. (Cold Spring Harbor Laboratory Press, Cold Spring Harbor, N.Y.); Ausubel et al., 1992, Current Protocols in Molecular Biology (John Wiley & Sons, including periodic updates); Glover, 1985, DNA Cloning (IRL Press, Oxford); Anand, 1992; Guthrie and Fink, 1991; Harlow and Lane, 1988, Antibodies, (Cold Spring Harbor Laboratory Press, Cold Spring Harbor, N.Y.); Jakoby and Pastan, 1979; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Riott, Essential Immunology, 6th Edition, Blackwell Scientific Publications, Oxford, 1988; Hogan et al., Manipulating the Mouse Embryo, (Cold Spring Harbor Laboratory Press, Cold Spring Harbor, N. Y., 1986); Westerfield, M., The zebrafish book. A guide for the laboratory use of zebrafish (*Danio rerio*), (4th Ed., Univ. of Oregon Press, Eugene, 2000).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The present invention is described by reference to the following Examples, which are offered by way of illustration and are not intended to limit the invention in any manner. Standard techniques well known in the art or the techniques specifically described below were utilized.

Example 1

Clinical Observation of Anti-Tumor Efficacy of Combined Epigenetic and Anti-PD-1 Therapies Five patients who received treatment on a clinical trial of epigenetic therapy (specifically, here, AZA treatments) for advanced treatment-refractory NSCLC were placed on trials for immunotherapy targeting the PD-1/PDL1 immune tolerance checkpoint. Of these five patients, three experienced durable partial responses to immunotherapy now ongoing for 14 to 26 months, and the other two had stable disease that lasted 8.25 and 8.5 months, respectively. (see FIGS. 23 and 25) For comparison, 41-46% of NSCLC patients on these two trials of immunotherapy alone. one for anti-PD1 and the other for anti-PD-L1 therapy, passed 24 weeks without progression and 16-17% had durable partial response rates. (6-8)

Example 2

Figure 1:
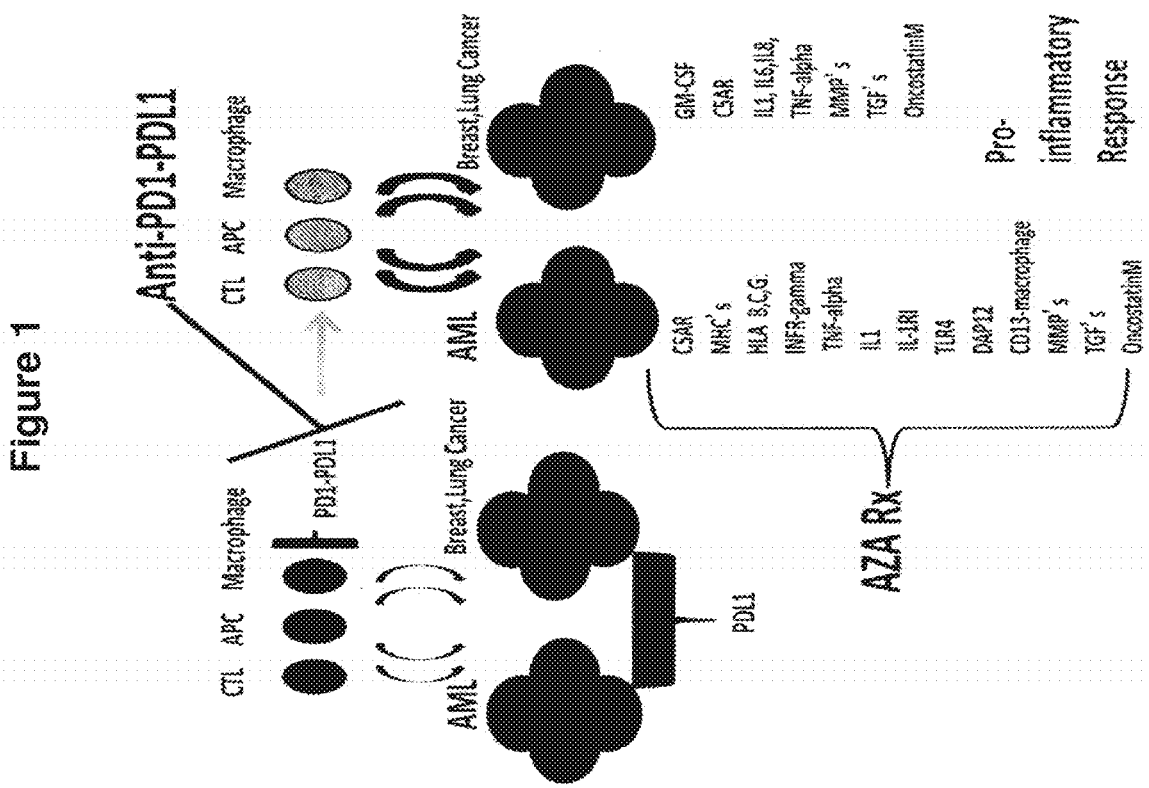
FIG. 1 presents a model of action for both azacytidine and anti-PD1 or anti-PDL1 therapies, as related to cancer progression (e.g., breast, lung or AML) and pro-inflammatory responses (including posited molecular targets of azacytidine treatment).

Pro-Inflammatory Changes in Gene Expression Revealed to Increase with AZA Treatment The clinical effect observed in Example 1 was believed to relate to the modes of action of both epigenetic treatments such as AZA and to anti-PD-1 immune tolerance checkpoint immunotherapies, such as anti-PD1 and/or anti-PDL1 antibodies (FIG. 1). The impact of AZA administration upon tumor-derived cell lines was then assessed for a number of genes, and revealed pro-inflammatory changes in expression of a wide number of genes to increase with AZA treatment. Specifically, as shown in FIG. 2, such effects were observed across genes C5AR; GM-CSF; MHCs; TNF-alpha; IL1 alpha/beta; IL6; IL8; IL-15; IL-15R; IL15RA; MMPs-TIMP1; COX2; OncostatinM; ICAM1; VCAM1; and TGF-betas and their receptors in epithelial cell lines, while effects were also observed for genes IFN-gammaR; TNF-alpha; MHCs; HLA B, C, G; TLR4; DAP12; CD13-macrophage maturation; IL-1RI; IL1 alpha/beta; MMPs-TIMP1; OncostatinM; and TGF-betas and their receptors in AML cell lines (as indicated).

Example 3

Figure 3:
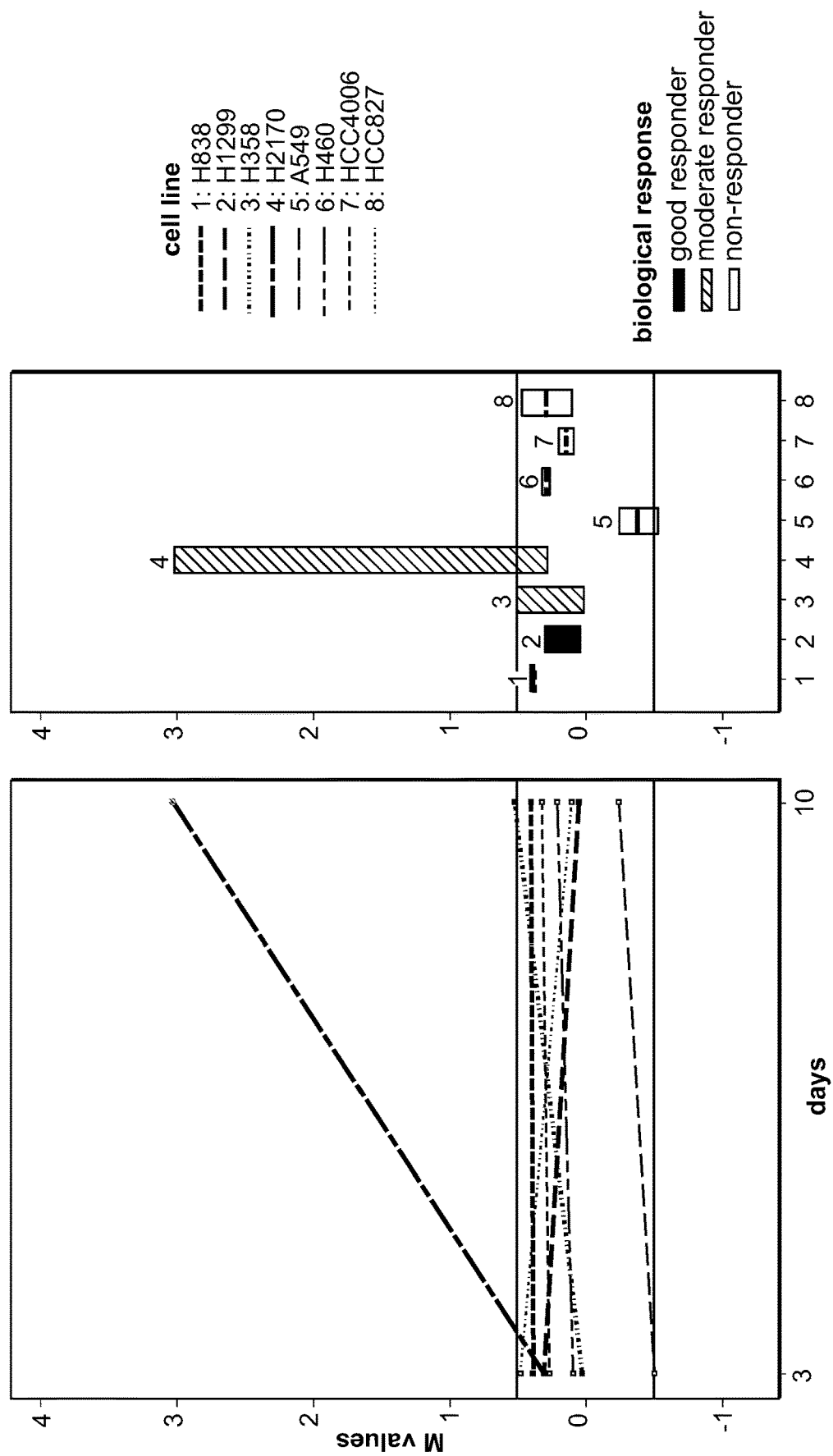
FIG. 3 shows the trend in levels of STAT1 (as depicted via M values) observed in various human cell lines (human NSCLC cell lines H838, H1299, H358, H1270 and H460; human adenocarcinoma/lung cell lines A549 and HCC827, and hepatocellular carcinoma/lung cell line HCC4006) over the course of AZA administration. STAT1 levels assayed in subjects undergoing treatment, classified as "good responder", "moderate responder" and "non-responder", are also shown.
Figure 4:
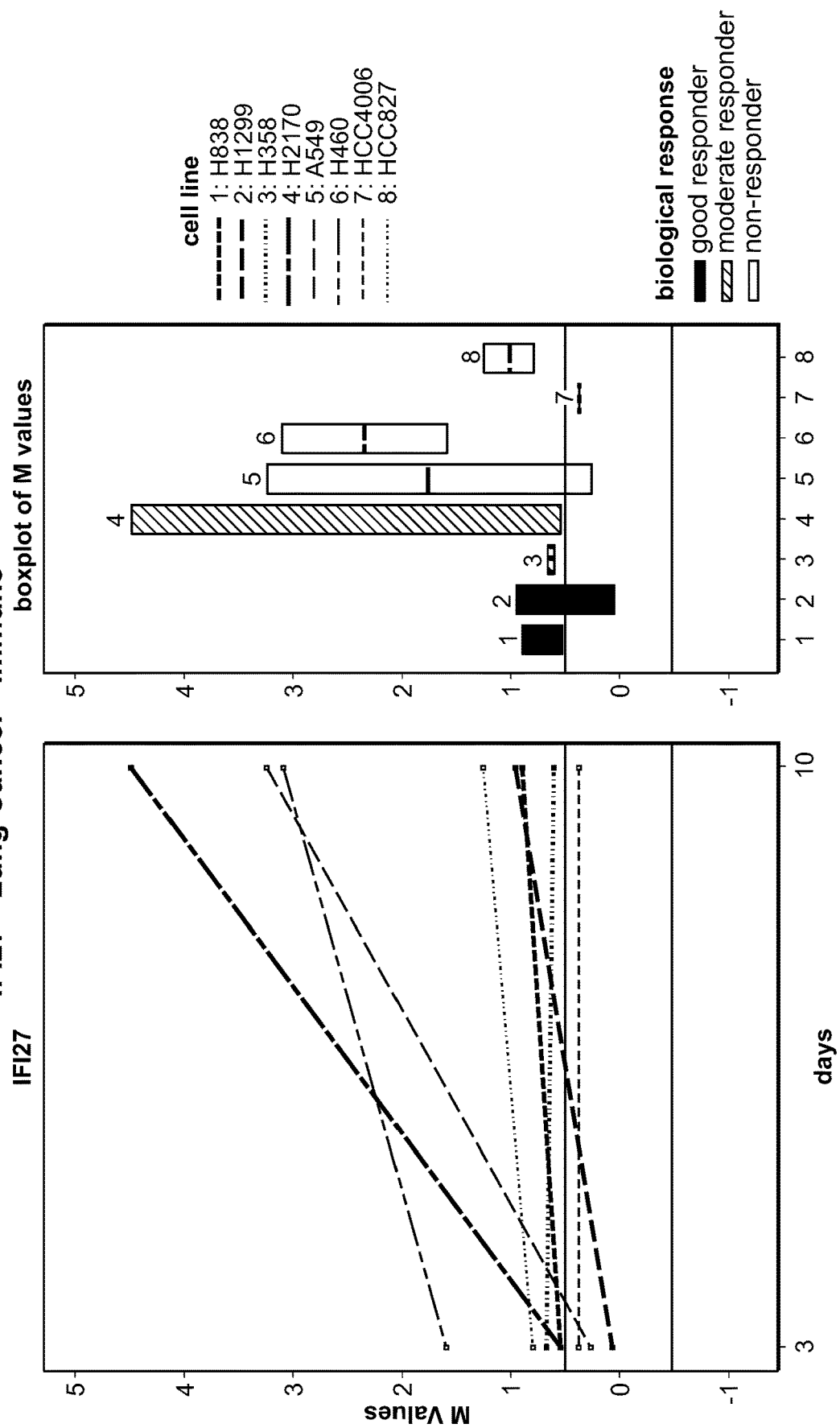
FIG. 4 shows the trend in levels of IFI27 (as depicted via M values) observed in various human cell lines (human NSCLC cell lines H838, H1299, H358, H1270 and H460; human adenocarcinoma/lung cell lines A549 and HCC827, and hepatocellular carcinoma/lung cell line HCC4006) over the course of AZA administration. IFI27 levels assayed in subjects undergoing treatment, classified as "good responder", "moderate responder" and "non-responder", are also shown.
Figure 5:
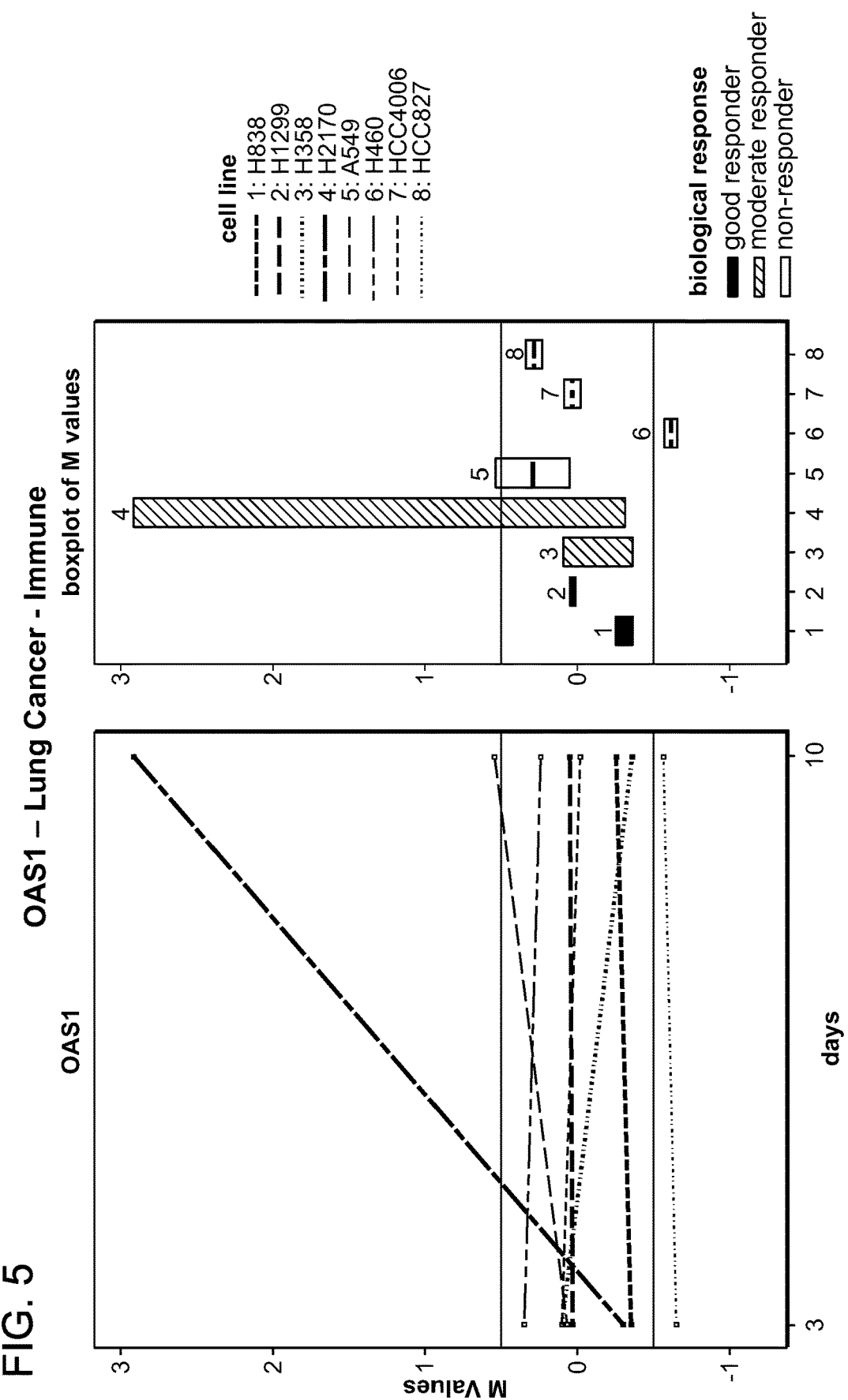
FIG. 5 shows the trend in levels of OAS1 (as depicted via M values) observed in various human cell lines (human NSCLC cell lines H838, H1299, H358, H1270 and H460; human adenocarcinoma/lung cell lines A549 and HCC827, and hepatocellular carcinoma/lung cell line HCC4006) over the course of AZA administration. OAS1 levels assayed in subjects undergoing treatment, classified as "good responder", "moderate responder" and "non-responder", are also shown.
Figure 6:
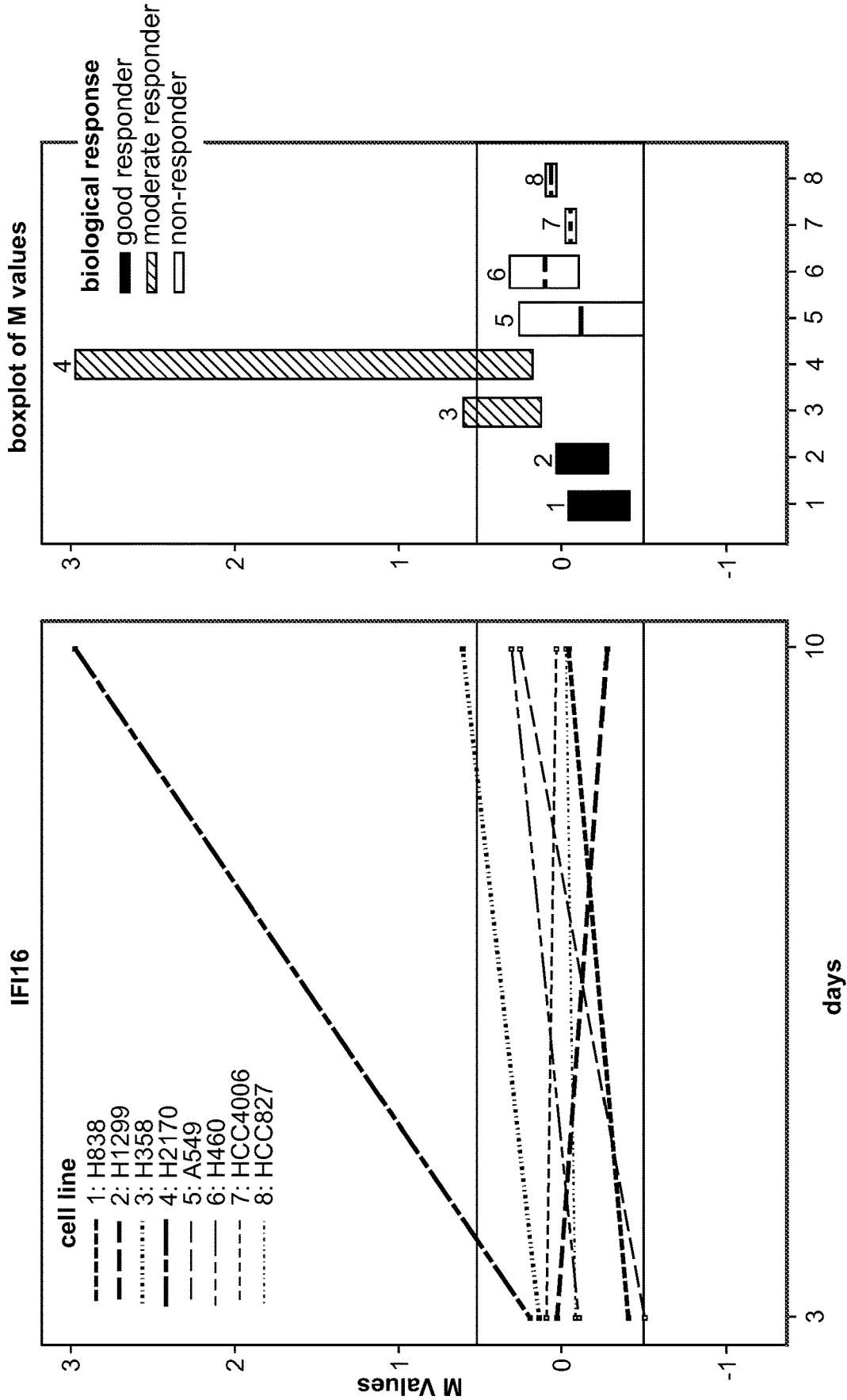
FIG. 6 shows the trend in levels of IFI16 (as depicted via M values) observed in various human cell lines (human NSCLC cell lines H838, H1299, H358, H1270 and H460; human adenocarcinoma/lung cell lines A549 and HCC827, and hepatocellular carcinoma/lung cell line HCC4006) over the course of AZA administration. IFI16 levels assayed in subjects undergoing treatment, classified as "good responder", "moderate responder" and "non-responder", are also shown.
Figure 7:
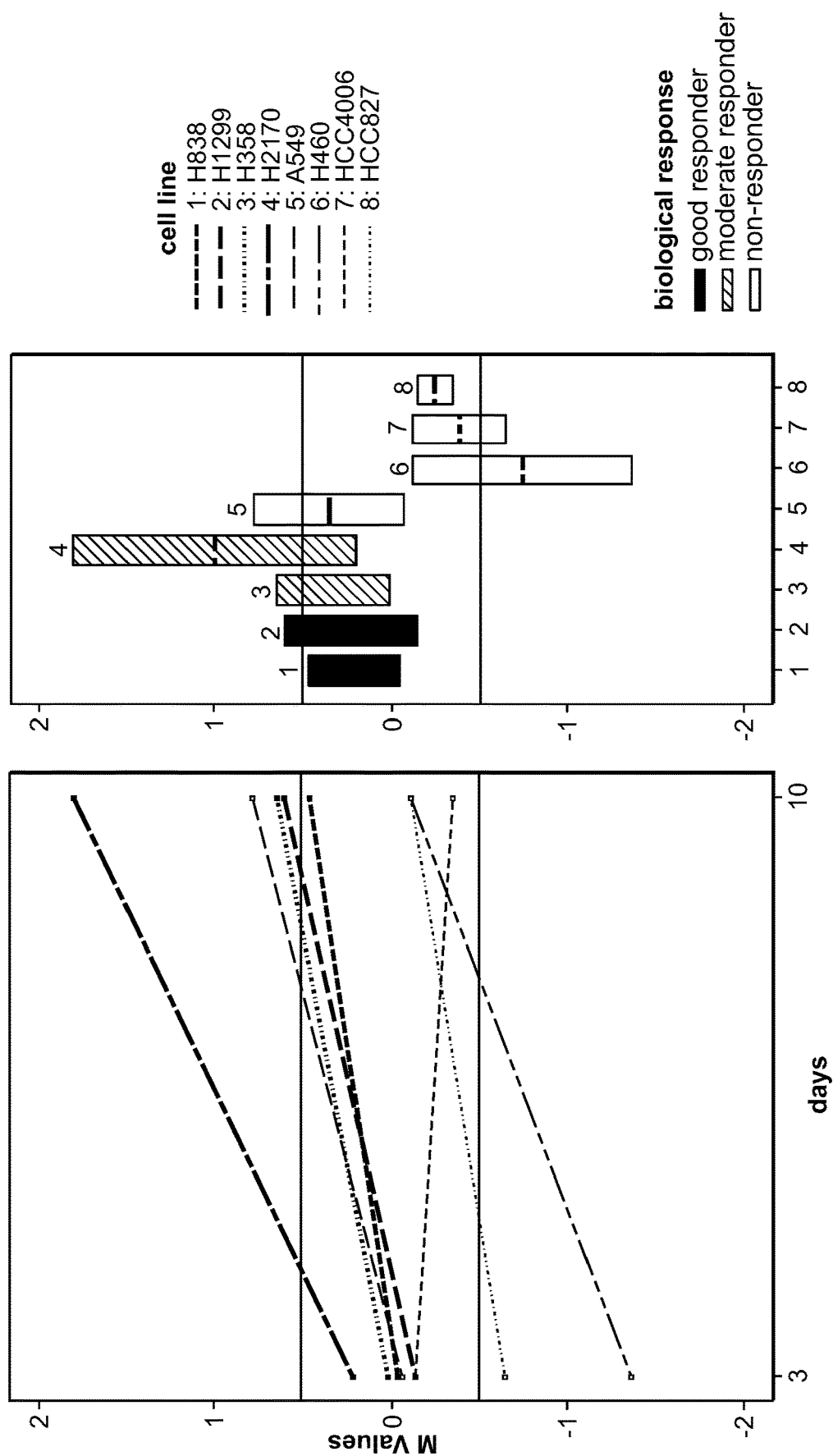
FIG. 7 shows the trend in levels of HLA-A (as depicted via M values) observed in various human cell lines (human NSCLC cell lines H838, H1299, H358, H1270 and H460; human adenocarcinoma/lung cell lines A549 and HCC827, and hepatocellular carcinoma/lung cell line HCC4006) over the course of AZA administration. HLA-A levels assayed in subjects undergoing treatment, classified as "good responder", "moderate responder" and "non-responder", are also shown.
Figure 8:
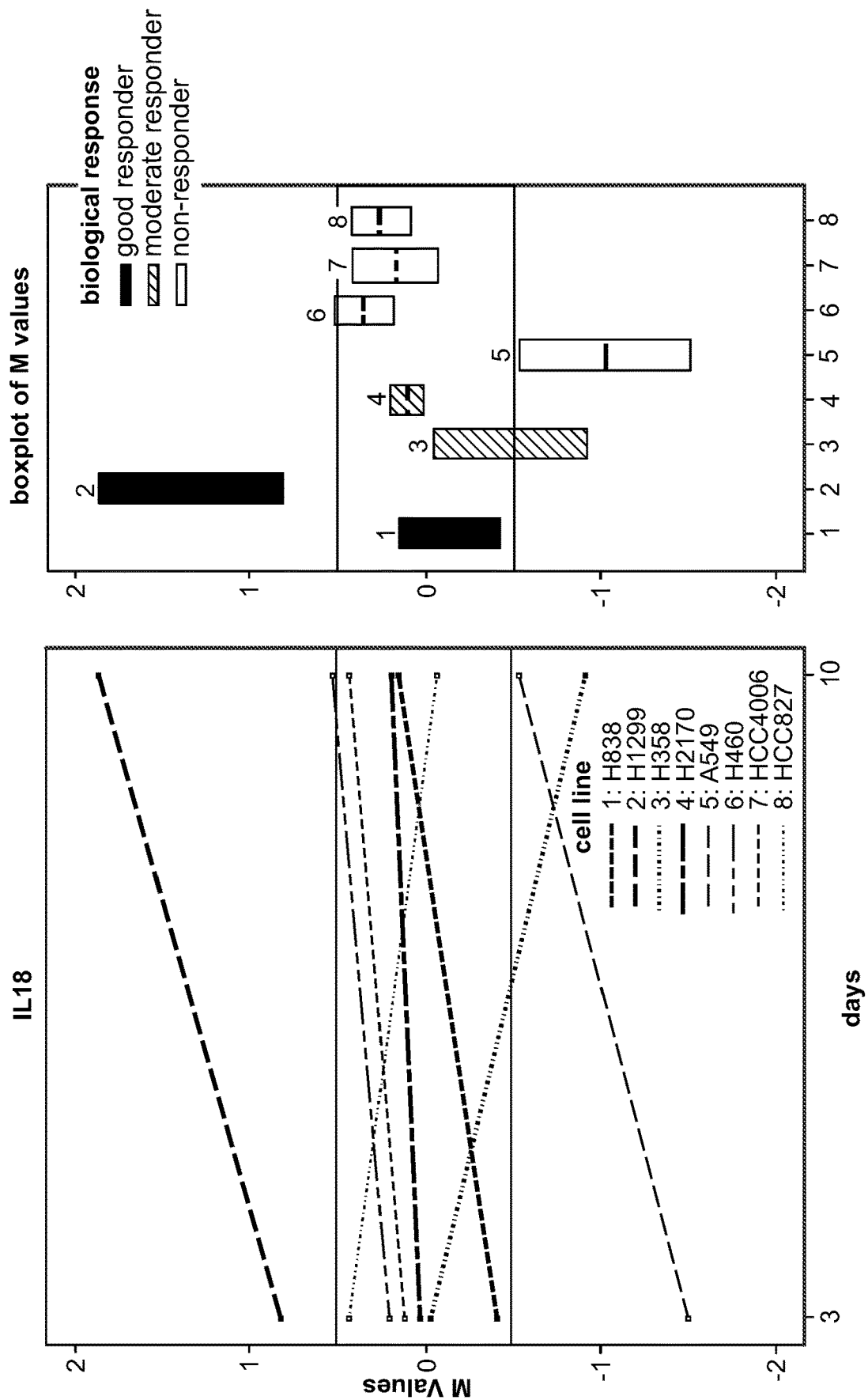
FIG. 8 shows the trend in levels of IL18 (as depicted via M values) observed in various human cell lines (human NSCLC cell lines H838, H1299, H358, H1270 and H460; human adenocarcinoma/lung cell lines A549 and HCC827, and hepatocellular carcinoma/lung cell line HCC4006) over the course of AZA administration. IL18 levels assayed in subjects undergoing treatment, classified as "good responder", "moderate responder" and "non-responder", are also shown.
Figure 9:
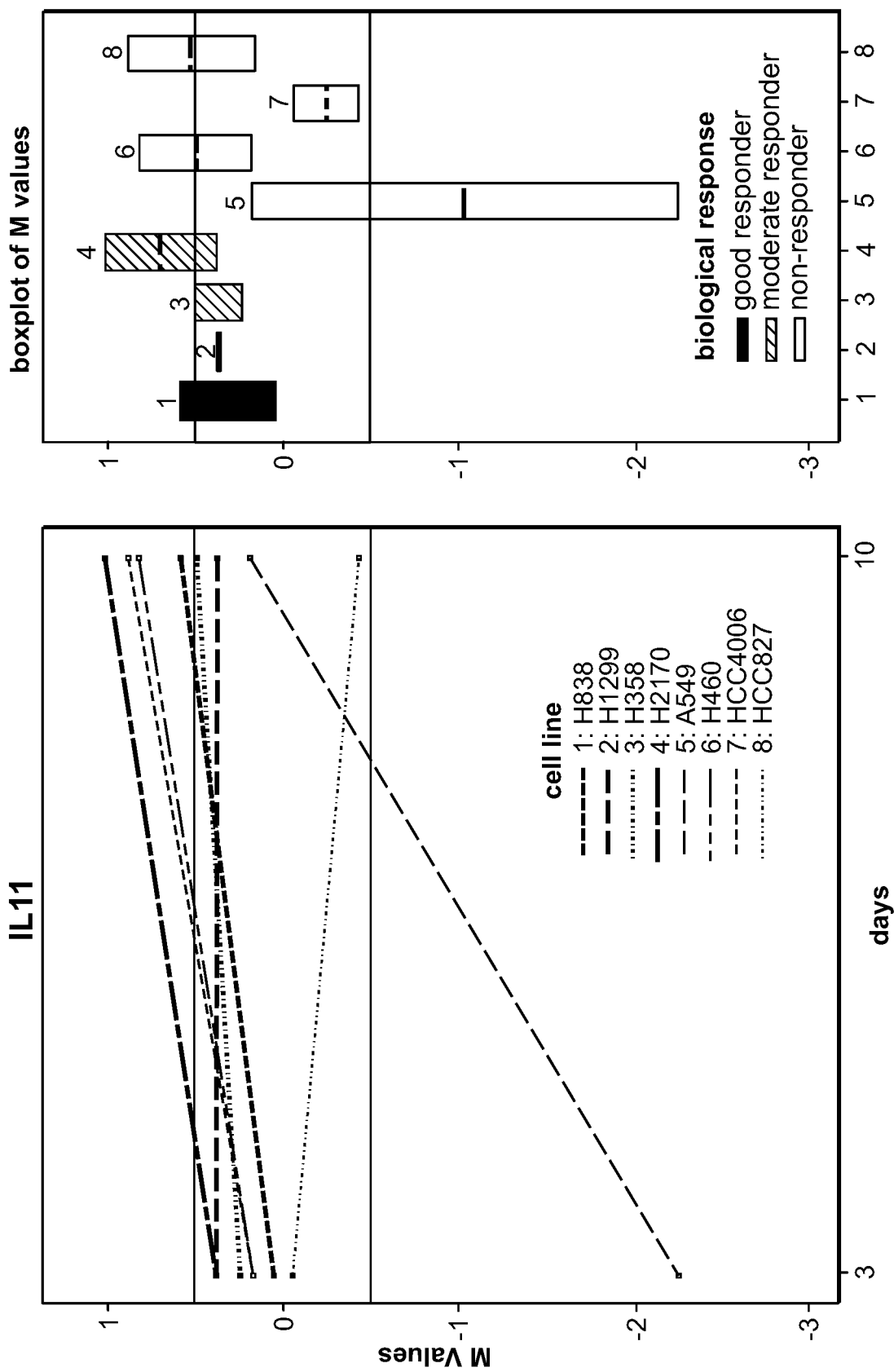
FIG. 9 shows the trend in levels of IL11 (as depicted via M values) observed in various human cell lines (human NSCLC cell lines H838, H1299, H358, H1270 and H460; human adenocarcinoma/lung cell lines A549 and HCC827, and hepatocellular carcinoma/lung cell line HCC4006) over the course of AZA administration. IL11 levels assayed in subjects undergoing treatment, classified as "good responder", "moderate responder" and "non-responder", are also shown.

Monitoring of STAT1, IFI27, OAS1, IFI16, HLA-A, IL18, and IL11 in Lung Cancer Cell Lines During Treatment Revealed Varying Levels of Molecular Response Lung cancer-derived cell lines (including human NSCLC cell lines H838, H1299, H358, H1270 and H460; human adenocarcinoma/lung cell lines A549 and HCC827, and hepatocellular carcinoma/lung cell line HCC4006) were assayed for levels of STAT1 (FIG. 3), IFI27 (FIG. 4), OAS1 (FIG. 5), IFI16 (FIG. 6), HLA-A (FIG. 7), IL18 (FIG. 8), and IL11 (FIG. 9) during a treatment regimen including AZA administration over the course of 10 days. As shown in each of FIGS. 3-8, levels of these genes were also assessed in each of eight clinical subjects as shown (including two "good responders", two "moderate responders" and four "non-responders").

Figure 10:
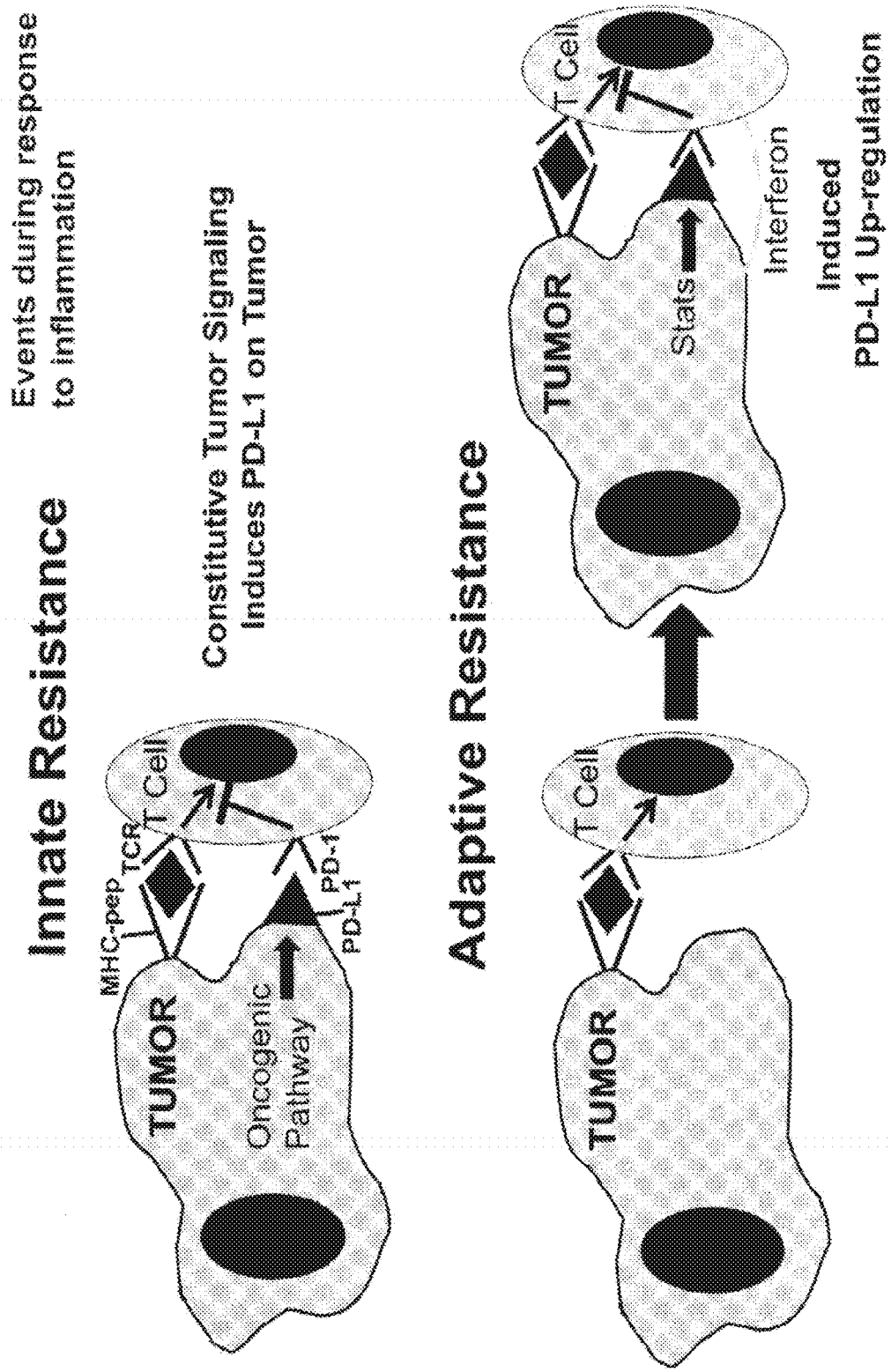
FIG. 10 shows two models (innate and adaptive resistance, respectively) believed to describe PD-L1 upregulation in tumors.
Figure 11:
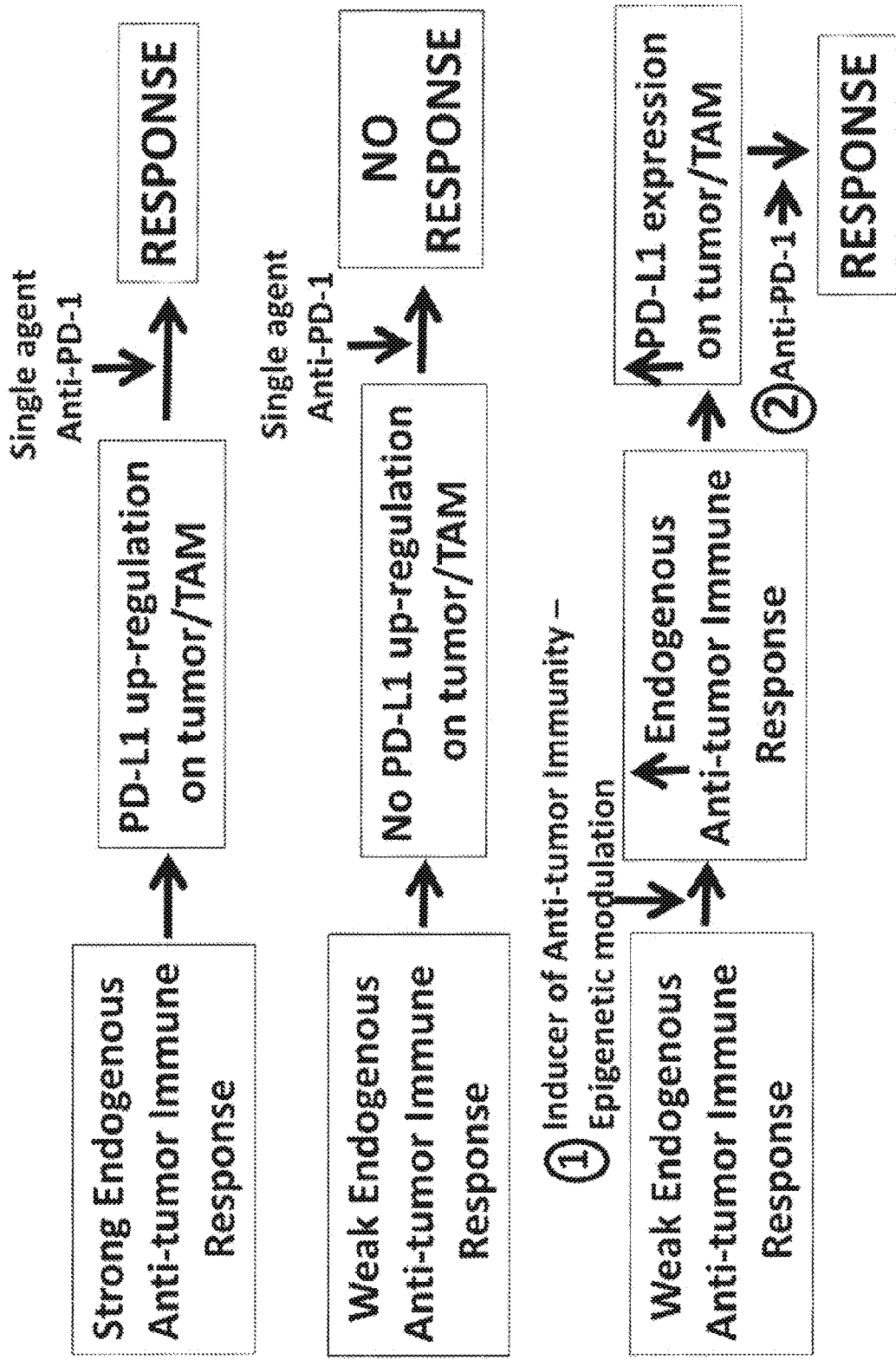
FIG. 11 presents a model of the therapeutic implications for PD-1 pathway blockade of the adaptive resistance model shown in FIG. 10. As shown in the bottom diagram, combination of epigenetic modulation and anti-PD-1 treatments have unexpectedly been shown herein to induce a response in tumors believed to have possessed only weak endogenous anti-tumor immune responses prior to epigenetic modulation and anti-PD-1 treatments.

The above observations suggested that an adaptive resistance model of tumor-T cell interaction could be relevant to the PD-L1 upregulation-related response effects that were observed (FIG. 10). Indeed, while a likely reason for the lack of responsiveness observed for certain tumors administered single agent anti-PD-1 therapies related to the fact that such tumors elicited a weak endogenous anti-tumor immune response (versus a strong endogenous anti-tumor immune response, which would have responded to single agent anti-PD-1), one reason that administration of an epigenetic modulator (like AZA) preceding or concomitant with administration of an anti-PD-1 agent would provoke an anti-tumor response even in a tumor that would otherwise elicit weak endogenous anti-tumor response was the impact of the epigenetic modulation therapy in upregulating the endogenous anti-tumor immune response and thereby PD-L1 expression on the tumor/TAM, thereby increasing the susceptibility of such a tumor to anti-PD-1 therapy (FIG. 11).

Figure 12:
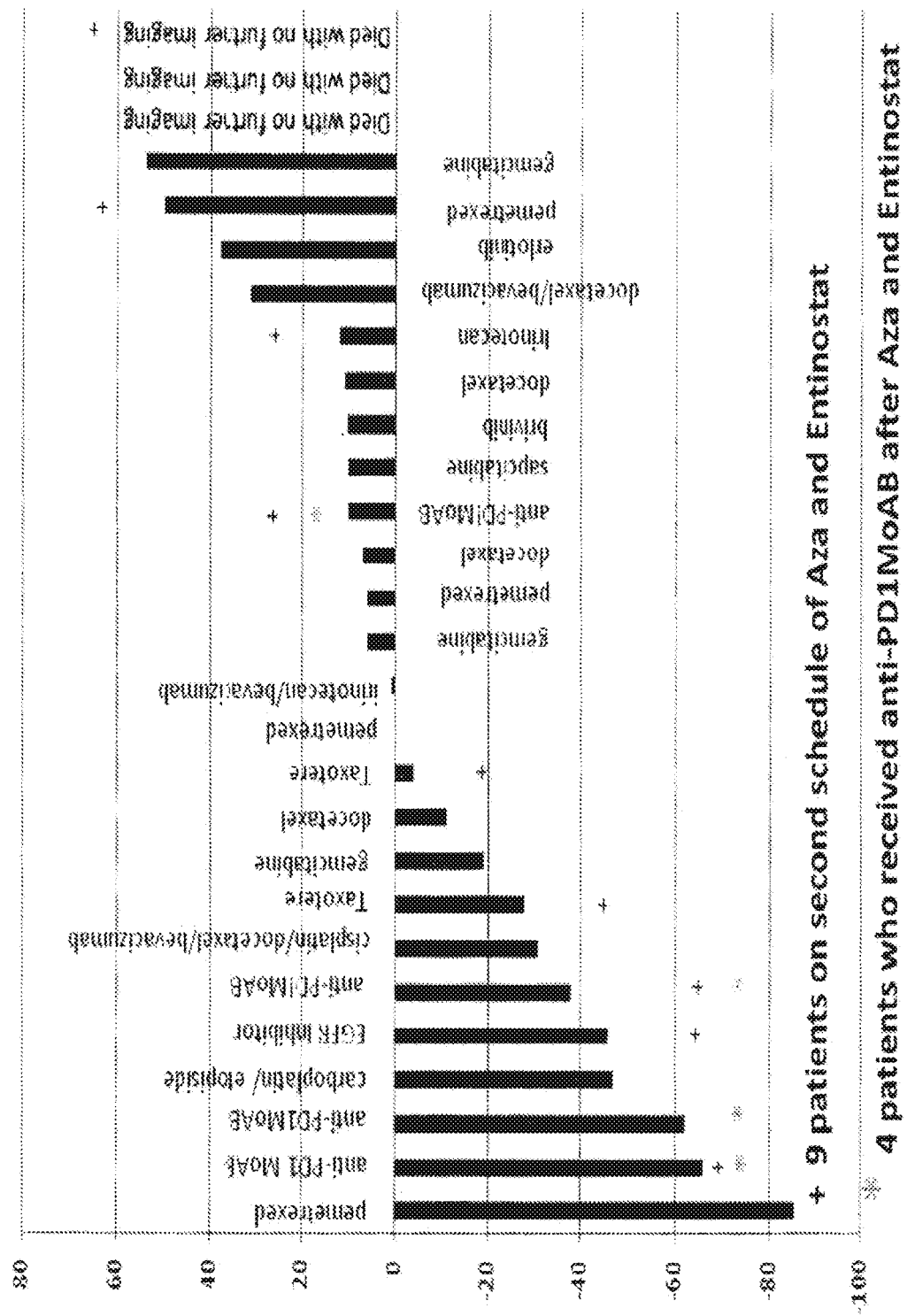
FIG. 12 shows the responses of subjects first administered epigenetic therapy to several chemotherapeutic agents as indicated.

Underscoring the efficacy of pre-administration of epigenetic therapy (e.g., AZA) in predisposing the tumor of a subject to anti-PD-1 immunotherapy, subjects administered such therapies were among the best responders to such combination therapies, as compared to subjects administered epigenetic therapy followed by other therapy. Indeed, with the exception of one subject that was responsive to pemetrexed after epigenetic therapy, the greatest responses to chemotherapy after epigenetic therapy were observed among those subjects administered anti-PD1 mAb (FIG. 12).

Figure 13:
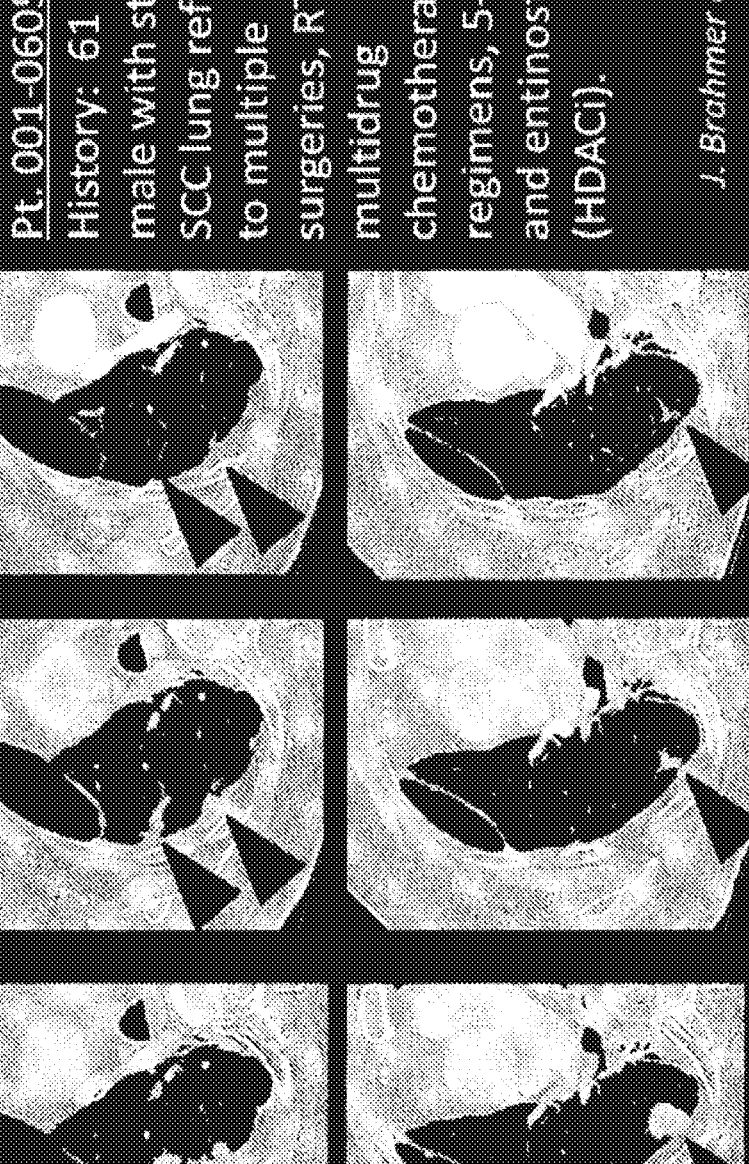
FIG. 13 demonstrates the response of a "non-immunogenic" tumor (here, a stage 4 NSCLC tumor) to anti-PD-1 therapy, when administered after epigenetic therapy.
Figure 14:
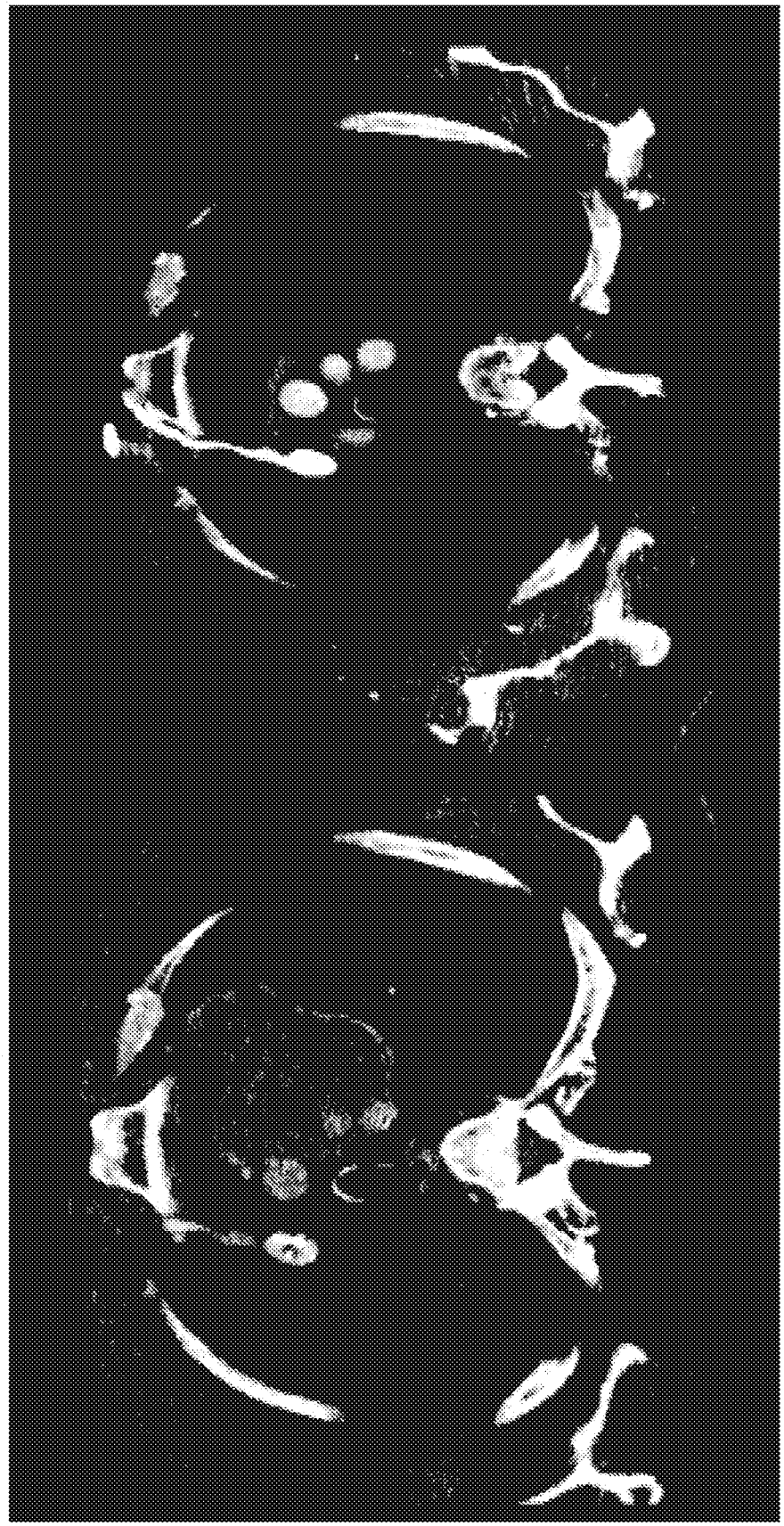
FIG. 14 shows that epigenetic therapy and anti-PD-1 therapy is a potentially synergistic combination therapy for stage 4 NSCLC. Shown are cross-sectional images of a subject administered anti-PD-1 therapy following epigenetic therapy, both pre-therapy (showing images of stage 4 NSCLC tumor) and after 8 months of therapy.

The impact of anti-PD-1 treatment following epigenetic therapy was particularly striking in one subject that entered the clinical trial at stage 4 NSCLC, yet then exhibited reduction of tumor size over the course of more than eight months of such treatment (FIGS. 13-14).

Figure 15:
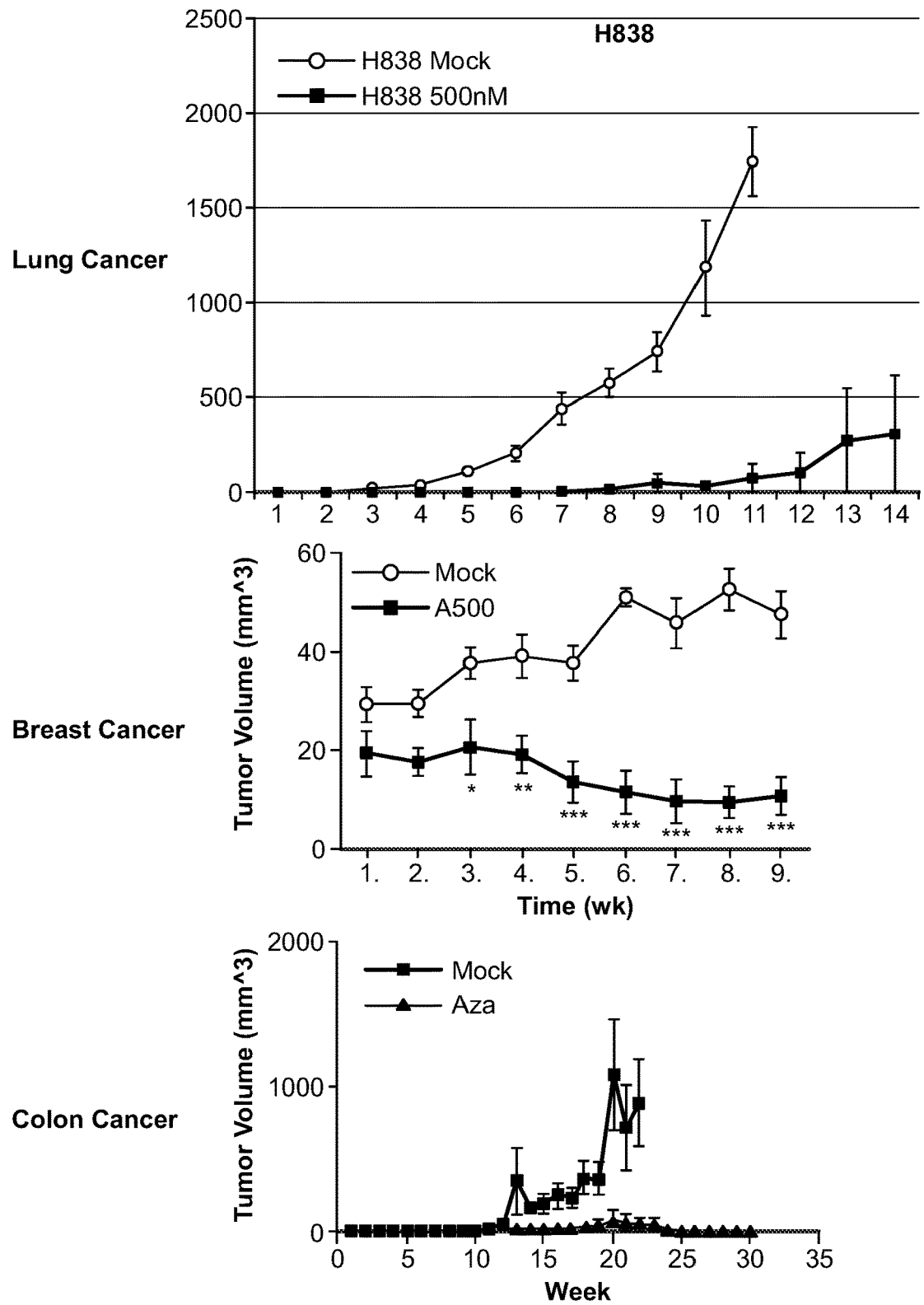
FIG. 15 shows that robust responses in "memory" experiments have been observed in lung (H838), breast and colon cancers for AZA treatment at 500 nM, specifically depicting the potent responses observed for primary mammospheres and orthotopic explants of primary cells.

Creation of AZA treatment "memory" was not only observed in lung cancer cell lines, but was also observed in breast cancer and colon cancer cell lines (FIG. 15).

Example 4

Clinical Assays and Design of Cell Culture and Expression Profiling Experiments NSCLC cell lines were treated with the DNA hypomethylating agent azacytidine (AZA-Vidaza) and the genes and pathways altered, as mapped by genome-wide expression and DNA methylation analyses, were analyzed. AZA-induced pathways were analyzed in The Cancer Genome Atlas (TCGA) project by mapping the derived gene signatures in hundreds of lung adeno (LUAD) and squamous cell carcinoma (LUSC) samples. By doing so, AZA was found to up-regulate genes and pathways related to both innate and adaptive immunity and genes related to immune evasion in a several NSCLC lines. DNA hypermethylation and low expression of IRF7, an interferon transcription factor, tracked with this signature particularly in LUSC. In concert with these events, AZA up-regulated PD-L1 transcripts and protein, a key ligand-mediator of immune tolerance. Analysis of TCGA samples demonstrated that a significant proportion of primary NSCLC had low expression of AZA-induced immune genes, including PD-L1.

Materials and Methods

Clinical Data

Institutional review board approved informed consent signed by each patient allowed the collection of clinical data following treatment on trial with epigenetic therapy. Relevant data were obtained by chart review. Representative images demonstrating responses to therapy were obtained from computed tomography series employed in the assessment of patient responses to anti-PD1 or anti-PD-L1 directed immune-checkpoint therapy. Assessment of response to treatment was performed by a single reference radiologist who employed (RECIST 1.0) to generate measurements for target lesions to be followed over the course of therapy. Change in target lesions from baseline (%) is calculated by summing the diameter of all target lesions at each radiographic tumor evaluation and calculating percentage change at a given time point ([(Target Lesion SumTimepoint X/Target Lesion SumBaseline)−1]*100)

TCGA Samples

Level 3 RNA-Seq data (Illumina HiSeq RNA-Seq platform, Illumina, Inc., San Diego, Calif., USA) were downloaded for 353 NSCLC samples (129 LUAD/224 LUSC) and 54 adjacent nontumor lung tissue samples from *The Cancer Genome Atlas* (TCGA) Data Portal. Similarly, level 1 DNA methylation data (Illumina Infinium HumanMethylation450 BeadChip, Illumina, Inc., San Diego, Calif., USA) were downloaded for 353 NSCLC samples (222 LUAD/149 LUSC) and 74 adjacent non-tumor lung tissue samples. Among these, data for 174 NSCLC samples (80 LUAD/94 LUSC) and 21 adjacent non-tumor lung tissue samples were available on both of the above platforms.

RNA-Seq Data Analysis

TCGA level 3 RNA-Seq data already normalized and quantified at gene levels were obtained, and presented as RPKM values (Reads Per Kilobase per Million mapped reads). To construct heat maps: 1) Values of 0 (indicating no reads observed for a gene) in the RPKM data were set to NA; 2) the remaining RPKM values were log 2 transformed; 3) genes from X and Y chromosomes were removed; and 4) heat maps were made using the "heatmap.2" function in "gplots" package from CRAN (50), being centered and scaled in the row direction, and using the default functions for computing distance and hierarchical clustering (or being specifically ordered in column according to the order of other heat maps). Expression spectrums for individual genes were displayed in five quartile intervals following the order of associated heat maps of the RNA-Seq data.

Infinium DNA Methylation Data Analysis

TCGA level 1 DNA methylation data contained raw binary intensity data files. Raw data files were imported into R to calculate beta values (beta value Infinium=M/[U+M], M: mean intensities of the Methylated bead type, U: mean intensities of the Unmethylated bead types), M values (M value Infinium=log 2 [M/U]) and detection p-values (calculated by comparing probes to negative control probes to determine if signals are significantly different from the background) using the "methylumi" package from Bioconductor (22). Beta values and M values for probes with detection p-value >0.05 were considered not significantly different from background and were masked as NA. TCGA methylation data were first assessed for batch effects by principle component analysis (PCA) on the M values. To accomplish this, data points from X chromosome and Y chromosome as well as data points that were associated with SNPs (Single Nucleotide Polymorphisms) were removed, and the first two principle components were used for plotting.

Spearman's correlation coefficients between methylation (beta value of probe, Illumina Infinium HumanMethylation450 BeadChip) and gene expression (RPKM value of gene, Illumina HiSeq RNA-Seq platform) were calculated using TCGA samples with available data on both platforms. For a particular gene, only methylation probes that had a negative Spearman's correlation coefficient and an adjusted p-value (FDR) for the coefficient <0.01 were considered informative and their relative distances to the corresponding transcriptional start site (TSS) of the genes were calculated from genomic coordinates obtained from the UCSC genome browser. Heat maps of the M values of informative probes were made using the "heatmap.2" function in "gplots" package from CRAN (50), being centered and scaled in the row direction, and ordered according to the associated heat maps of the RNA-Seq data in column and to the relative distances to TSS in row.

For in vitro DNA methylation values, DNA was extracted from cell lines that were either untreated or treated with AZA at day 3, at the end of treatment, and day 10 (7 days post end of treatment) and analyzed by the Illumina Infinium HumanMethylation450 BeadChips (Illumina, Inc., San Diego, Calif., USA). Raw data were imported into R using the "methylumi" package from Bioconductor (22). Data points for probes with detection p-value >0.05 were masked as NA. Δ beta values (Δ beta value=beta value AZA−beta value Mock) were calculated and used to make boxplots. Heat maps were made similarly like those for the TCGA data using informative probes defined by the TCGA data.

Expression Microarray Data

For in vitro RNA extracted from cell lines treated with AZA, analyses were done at exactly the same time points as for DNA methylation above. Analyses from wild type colon cancer, HCT116 cells, and genetic knockout counterparts for DNA methyltransferases (DKO cells) were also performed. Expression microarrays were carried out using Agilent Human 4×44K expression arrays (Agilent Technologies, Santa Clara, Calif., USA, Cat#: G4112F). Within-array and between-array normalization was performed using Loess and Aquantile normalization, respectively (23). Median of the M values (M value Expression=log 2 [AZA/Mock] OR log 2 [DKO/HCT116]) was determined for multiple probes associated with the same gene.

Gene Set Enrichment Analysis (GSEA)

For each of the eight lung cancer cell lines (H838, H1299, H358, H1270, A549, H460, HCC4006, HCC827) a ranked gene list was created (genes were sorted by decreasing M value). These eight ranked gene lists were entered in the GSEA tool (51-52) and the enrichment of both Kegg (53) and Reactome (54) pathways in these lists was calculated (default parameters). A gene set was selected when it was enriched in any of the eight cell lines (p value <0.05 and false discovery rate <0.25). The normalized enrichment scores (NES) for the gene sets in each cell line were used to create the heat maps. When a certain gene set was not significant in a cell line, it was assigned a NES of 0.

Transcription Factor Analysis

Expression and methylation data were analyzed to find genes whose re-expression was linked to demethylation after AZA treatment. Genes were selected based on a set of cut-offs, both for the methylation and expression values: A gene was considered to be re-expressed when at day 3 or day 10 the median M value of all the probes linked to that gene was higher than 0.5. Infinium probes were analyzed separately at their distances from the transcription start site for each gene examined. For a probe to be called demethylated, it had to have a beta value higher than 0.5 in the mock treatment and a difference in beta value between mock and AZA treatment had to be at least 0.25. Only probes that were associated with a CpG island and that were located within 1000 bp upstream and 1000 bp downstream of the transcription start site were used in the analyses. The probes that passed these filters were validated using the TCGA methylation and expression data (see the definition of informative probes in the "Infinium DNA Methylation Data" section of Methods). Only genes that had an expression-methylation correlation value <−0.25 and a false discovery rate <0.05 were retained. To better understand the biological implications of the re-expressed genes, the gene lists were searched for transcription factors. Two human transcription factor lists obtained from Ravasi et al. (25) and Vaquerizas et al. (26, 27) were combined and the resulting list was matched to the lists of demethylated and re-expressed genes. The targets of IRF7 from the list of genes that are 4-fold or more up-regulated in H2170 by AZA were similarly identified using the TranscriptomeBrowser database (28).

Flow Cytometry Methods (FACS)

Frozen cells were thawed in 37 degrees Celsius and washed once with flow-washing buffer. Aliquots of single-cell suspension were then stained with fluorescent-labeled antibodies for 15 mins at room temperature. Each sample was washed twice and re-suspended in flow-washing buffer and analyzed by FACSCalibur. The following antibodies were used: CD274 (12-5983-42 Ebiosciences), HLA abc(12-9983-42 Ebiosciences), CD276(331606 Biolegend), CD119 (558934 BD), B2 microblogumin(551337BD), CD58 (555921BD). Changes between AZA treated and mock cells were calculated using mean fluorescence intensities (MFI) and the formula log 2([(MFIantibody, treated)−(MFIisotype, treated)]/[(MFIantibody, mock)−(MFIisotype, mock)]).

PSCAN

PSCAN (55) is an online software tool that predicts the association of user defined gene-lists with transcription factors by scanning promoter sequences of co-regulated or co-expressed genes looking for over- or under-represented motifs. RefSeq IDs of the gene lists were obtained from BioMart and analyzed in PSCAN. Scanned promoter region was −450 to +50 base pairs around the transcription start site and employing TRANSFAC as the database for co-regulated or co-expressed genes.

Example 5

Azacytidine Induced Immune Response in Non-Small Cell Lung Cancer Cell Lines

Figure 16A:
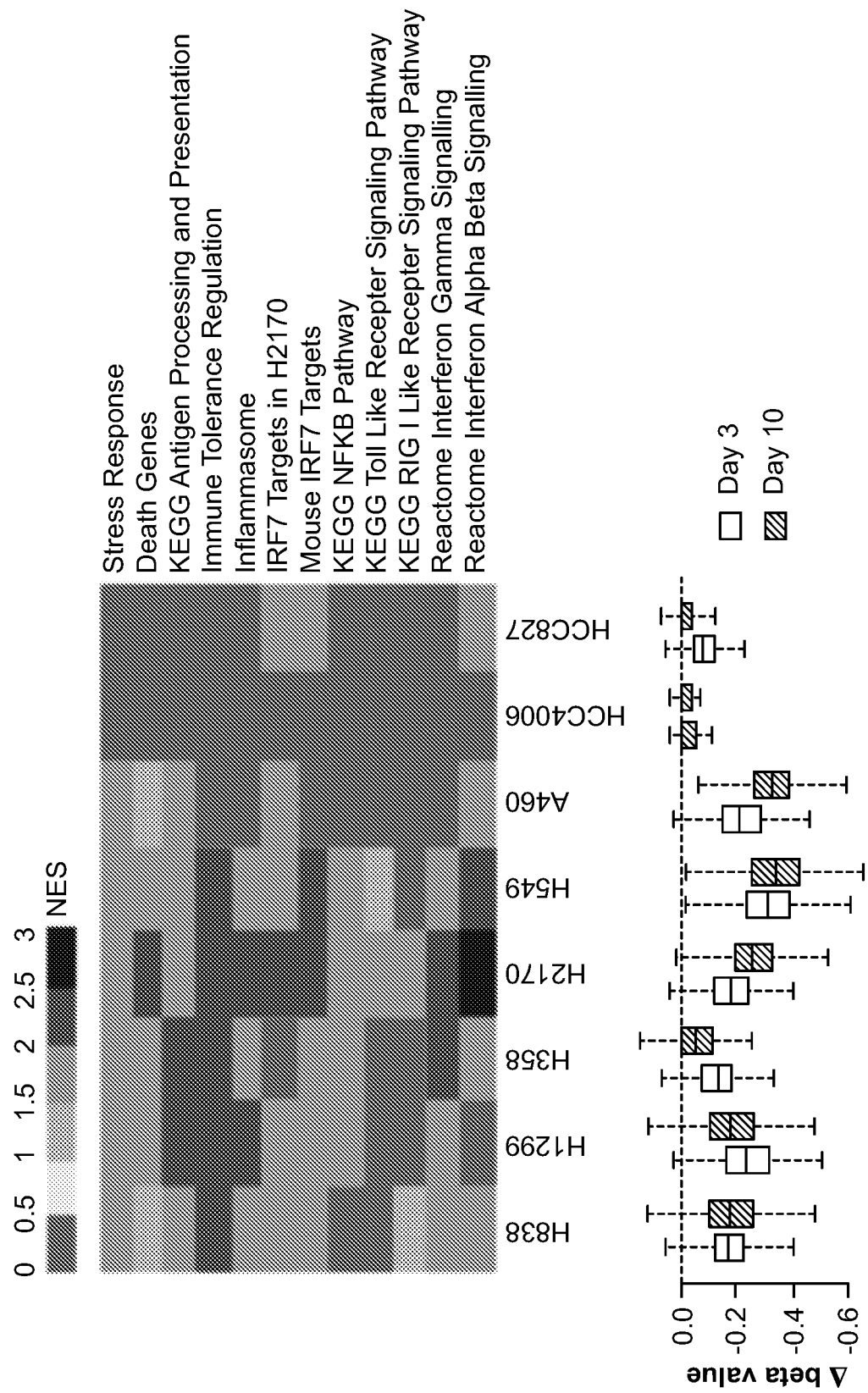

A previously validated pre-clinical model was employed to examine how AZA alters expression of key pathways in NSCLC cell lines.(29) Cells were treated in vitro with 500 nM AZA for 72 hours then harvested immediately after withdrawal of drug and again one week later for genome wide methylation and expression studies. To the point of the clinical suggestion that epigenetic therapy may provide sensitization to subsequent immune-checkpoint blockade it was agnostically noted that one or more of the top ten pathways emerging for each cell line was immune related and the genes involved were important to the interaction of both innate and adaptive anti-tumor immunity. In certain prior instances, the ability of AZA to up-regulate individual immune pathway steps relative to assembly of major histocompatibility antigens (HLA Class I), interferon pathway genes, and cancer-testis antigens was noted (11-16). However, the present analysis revealed a more complex, concordant, broad immune gene signature. Strikingly, Gene Set Enrichment Analysis showed AZA induced up-regulation of multiple immune-related pathways in a manner roughly correlating to the degree of demethylation in response to AZA treatment (FIG. 16A and Table 1 below). Each of these components possesses a demonstrated role in immune tolerance pathways associated with immune checkpoints and immune evasion. Some of these genes have low expression associated with cancer-specific promoter region DNA hypermethylation, and increased expression after treatment with DNA demethylating drugs (11, 12). In this regard, it was noteworthy that when compared to normal bronchial epithelial cells, NSCLC had been observed to exhibit diminished innate immune responses to viral-like stimuli involving intertwined pathways of cell-intrinsic responses to infection and inflammation (11).

TABLE 1

GSEA-Assessed AZA Induced Up-Regulation of Multiple Immune-Related Pathways

Figure 19:
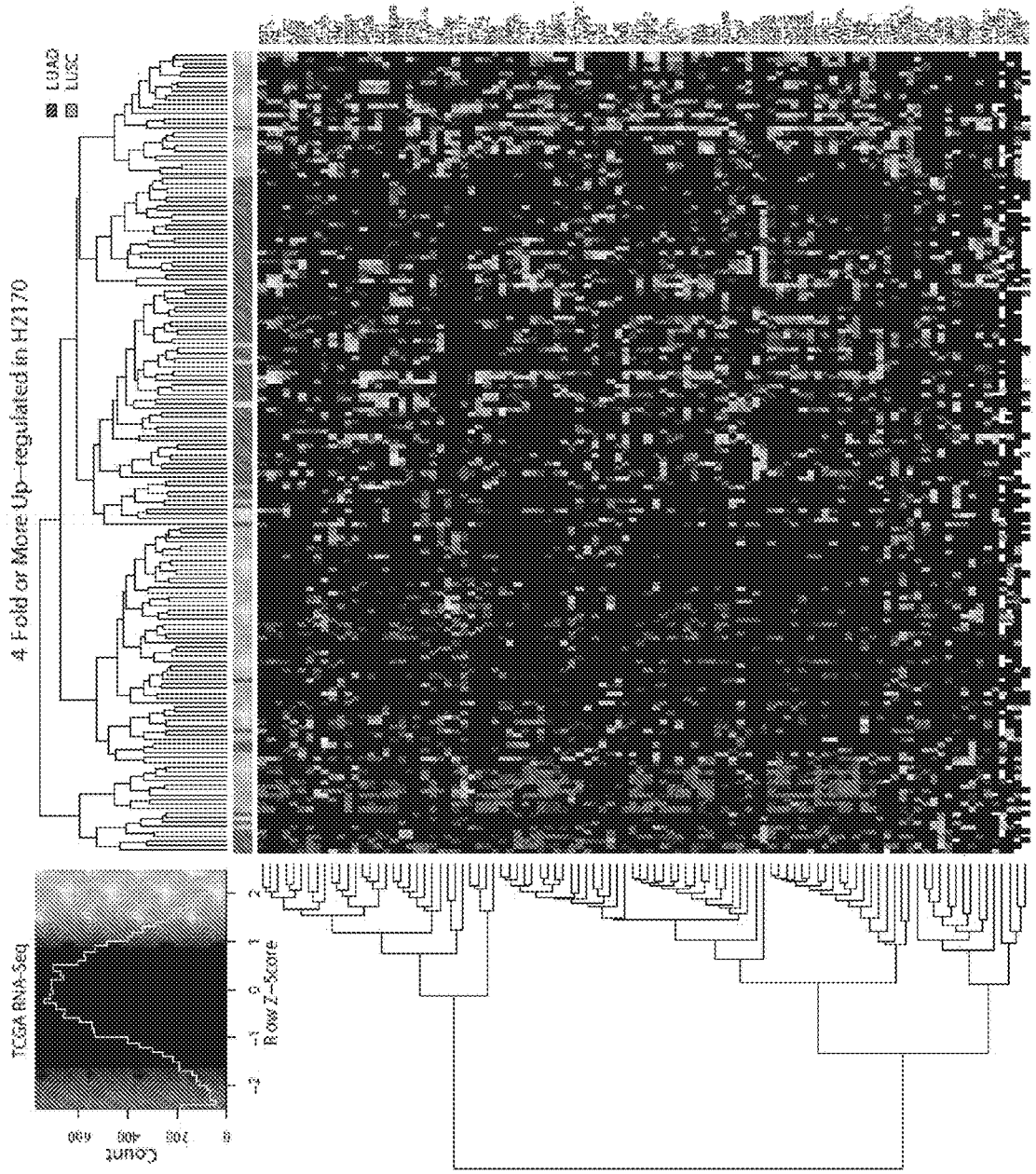

| Gene Symbol | GSEA Leading Genes | Genes with Available TCGA RNA-Seq Data | Genes Used in FIG. 19 |
|---|---|---|---|
| ATG12 |  | Y |  |
| ATG5 | Y | Y | Y |
| AZI2 |  | Y |  |
| CASP10 |  | Y |  |
| CASP8 | Y | Y | Y |
| CHUK | Y | Y | Y |
| CXCL10 | Y | Y | Y |
| CYLD |  | Y |  |
| DAK |  | Y |  |
| DDX3X |  | Y |  |
| DDX3Y |  | Y |  |
| DDX58 | Y | Y | Y |
| DHX58 | Y | Y | Y |
| FADD |  | Y |  |
| IFIH1 | Y | Y | Y |
| IFNA1 |  | Y |  |
| IFNA10 |  | Y |  |
| IFNA13 |  | Y |  |
| IFNA14 |  | Y |  |
| IFNA16 |  | Y |  |
| IFNA17 |  | Y |  |
| IFNA2 |  | Y |  |
| IFNA21 |  | Y |  |
| IFNA4 |  | Y |  |
| IFNA5 | Y | Y | Y |
| IFNA6 |  | Y |  |
| IFNA7 |  | Y |  |
| IFNA8 |  | Y |  |
| IFNB1 | Y | Y | Y |
| IFNE |  | Y |  |
| IFNK |  | Y |  |
| IFNW1 |  | Y |  |
| IKBKB |  | Y |  |
| IKBKE |  | Y |  |
| IKBKG | Y | Y | Y |
| IL12A |  | Y |  |
| IL12B |  | Y |  |
| IL8 |  | Y |  |
| IRF3 |  | Y |  |
| IRF7 | Y | Y | Y |
| ISG15 | Y | Y | Y |
| MAP3K1 |  | Y |  |
| MAP3K7 |  | Y |  |
| MAPK10 |  | Y |  |
| MAPK11 | Y | Y | Y |
| MAPK12 |  | Y |  |
| MAPK13 | Y | Y | Y |
| MAPK14 | Y | Y | Y |
| MAPK8 |  | Y |  |
| MAPK9 |  | Y |  |
| MAVS |  | Y |  |
| NFKB1 |  | Y |  |
| NFKBIA | Y | Y | Y |
| NFKBIB |  | Y |  |
| NLRX1 |  | Y |  |
| OTUD5 |  | Y |  |
| PIN1 |  | Y |  |
| RELA | Y | Y | Y |
| RIPK1 |  | Y |  |
| RNF125 |  | Y |  |
| SIKE1 | Y | Y | Y |
| TANK | Y | Y | Y |
| TBK1 | Y | Y | Y |
| TBKBP1 | Y | Y | Y |
| TMEM173 |  | Y |  |
| TNF |  | Y |  |
| TRADD |  | Y |  |
| TRAF2 | Y | Y | Y |
| TRAF3 |  | Y |  |
| TRAF6 |  | Y |  |
| TRIM25 | Y | Y | Y |

Antigen Presentation

Figure 16B:
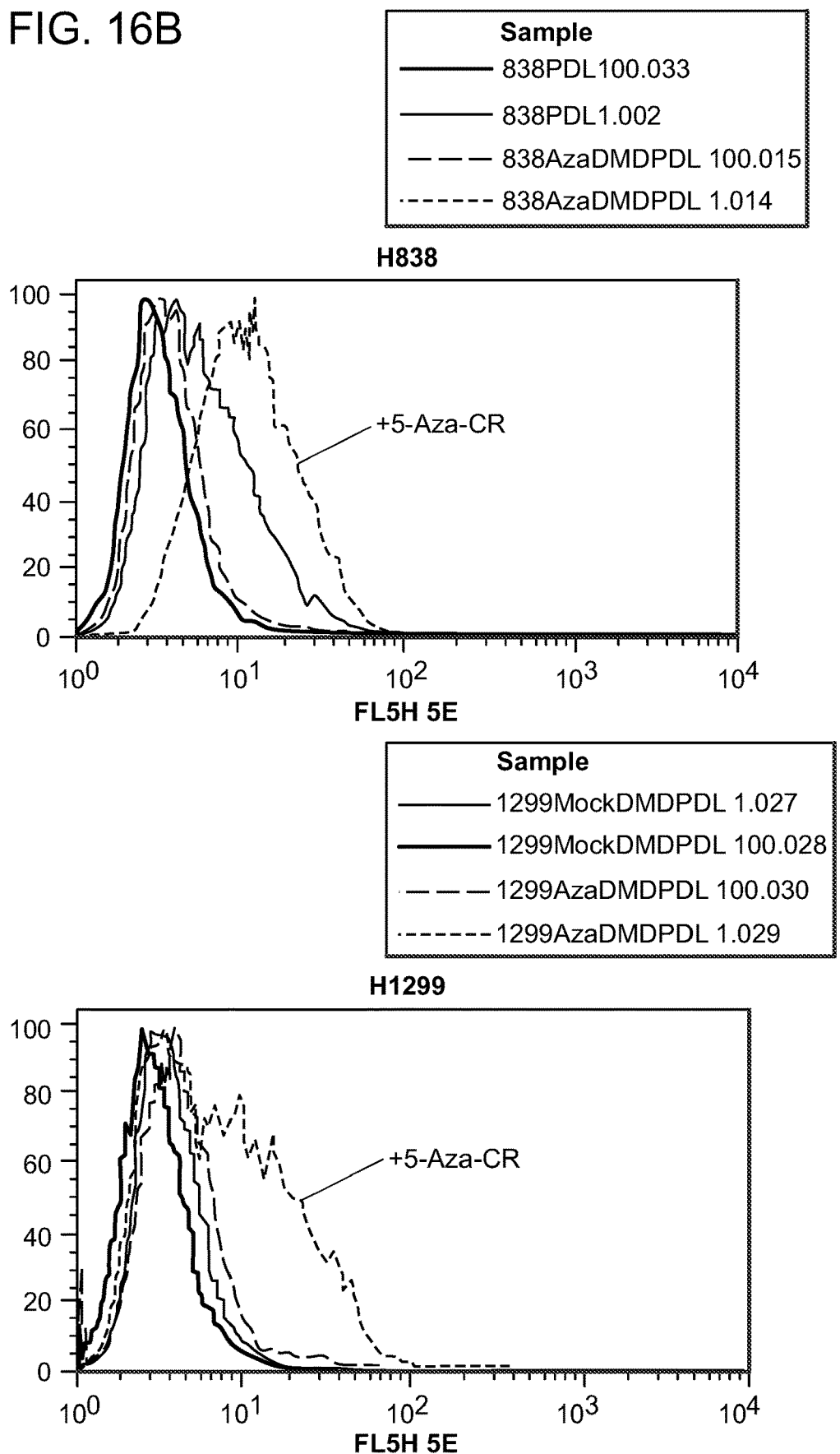
Figure 16C:
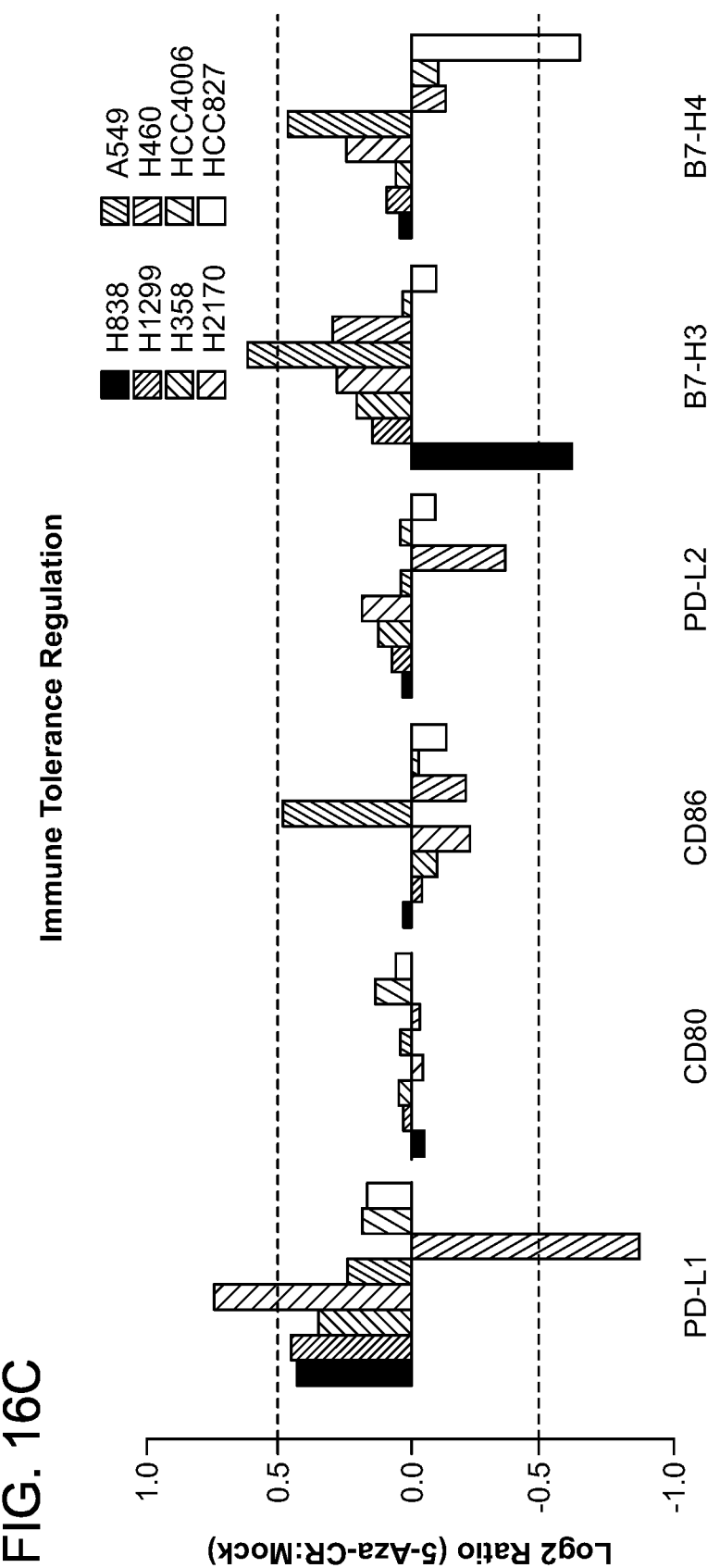
Figure 16D:
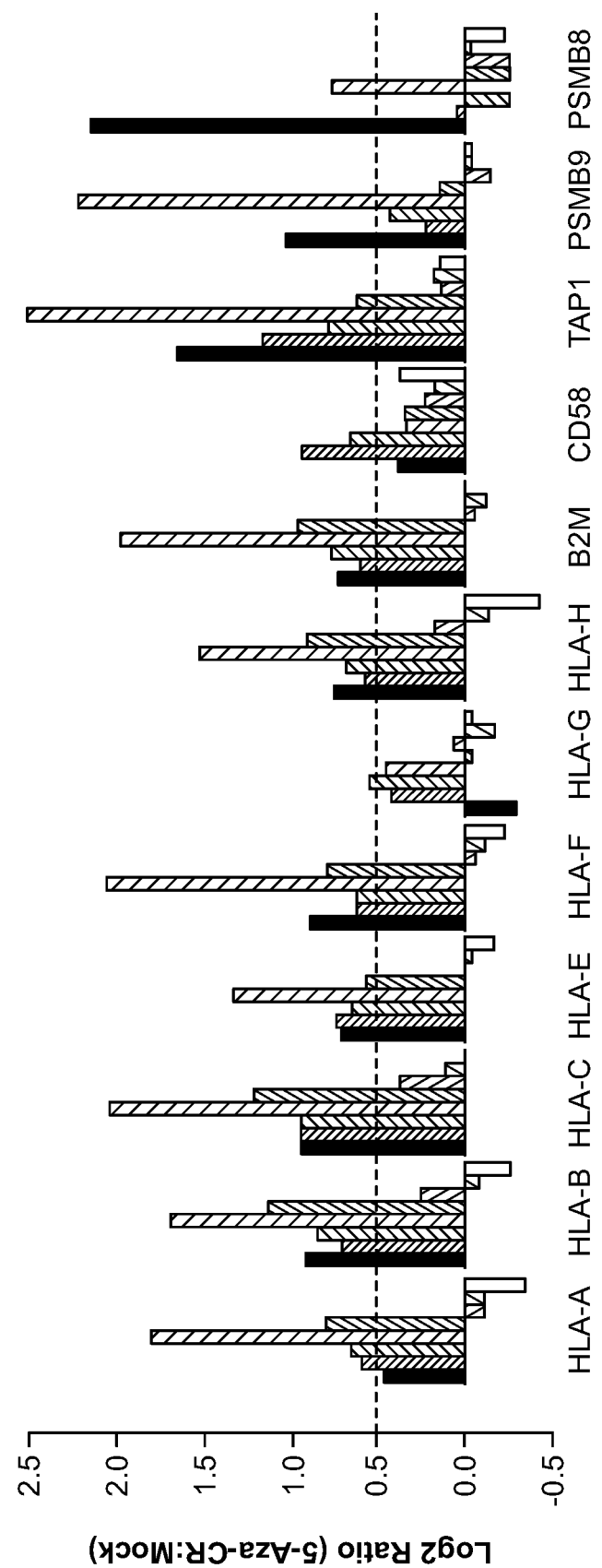
Figure 16E:
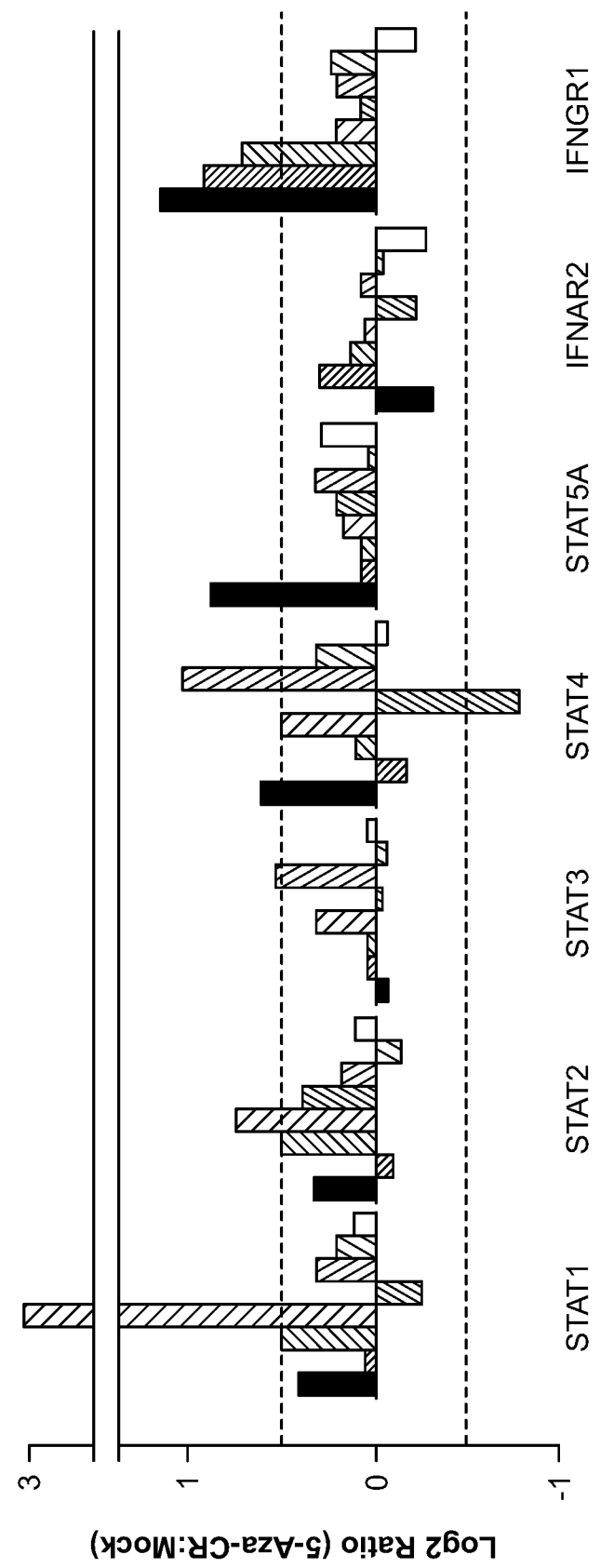
Figure 16F:
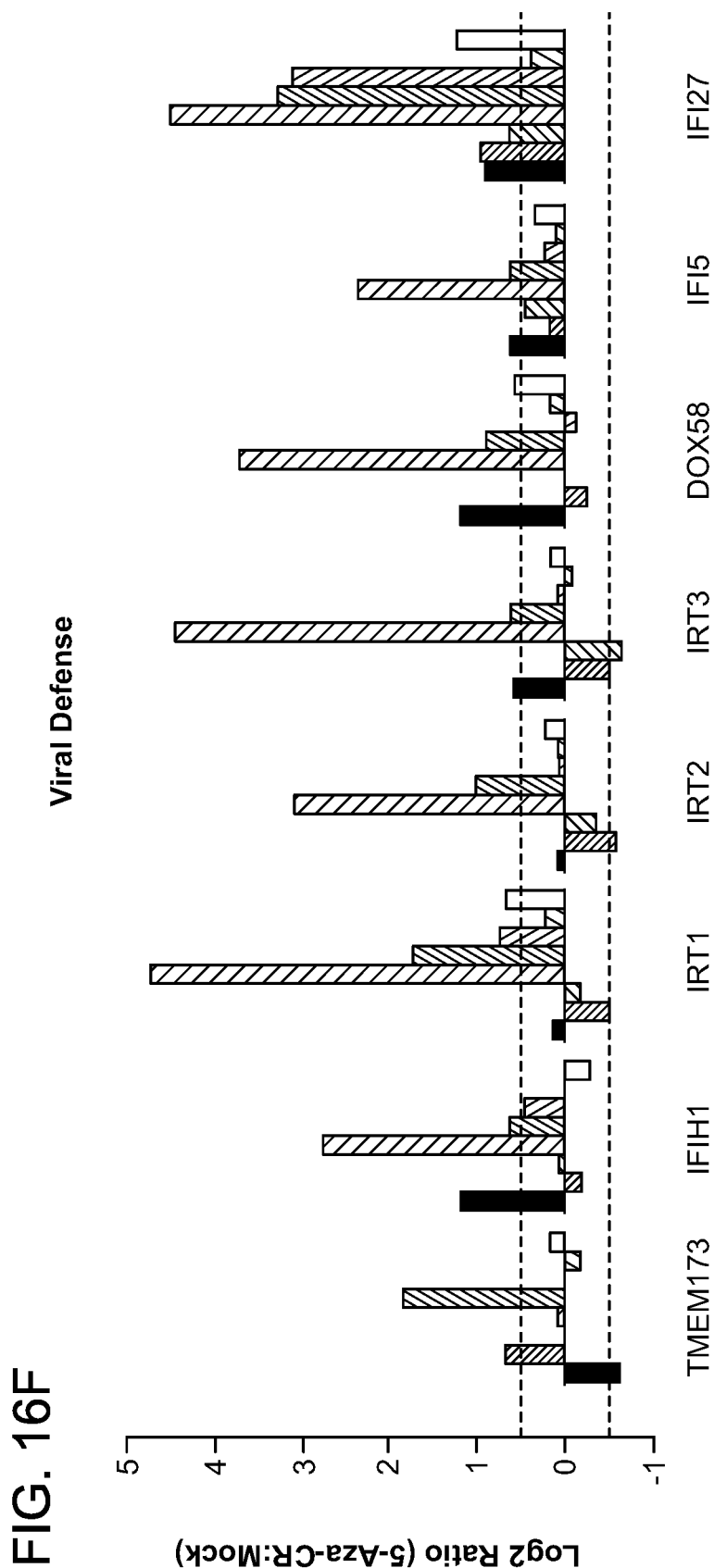
Figure 16G:
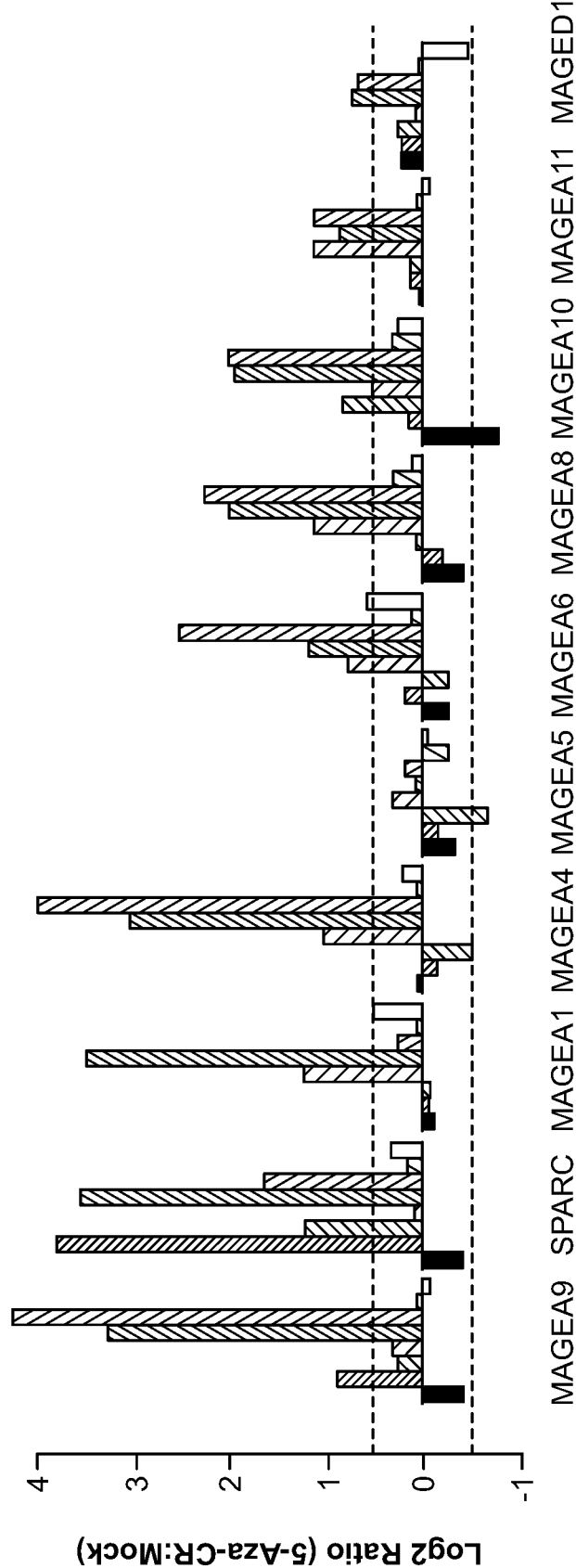
Figure 16I:
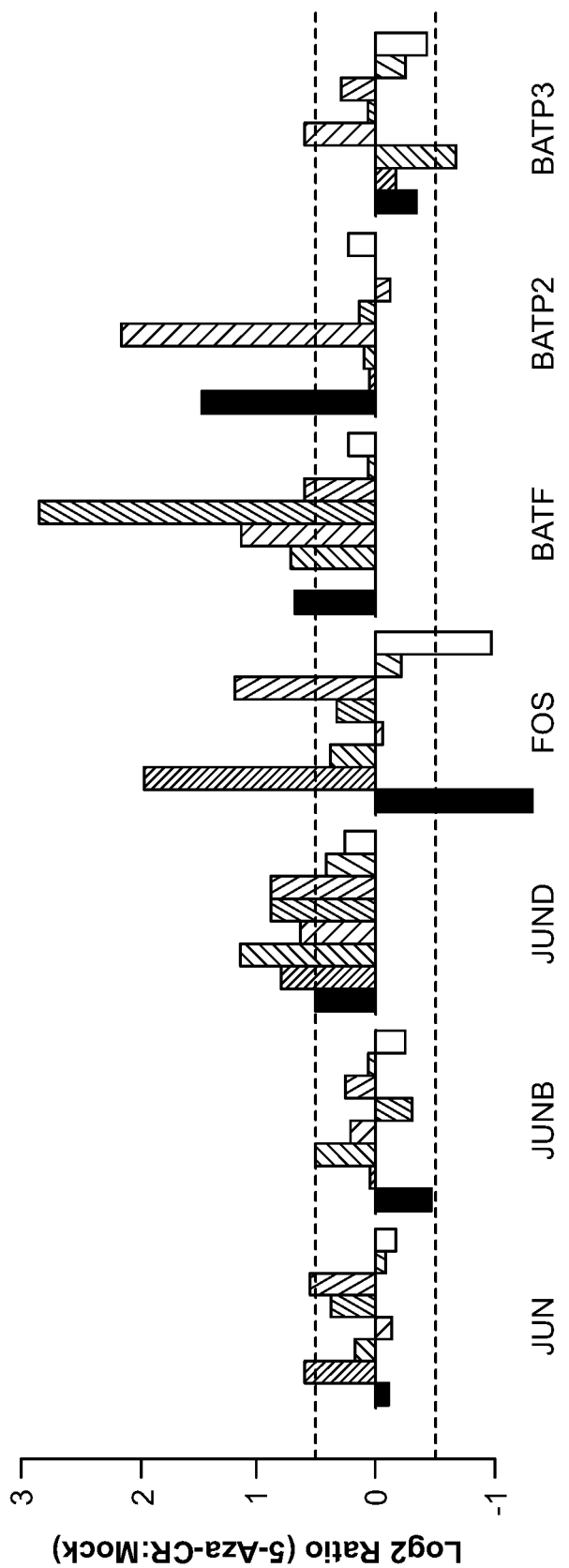

A key component of tumor recognition and killing by cytotoxic T-cells involves recognition of peptides derived from tumor-specific antigens or up-regulated shared antigens bound to HLA Class I antigens expressed by the tumor cells (30). In previous instances, AZA was shown to increase expression of multiple cancer testes antigens including multiple MAGE family genes, whose expression was shown to be suppressed by promoter hypermethylation (14, 15) (FIG. 16G). AZA upregulates not only transcripts of HLA Class I antigens but also a series of genes including beta-2-microglobulin (B2M), CD58, TAP1, and the immuno-proteasome subunits PMSB9 and PSMB8, which encode proteins required for endoplasmic reticulum processing of, transport to, and anchoring to the cell surface, and recognition of surface HLA class I subunits (31-33) (FIG. 16D). Flow cytometry revealed generally good correlation between HLA Class I, B2M, CD58, and B7-H3 transcripts and protein on the cell surface (FIG. 24). It was noted that mutations potentially contributing to immune evasion were previously described in HLA-A in a small percentage of LUSC and of B2M and CD58 in other tumor types.(33, 34)

Type I and II Interferon Signaling

One issue for immune cell interaction with tumor cells is that, in vivo, AZA administration to tumor-bearing mice was previously shown to induce antigen processing and presentation genes, particularly when administered with CpG TLR9 agonists, and this was largely attributed to interferon-γ production by lymphocytes (13) Importantly, while the lymphocyte-specific γ-interferon was not induced in NSCLC lines with AZA treatment, up-regulation of the interferon-γ receptor (IFNGR1) as well as of multiple STAT genes, including STAT1, the major IFNGR1 signal transducer, was observed. (FIG. 16E)

Programmed Cell Death and Viral Defense

The re-expressed genes in the above mentioned pathways are downstream targets of interferon-response pathways in a manner closely linked to pro-inflammatory and viral defense responses (24, 35-37). In turn, triggering of these responses could have had both tumor repressing activities, such as apoptosis, or tumor promoting events, and this paradox has been termed "the dual face" of inflammation (35, 36, 38). Indeed, key subsets of immune-related genes were observed as up-regulated by AZA with potential for inhibiting tumor growth including IFI27, which encodes a protein that triggers apoptosis in late stages of chronic viral infection (39) (FIG. 16F). Simultaneously, down-regulation of the antiapoptotic gene, MAVS, was observed, a change which accompanied activation of the RIG I signaling pathway in response to viral challenge.(36, 37, 40) (FIG. 16H). Downstream events in viral response included (especially in cell line H838) simultaneous increases for expression of BIRC family autophagy genes and simultaneous decreases in the antiapoptotic genes BCL2 and BIRC5 (SURVIVIN)(41) (FIG. 16H). Indeed, suppression of SURVIVIN was previously described as triggered by the viral induction of IRAK3, which encodes an IL-1 receptor associated kinase. (42) IRAK3 was, again in H838 cells, up-regulated by AZA concordantly with the death related genes mentioned immediately above (FIG. 16H). These effects resembled those observed for colon cancer cells, where IRAK3 was silenced in association with promoter-region DNA hypermethylation and, when reactivated by induced demethylation, was associated with SURVIVIN down-regulation. (42)

PD-L1 Expression

Immune checkpoint therapy often involves antibody targeting of either the receptor PD-L1 on immune cells and/or the ligand PD-L1 on tumor cells (6, 7, 30). In clinical trials for immune checkpoint blockade performed to date that have involved NSCLC patients, a subset showed no responses when their tumors did not express cell surface PD-L1(6, 7, 30). In this regard, when treated with AZA, several NSCLC cell lines up-regulated PD-L1, not only at the transcript level but also at the cell surface protein level. (FIG. 16B, 16C) Notably, this AZA-induced increase of PD-L1 in cell lines was far more consistent than for PD-L2, a second dendritic cell/macrophage ligand for the CTL PD-1 receptor, or other checkpoint ligands such as B7-H3 and B7-H4. (FIG. 16C) Similarly, CD80 and CD86, the ligands for CTLA4, another therapeutically targeted immune checkpoint receptor, were not altered.(FIG. 16C) PD-L1 expression in tumor cells can either be driven by cell-intrinsic mechanisms or by a process termed adaptive resistance, through interferon-γ signaling and subsequent activation of STAT transcription factors, which were also induced by AZA (FIG. 16E).

Example 6

Figure 17:
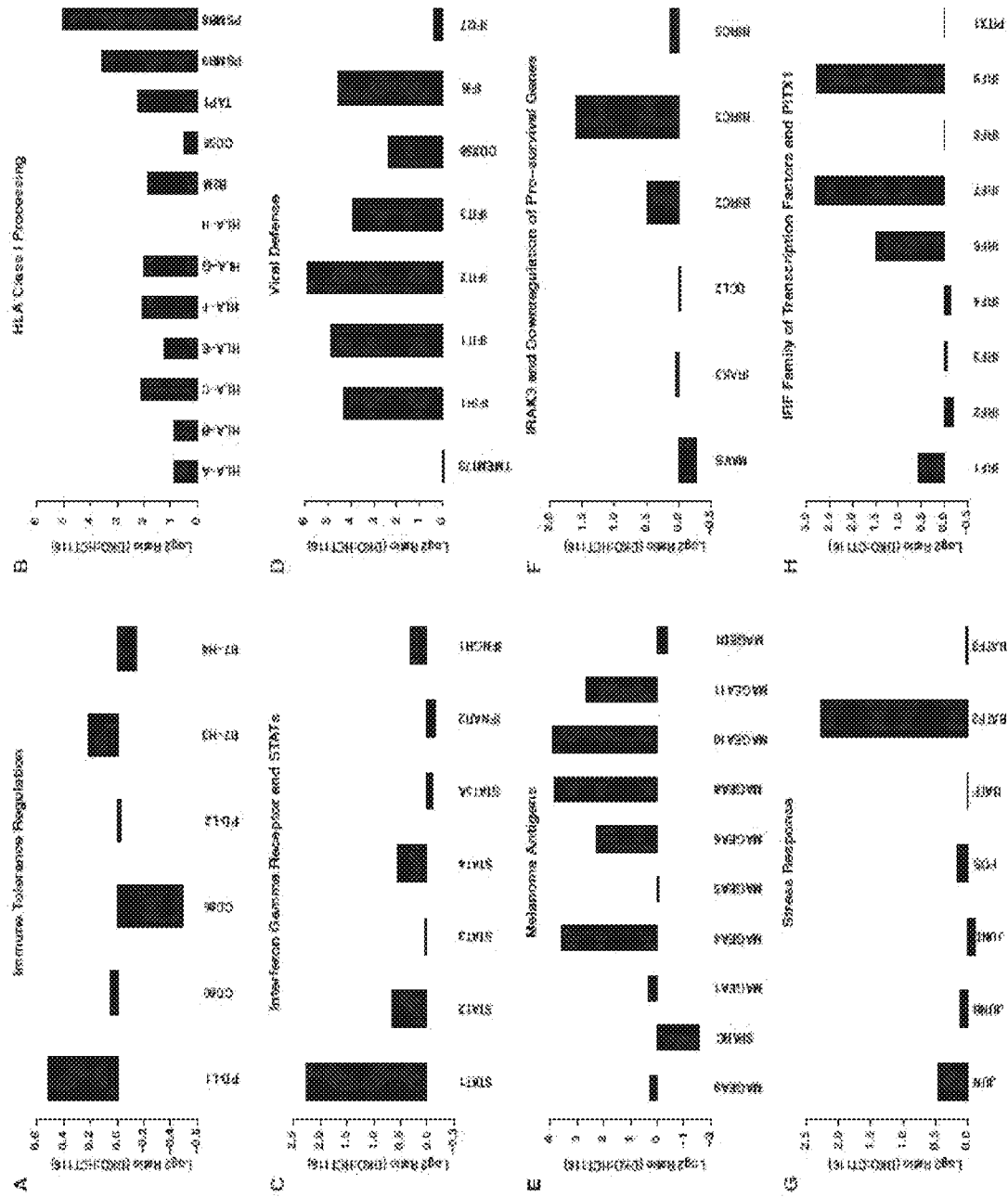
FIGS. 17A-H show that genetic knock out of DNA methyltransferases mimicked the effects of azacytidine mediated immune pathway up-regulation, specifically showing gene expression alterations when wild type HCT116 colon cancer cells were compared to their isogenic DNMT1 and 3B knockout counterpart (DKO). The gene expression differences are given as the log 2 ratio of expression in DKO over wild type cells (Y-axis) and the gene panels, FIGS. 17A-H correspond to panels of FIGS. 16C-J above for the NSCLC cell lines treated with AZA.

Azacytidine Altered the Immuno-Phenotype of NSCLC Through its Effect on DNA Methyltransferases It was necessary to assess whether the above results represented attributes of AZA as a targeted therapy. In this regard, this drug, particularly at less toxic doses, had previously been specifically identified as targeting the three biologically active DNMT's, acting to directly inhibit their catalytic sites and triggering degradation of these proteins in the nucleus (9, 43). Thus, it was relevant to assess how the complex, immune-related, pharmacologic responses described above compared to simultaneous genetic depletion of two of the three DNMT's. To do so, HCT116 colon cancer cells and HCT116 double knock out (DKO) cells were examined, which had been genetically disrupted to give severe haplo-insufficiency of DNMT1, and complete absence of DNMT3B, enzymes for DNA methylation maintenance and de novo DNA methylation, respectively.(44) Such cells had lost the majority of their genome-wide DNA methylation and exhibited de-methylation of many cancer specific, promoter region, of DNA hypermethylated CpG islands with corresponding re-expression of genes silenced in the wild type HCT 116 cells.(44) The immune-related expression alterations observed in DKO versus wild type HCT116 were discovered to be remarkably similar to the AZA-induced changes in NSCLC cells that had been observed. (FIG. 17) It was therefore concluded that previously described off target effects of high dose AZA, including incorporation into RNA and DNA as an abnormal nucleotide (10), did not appear to be required for the drug's effect defined herein.

Example 7

Up-Regulation of Immune Related Transcription Factors by Azacytidine

Figure 16J:
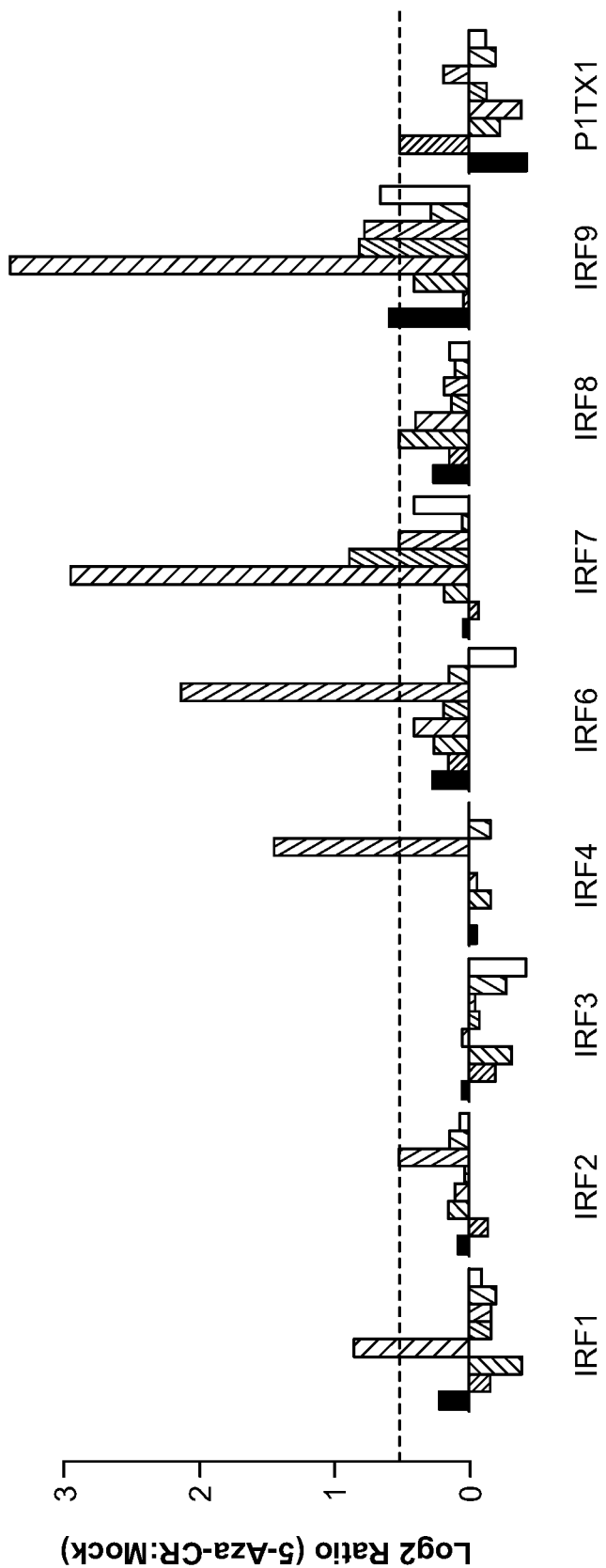
Figure 18:
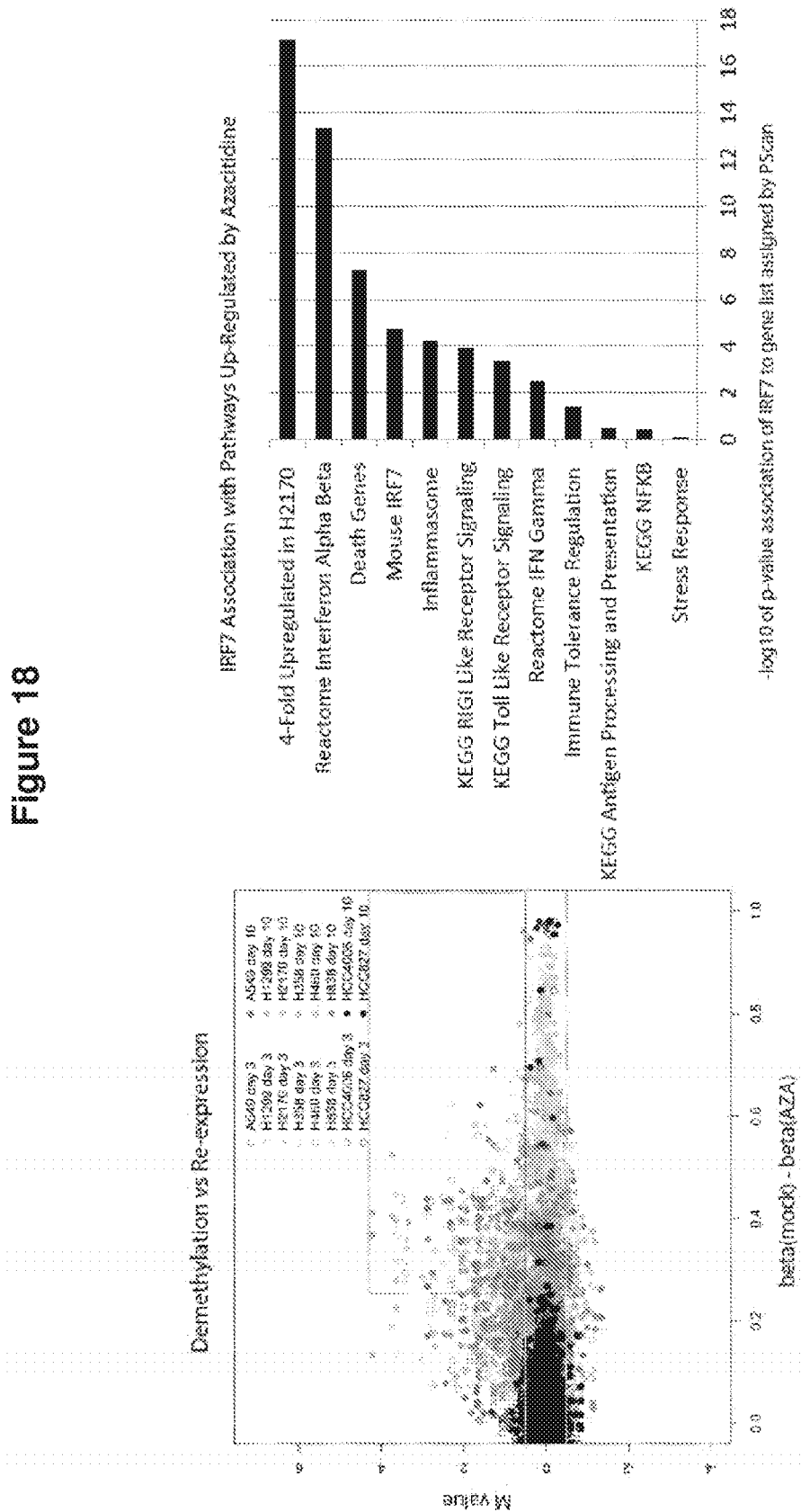
FIGS. 18-20 depict the identification of azacytidine up-regulated transcription factors and interferon signaling related genes, and their clustering of primary Non-Small Cell Lung Cancer in TCGA.

To identify specific genes re-expressed in response to AZA which might have been driving immune-related changes, the genome wide expression and methylation data from cell line experiments were extensively filtered. Transcription factors that met the criteria of epigenetically reexpressed genes were identified. Approximately 300 genes with high baseline promoter region CpG island methylation, promoter demethylation of 25% or more after treatment, and expression increased by $\log_2$ 0.5 (1.4-fold) or greater after treatment (FIGS. 18, 27A-C). Nearly 17% were found in an interferome database (45), and 19% were transcription factors(45, 46). IRF7, a transcription factor previously reported as hypermethylated in cancer, was found to be hypermethylated in the NSCLC line possessing the lowest basal expression.(11, 46-48) It was up-regulated in response to AZA in several cell lines, most prominently in LUSC cell line H2170, where it showed a 9-fold increase (FIG. 16J). IRF7 is an upstream activator of functions in cellular pathways recognizing the virus response element VRE-A to increase transcription of genes involved in type 1 IFN signaling.(11) IRF7 transcription targets were significantly associated with genes driving several of the GSEA enrichment scores for the immune pathway alterations observed in response to AZA (FIG. 18).

Immune-Phenotypes within Histologies in the Cancer Genome Atlas

Figure 20:
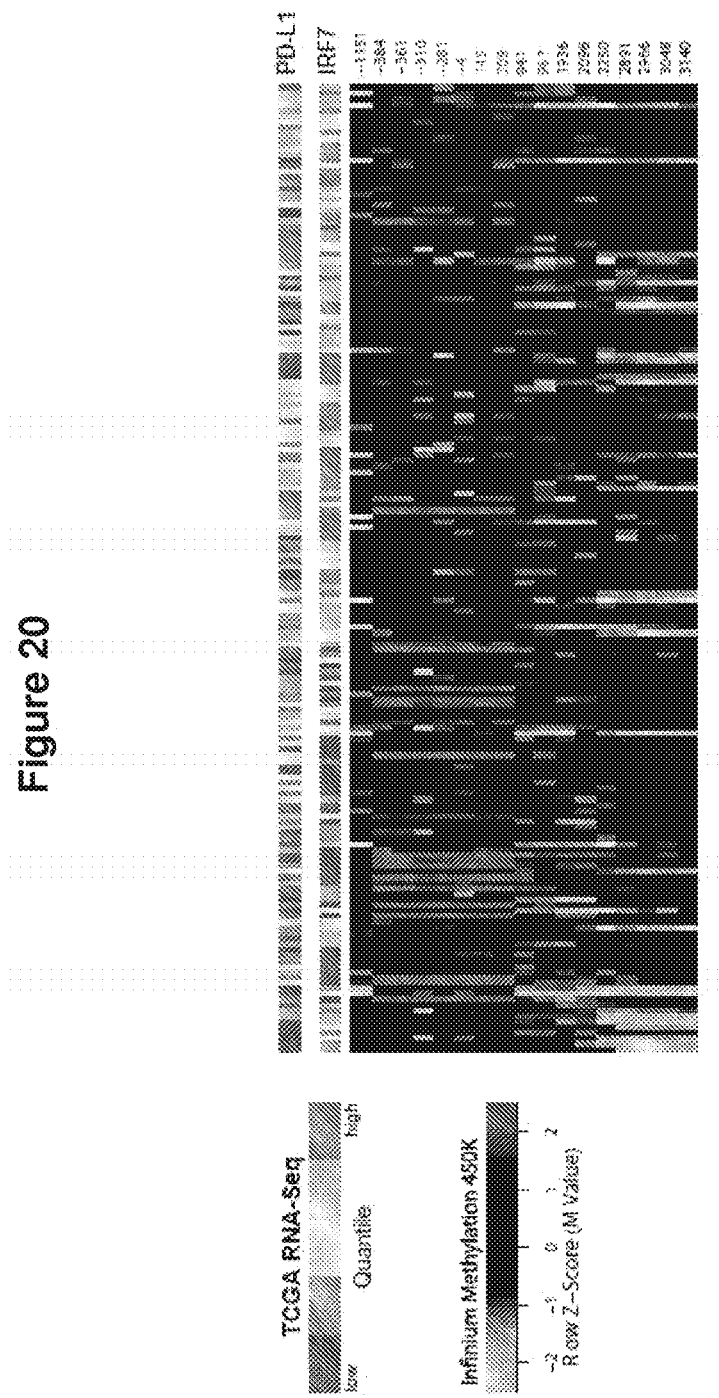
Figure 21:
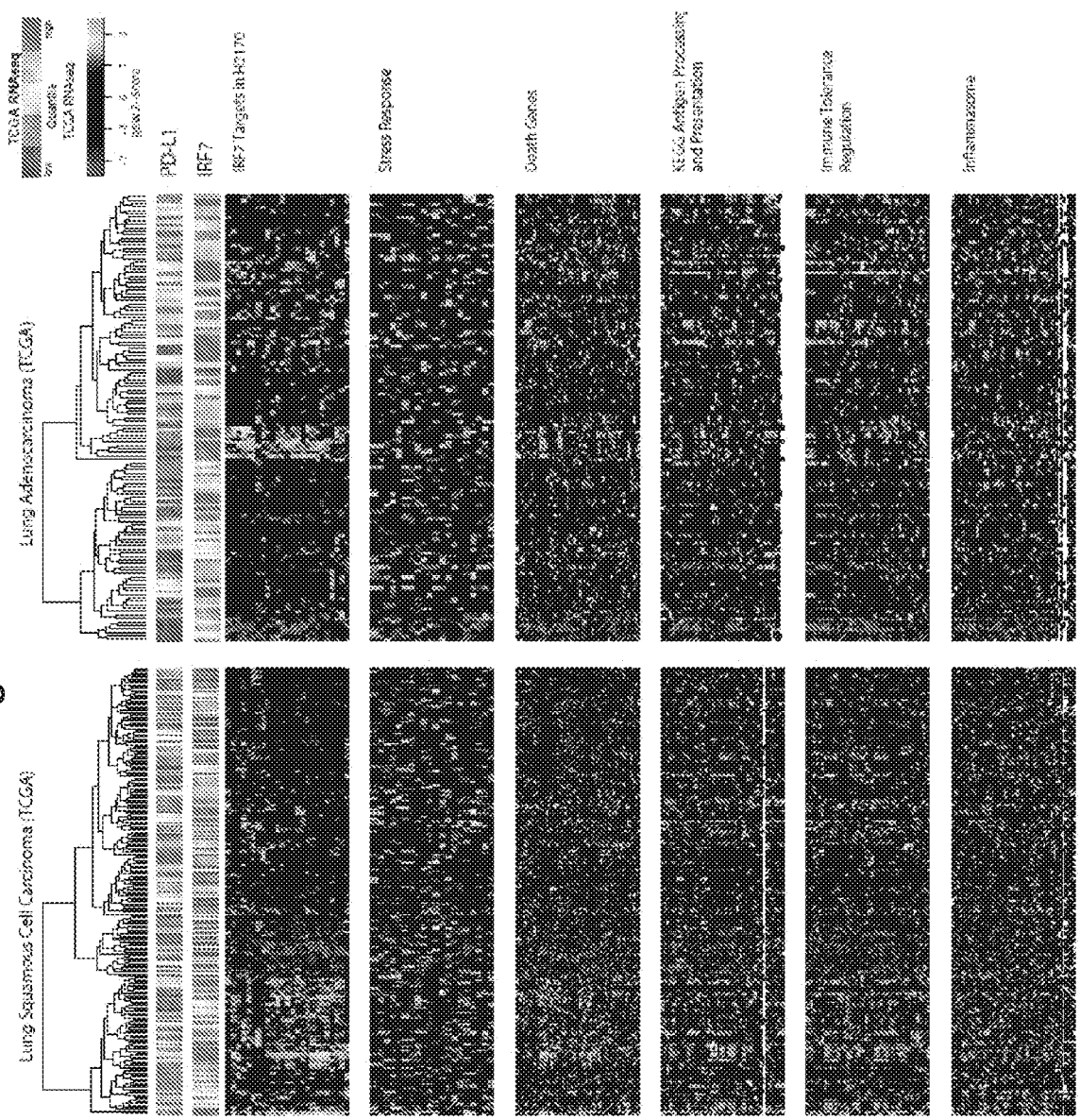
FIGS. 21 and 22 show the relationship of azacytidine-induced, immune-related pathways to primary lung tumors grouped by expression of IRF7-associated genes. TCGA samples were ordered by unsupervised clustering based on genes highly up-regulated in H2170, which were enriched for IRF7-targets, represented in the topmost heat map. The order of samples was maintained in all lower heat maps. PD-L1 and IRF7 expression are depicted in the top bar panels as in FIGS. 19-20.
Figure 22:
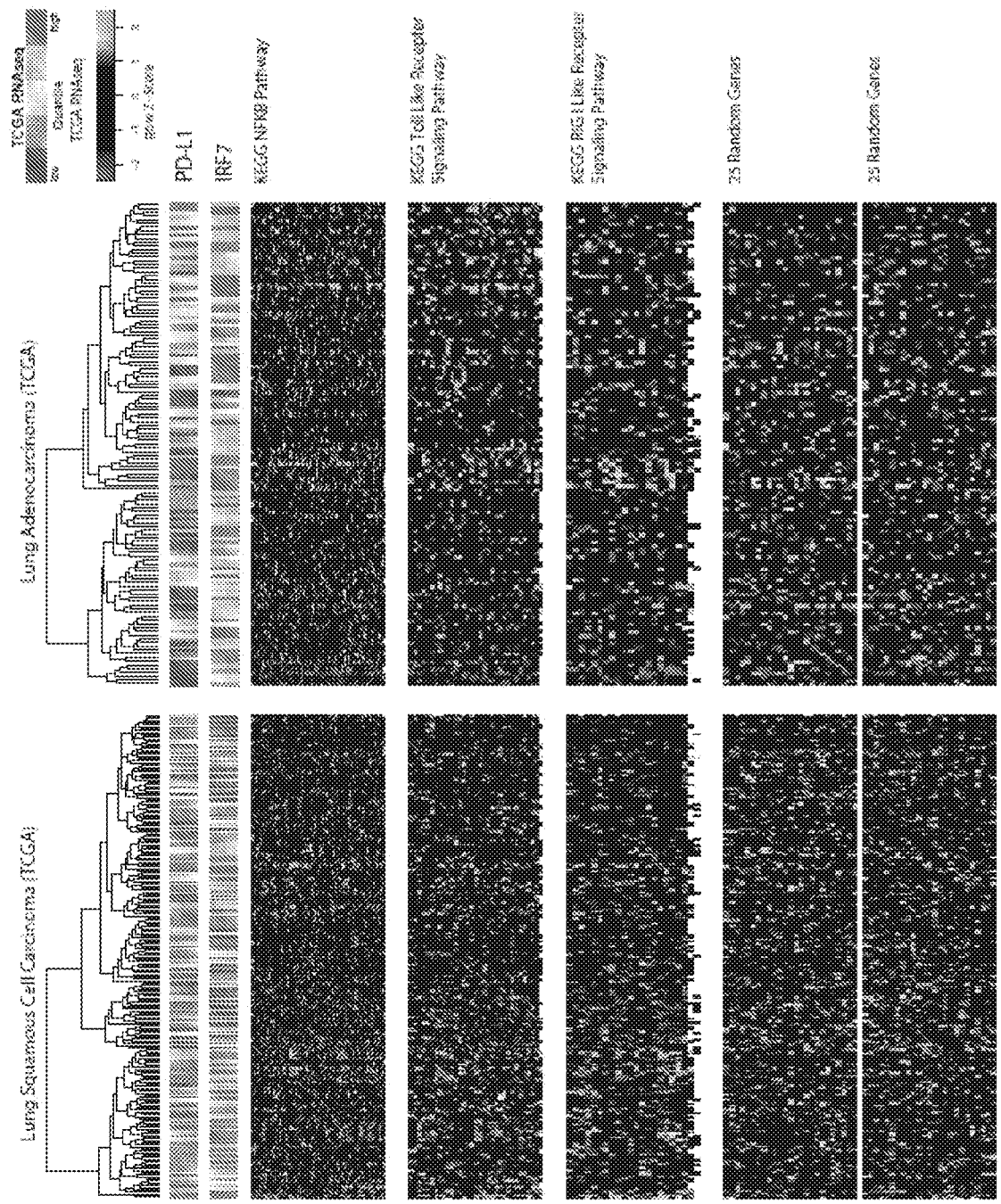

In view of the above analysis, which implicated IRF7 as an important cancer-specific hypermethylation induced down-regulation event, a list of functionally derived genes closely associated with IRF7 re-expression was sought. H2170, the LUSC cell line with the greatest up-regulation of IRF7 was examined, and it was hypothesized that other genes highly up-regulated in this cell line could be targets of this transcription factor. (FIG. 16J) Filtering expression array data, 114 genes were identified in H2170 cells as 4-fold or more up-regulated in response to AZA.(FIG. 25) The association of this functionally derived gene list with IRF7 was confirmed by PScan analysis (p=7.6 e-18). (FIG. 19). These data suggested that IRF7 silencing by DNA methylation in tumors could have resulted in suppression of immune-regulatory genes important for the surveillance of tumors by cytotoxic immune mechanisms. An immune-evasion signature dependent on IRF7 in breast and melanoma has been reported (46, 56). To test if such relation between IRF7 and immune-regulatory genes existed in primary LUAD and LUSC tumors, the expression of these genes was analyzed as a function of IRF7 expression, and its promoter methylation status. Low expression of these genes was then identified to describe a subgroup of LUSC in TCGA samples that clustered with high methylation levels and low expression of IRF7. (FIGS. 18-22, FIG. 26). Finally, expression levels of PD-L1, the key tumor ligand targeted in the anti-checkpoint immunotherapy trials, tracked quite well with the above immune evasion signature in subgroups of not only LUSC, but also LUAD, as was especially well visualized in heat maps for individual immune related pathways, which each tracked closely with an immune evasion signature in the LUSC and LUAD, TCGA samples (FIGS. 20-22)

In the preceding Examples, AZA was identified to up-regulate genes and pathways related to immune evasion in most NSCLC lines, which constituted an immune signature in primary NSCLC. DNA hypermethylation and low expression of IRF7, an upstream interferon transcription factor, tracked with this signature, particularly in a subset of LUSC. In concert with these events, AZA up-regulated PD-L1 transcripts and protein, and low expression of this key target of immune checkpoint therapy tracked with the immune evasion signature.

Thus, epigenetic therapy combined with blockade of immune checkpoints—in particular the PD-1/PD-L1 pathway—was identified as likely to augment the response of NSCLC by shifting the balance between immune activation and immune inhibition, particularly in a subset of NSCLC with low expression of these pathways. The above Examples have also identified a biomarker strategy for assessing response in a recently initiated trial designed to examine the potential of epigenetic therapy to sensitize patients with NSCLC to PD-1 immune checkpoint blockade.

REFERENCES

1. Siegel R, Naishadham D, Jemal A. Cancer statistics, 2013. CA Cancer J Clin 2013; 63: 11-30.
2. Youlden D R, Cramb S M, Baade P D. The International Epidemiology of Lung Cancer: geographical distribution and secular trends. J Thorac Oncol 2008; 3: 819-31.
3. Vadakara J, Borghaei H. Personalized medicine and treatment approaches in non-small-cell lung carcinoma. Pharmgenomics Pers Med 2012; 5: 113-23.
4. Shepherd F A, Rodrigues Pereira J, Ciuleanu T, et al. Erlotinib in previously treated non-small-cell lung cancer. N Engl J Med 2005; 353: 123-32.
5. Juergens R A, Wrangle J, Vendetti F P, et al. Combination epigenetic therapy has efficacy in patients with refractory advanced non-small cell lung cancer. Cancer Discov 2011; 1: 598-607.
6. Brahmer J R, Tykodi S S, Chow L Q, et al. Safety and activity of anti-P D-L1 antibody in patients with advanced cancer. N Engl J Med 2012; 366: 2455-65.
7. Topalian S L, Hodi F S, Brahmer J R, et al. Safety, activity, and immune correlates of anti-PD-1 antibody in cancer. N Engl J Med 2012; 366: 2443-54.
8. Brahmer J R, Horn L, Antonia S J, et al. Survival and long-term follow-up of the phase I trial of nivolumab (Anti-PD-1; BMS-936558; ONO-4538) in patients (pts) with previously treated advanced non-small cell lung cancer (NSCLC). ASCO Meeting Abstracts 2013; 31: 8030.
9. Gabbara S, Bhagwat A S. The mechanism of inhibition of DNA (cytosine-5-)-methyltransferases by 5-azacytosine is likely to involve methyl transfer to the inhibitor. Biochem J 1995; 307 (Pt 1): 87-92.
10. Stresemann C, Lyko F. Modes of action of the DNA methyltransferase inhibitors azacytidine and decitabine. Int J Cancer 2008; 123: 8-13.
11. Li Q, Tainsky M A. Epigenetic silencing of IRF7 and/or IRF5 in lung cancer cells leads to increased sensitivity to oncolytic viruses. PLoS One 2011; 6: e28683.
12. Kulaeva O I, Draghici S, Tang L, Kraniak J M, Land S J, Tainsky M A. Epigenetic silencing of multiple interferon pathway genes after cellular immortalization. Oncogene 2003; 22: 4118-27.
13. Simova J, Pollakova V, Indrova M, et al Immunotherapy augments the effect of 5-azacytidine on HPV 16-associated tumours with different MHC class I-expression status. Br J Cancer 2011; 105: 1533-41.
14. Fonsatti E, Nicolay H J, Sigalotti L, et al. Functional up-regulation of human leukocyte antigen class I antigens expression by 5-aza-2'-deoxycytidine in cutaneous melanoma: immunotherapeutic implications. Clin Cancer Res 2007; 13: 3333-8.
15. Claus R, Almstedt M, Lubbert M. Epigenetic treatment of hematopoietic malignancies: in vivo targets of demethylating agents. Semin Oncol 2005; 32: 511-20.
16. Karpf A R, Peterson P W, Rawlins J T, et al Inhibition of DNA methyltransferase stimulates the expression of signal transducer and activator of transcription 1, 2, and 3 genes in colon tumor cells. Proc Natl Acad Sci USA 1999; 96: 14007-12.
17. Tsai H C, Li H, Van Neste L, et al. Transient Low Doses of DNA-Demethylating Agents Exert Durable Antitumor Effects on Hematological and Epithelial Tumor Cells. Cancer Cell 2012; 21: 430-46.
18. Silverman L R, Demakos E P, Peterson B L, et al. Randomized controlled trial of azacytidine in patients with the myelodysplastic syndrome: a study of the cancer and leukemia group B. J Clin Oncol 2002; 20: 2429-40.
19. Schreiber R D, Old L J, Smyth M J. Cancer immuno-editing: integrating immunity's roles in cancer suppression and promotion. Science 2011; 331: 1565-70.
20. Khong H T, Restifo N P. Natural selection of tumor variants in the generation of "tumor escape" phenotypes. Nat Immunol 2002; 3: 999-1005.
21. Tomasi T B, Magner W J, Khan A N. Epigenetic regulation of immune escape genes in cancer. Cancer Immunol Immunother 2006; 55: 1159-84.
22. Gentleman R C, Carey V J, Bates D M, et al. Bioconductor: open software development for computational biology and bioinformatics. Genome Biol 2004; 5: R80.
23. Smyth G K, Speed T. Normalization of cDNA microarray data. Methods 2003; 31: 265-73.
24. Strowig T, Henao-Mejia J, Elinav E, Flavell R. Inflammasomes in health and disease. Nature 2012; 481: 278-86.
25. Ravasi T, Suzuki H, Cannistraci C V, et al. An atlas of combinatorial transcriptional regulation in mouse and man. Cell 2010; 140: 744-52.
26. Vaquerizas J M, Akhtar A, Luscombe N M. Large-scale nuclear architecture and transcriptional control. Sub-cellular biochemistry 2011; 52: 279-95.

27. Vaquerizas J M, Teichmann S A, Luscombe N M. How do you find transcription factors? Computational approaches to compile and annotate repertoires of regulators for any genome. Methods Mol Biol 2012; 786: 3-19.
28. Lopez F, Textoris J, Bergon A, et al. TranscriptomeBrowser: a powerful and flexible toolbox to explore productively the transcriptional landscape of the Gene Expression Omnibus database. PLoS ONE 2008; 3: e4001.
29. Aaltonen T, Adelman J, Akimoto T, et al. Precision measurement of the X(3872) mass in J/psi pi(+) pi(−) decays. Phys Rev Lett 2009; 103: 152001.
30. Pardoll D M. The blockade of immune checkpoints in cancer immunotherapy. Nat Rev Cancer 2012; 12: 252-64.
31. Raghavan M, Del Cid N, Rizvi S M, Peters L R. MHC class I assembly: out and about. Trends Immunol 2008; 29: 436-43.
32. Procko E, Gaudet R. Antigen processing and presentation: TAPping into ABC transporters. Curr Opin Immunol 2009; 21: 84-91.
33. Challa-Malladi M, Lieu Y K, Califano O, et al. Combined genetic inactivation of beta2-Microglobulin and CD58 reveals frequent escape from immune recognition in diffuse large B cell lymphoma. Cancer Cell 2011; 20: 728-40.
34. Hammerman P S, Hayes D N, Wilkerson M D, et al. Comprehensive genomic characterization of squamous cell lung cancers. Nature 2012; 489: 519-25.
35. Ishikawa H, Ma Z, Barber G N. STING regulates intracellular DNA-mediated, type I interferon-dependent innate immunity. Nature 2009; 461: 788-92.
36. Sharma S, Fitzgerald K A. Viral defense: it takes two MAVS to Tango. Cell 2010; 141: 570-2.
37. Hsu T H, Chu C C, Jiang S Y, et al. Expression of the class II tumor suppressor gene RIG1 is directly regulated by p53 tumor suppressor in cancer cell lines. FEBS Lett 2012; 586: 1287-93.
38. Dunn G P, Bruce A T, Ikeda H, Old L J, Schreiber R D. Cancer immunoediting: from immunosurveillance to tumor escape. Nat Immunol 2002; 3: 991-8.
39. Cheriyath V, Leaman D W, Borden E C. Emerging roles of FAM14 family members (G1P3/ISG 6-16 and ISG12/IFI27) in innate immunity and cancer. J Interferon Cytokine Res 2011; 31: 173-81.
40. Xu Y, Zhong H, Shi W. MAVS protects cells from apoptosis by negatively regulating VDAC1. Mol Cell Biochem 2010.
41. Yang Z, Klionsky D J. Mammalian autophagy: core molecular machinery and signaling regulation. Curr Opin Cell Biol 2010; 22: 124-31.
42. De Carvalho D D, Sharma S, You J S, et al. DNA methylation screening identifies driver epigenetic events of cancer cell survival. Cancer Cell 2012; 21: 655-67.
43. Santi D V, Norment A, Garrett C E. Covalent bond formation between a DNA-cytosine methyltransferase and DNA containing 5-azacytosine. Proc Natl Acad Sci USA 1984; 81: 6993-7.
44. Rhee I, Bachman K E, Park B H, et al. DNMT1 and DNMT3b cooperate to silence genes in human cancer cells. Nature 2002; 416: 552-6.
45. Samarajiwa S A, Forster S, Auchettl K, Hertzog P J. INTERFEROME: the database of interferon regulated genes. Nucleic Acids Res 2009; 37: D852-7.
46. Bidwell B N, Slaney C Y, Withana N P, et al. Silencing of Irf7 pathways in breast cancer cells promotes bone metastasis through immune escape. Nat Med 2012.
47. Jee C D, Kim M A, Jung E J, Kim J, Kim W H. Identification of genes epigenetically silenced by CpG methylation in human gastric carcinoma. Eur J Cancer 2009; 45: 1282-93.
48. Lu R, Au W C, Yeow W S, Hageman N, Pitha P M. Regulation of the promoter activity of interferon regulatory factor-7 gene. Activation by interferon snd silencing by hypermethylation. J Biol Chem 2000; 275: 31805-12.
49. Tsai H C, Li H, Van Neste L, et al. Transient low doses of DNA-demethylating agents exert durable antitumor effects on hematological and epithelial tumor cells. Cancer Cell; 21: 430-46.
50. Gregory R W, Bolker B, Bonebakker L, et al. gplots: Various R programming tools for plotting data. R package version 2.11.0. 2012.
51. Subramanian A, Kuehn H, Gould J, Tamayo P, Mesirov J P. GSEA-P: a desktop application for Gene Set Enrichment Analysis. Bioinformatics 2007; 23: 3251-3.
52. Subramanian A, Tamayo P, Mootha V K, et al. Gene set enrichment analysis: a knowledge-based approach for interpreting genome-wide expression profiles. Proc Natl Acad Sci USA 2005; 102: 15545-50.
53. Nakaya A, Katayama T, Itoh M, et al. KEGG O C: a large-scale automatic construction of taxonomy-based ortholog clusters. Nucleic Acids Res 2013; 41: D353-7.
54. Joshi-Tope G, Gillespie M, Vastrik I, et al. Reactome: a knowledgebase of biological pathways. Nucleic Acids Res 2005; 33: D428-32.
55. Zambelli F, Pesole G, Pavesi G. Pscan: finding over-represented transcription factor binding site motifs in sequences from co-regulated or co-expressed genes. Nucleic Acids Res 2009; 37: W247-52.
56. Carretero R, Wang E, Rodriguez A I, et al. Regression of melanoma metastases after immunotherapy is associated with activation of antigen presentation and interferon-mediated rejection genes. Int J Cancer; 131: 387-95.

We claim:

1. A method of treating a neoplastic condition in a human subject in need thereof consisting of:
   administering to the human subject (i) a first agent that is a DNA methyl transferase (DNMT) inhibitor and (ii) a second agent that is human or humanized anti-PD-1 antibody, thereby treating the neoplastic condition in the human subject,
   wherein the neoplastic condition is lung cancer, colon cancer or ovarian cancer,
   wherein the first agent is administered before the second agent, and
   wherein the first agent increases PD-L1 protein level expression in the lung cancer, colon cancer or ovarian cancer.

2. The method of claim 1, wherein said first agent is selected from the group consisting of 5-azacytidine, 5-aza-2'-deoxycytidine, and a dinucleotide containing 5-aza-CdR.

3. The method of claim 2, wherein said first agent is 5-aza-2'-deoxycytidine.

4. The method of claim 1, wherein said neoplastic condition is lung cancer.

5. The method of claim 4, wherein said lung cancer is non-small cell lung cancer (NSCLC).

6. The method of claim 1, wherein shrinkage of the neoplastic condition in said human subject occurs.

7. The method of claim 1, wherein said administering stabilizes the neoplastic condition in said human subject.

8. The method of claim 7, wherein said stabilization is for a duration of one month or more.

* * * * *